United States Patent
Loessner et al.

(10) Patent No.: US 9,789,167 B2
(45) Date of Patent: Oct. 17, 2017

(54) POLYPEPTIDE MIXES WITH ANTIBACTERIAL ACTIVITY

(71) Applicant: Micreos Human Health B.V., The Hague (NL)

(72) Inventors: Martin Johannes Loessner, Ebmatingen (CH); Fritz Eichenseher, Zurich (CH)

(73) Assignee: MICREOS HUMAN HEALTH B.V., The Hague (NL)

( * ) Notice: Subject to any disclaimer, the term of this patent is extended or adjusted under 35 U.S.C. 154(b) by 0 days.

(21) Appl. No.: 14/399,643

(22) PCT Filed: May 7, 2013

(86) PCT No.: PCT/NL2013/050344
§ 371 (c)(1),
(2) Date: Nov. 7, 2014

(87) PCT Pub. No.: WO2013/169104
PCT Pub. Date: Nov. 14, 2013

(65) Prior Publication Data
US 2015/0118189 A1 Apr. 30, 2015

Related U.S. Application Data

(60) Provisional application No. 61/643,417, filed on May 7, 2012.

(30) Foreign Application Priority Data

May 7, 2012 (EP) .................................. 12166977

(51) Int. Cl.
| | | |
|---|---|---|
| *A61K 38/46* | (2006.01) |
| *A23L 3/3463* | (2006.01) |
| *C12N 9/50* | (2006.01) |
| *C12N 9/80* | (2006.01) |
| *C12N 9/00* | (2006.01) |
| *A23B 4/22* | (2006.01) |
| *A61K 38/16* | (2006.01) |
| *A61K 38/54* | (2006.01) |
| *A61K 38/48* | (2006.01) |
| *A61K 38/50* | (2006.01) |
| *A61K 45/06* | (2006.01) |
| *A61K 38/43* | (2006.01) |

(52) U.S. Cl.
CPC ................ *A61K 38/46* (2013.01); *A23B 4/22* (2013.01); *A23L 3/3463* (2013.01); *A23L 3/34635* (2013.01); *A61K 38/162* (2013.01); *A61K 38/48* (2013.01); *A61K 38/50* (2013.01); *A61K 38/54* (2013.01); *A61K 45/06* (2013.01); *C12N 9/00* (2013.01); *C12N 9/503* (2013.01); *C12N 9/80* (2013.01); *A23V 2002/00* (2013.01); *A61K 38/43* (2013.01)

(58) Field of Classification Search
CPC . A61K 38/46; C12Y 302/01017; C12N 9/503
See application file for complete search history.

(56) References Cited

U.S. PATENT DOCUMENTS

| | | | |
|---|---|---|---|
| 9,279,118 B2 * | 3/2016 | Fischetti | ............. C07K 14/005 |
| 2010/0028324 A1 | 2/2010 | Donovan | |
| 2012/0171188 A1 * | 7/2012 | Loessner | .......... G01N 33/56911 424/94.3 |
| 2016/0208231 A1 * | 7/2016 | Fischetti | ............. C12N 9/2462 424/94.61 |

FOREIGN PATENT DOCUMENTS

WO 2010/011960 A2 1/2010

OTHER PUBLICATIONS

XP055146552_DOORBRAAK in ontstekingsbestrijding; PARADERMICA Jun_13.indd_16 and English Translation; XP-002731103_How does Gladskin work? (Web.archive.org/web/20130320002931/http://www.gladskin).
Fenton et al., "Bacteriophage-Derived Peptidase CHAPk Eliminates and Prevents Staphylococcal Biofilms" XP-002709985_Hindawi Publishing Corp., International Journal of Microbiology, vol. 2013, Article ID 625341, 8 pages.
Abaev et al., "Staphylococcal Phage 2638A endolysin is lytic for *Staphylococcus aureus* and harbors an inter-lytic-domain secondary translational start site" Appl Microbiol Biotechnol (2013) 97:3449-3456.
Hung et al., "*Staphylococcus* colonization in atopic dermatitis treated with fluticasone or tacrolimus with or without antibiotics" Annals of Allergy, Asthma & Immunology (2007) 98: 51-56.
Friedman and Goldman, "Anti-staphylococcal treatment in dermatitis" XP-002709984, Child Health Update (2011) 57: 669-671.
Choudhury et al., "Staphylococcal Infection, Antibiotic Resistance and Therapeutics", XP-002709983, pp. 247-272.
Schmelcher Mathias, et al., "Chimeric Phage Lysins Act Synergistically with Lysostaphin to Kill Mastitis-Causing *Staphylococcus aureus* in Murine Mammary Glands", Applied and Environmental Microbiology, vol. 78, No. 7, Apr. 2012 (Apr. 2012), pp. 2297-2305, XP009162654, ISSN: 0099-2240, the whole document.
Rodriguez-Rubio Lorena, et al., "Enhanced Staphylolytic Activity of the *Staphylococcus aureus* Bacteriophage vB_SauS-philPLA88 HydH5 Virion-Associated Peptidoglycan Hydrolase: Fusions, Deletions, and Synergy with LysH5", Applied and Environmental Microbiology, vol. 78, No. 7, Apr. 2012 (Apr. 2012), pp. 2241-2248, XP009162655, ISSN: 0099-2240, the whole document.

(Continued)

*Primary Examiner* — Karen Cochrane Carlson
(74) *Attorney, Agent, or Firm* — Volpe and Koenig, P.C.

(57) ABSTRACT

The invention relates to the field of microbiology, specifically to a combination of a source of a first enzymatic active domain and a source of a second enzymatic active domain and to a composition comprising said combination. The invention further relates to a composition comprising said combination for use as a medicament, to the use of said composition as an antimicrobial agent and to a method for controlling microbial contamination in a food- or feed product, on and/or in food- or feed processing equipment, on and/or in food- or feed containers.

7 Claims, 20 Drawing Sheets

(56) References Cited

OTHER PUBLICATIONS

Loeffler, JM, et al., "Synergistic Lethal Effect of a Combination of Phage Lytic Enzymes with Different Activities on Penicillin-Sensitive and -Resistant *Streptococcus* Pneumoniae Strains", Antimicrobial Agents and Chemotherapy, American Society for Microbiology, Washington, DC, US, vol. 47, No. 1, Jan. 1, 2003 (Jan. 1, 2003), pp. 375-377, XP008060688, ISSN: 0066-4804, DOI: 10.1128/AAC.47.1.375-377.2003, the whole document.
Becker, Stephen, et al., "The phage K lytic enzyme LysK and lysostaphin act synergistically to kill", FEMS Microbiology Letters, No longer Published by Elsevier, vol. 287, No. 2, Oct. 1, 2008 (Oct. 1, 2008), pp. 185-191, XP009151601, ISSN: 0378-1097, the whole document.
Lui, X., et al., "Nickel-inducible lysis system in Synechocystis sp. PCC 6803", Proceedings of the National Academy of Sciences, vol. 106, No. 51, Dec. 22, 2009 (Dec. 22, 2009), pp. 21550-21554, XP055037740, ISSN: 0027-8424, DOI: 10.1073/pnas.0911953106, the whole document.
Caparelli, R., et al., "Experimental Phage Therapy against *Staphylococcus aureus* in Mice", Antimicrobial Agents and Chemotherapy, American Society for Microbiology, Washington, DC, US, vol. 51, No. 8, Aug. 1, 2007, (Aug. 1, 2007), pp. 2765-2773, XP002481832, ISSN: 0066-4804, DOI: 10.1128/Aac.01513-06 (retrieved on May 21, 2007) abstract.
International Search Report, PCT/NL2013/050344, Jul. 8, 2013, 6 pp.

\* cited by examiner

SEQUENCE LISTING

<160> NUMBER OF SEQ ID NOS: 74

<210> SEQ ID NO 1
<211> LENGTH: 1461
<212> TYPE: DNA
<213> ORGANISM: Staphylococcus bacteriophage 2638A

<400> SEQUENCE: 1

```
atgctaactg ctattgacta tcttacgaaa aaaggttgga aaatatcatc tgaccctcgc        60
acttacgatg ttaccctaa aaactacggc tacagaaatt accatgaaaa cggcattaat        120
tatgatgagt tttgtggtgg ttatcataga gcttttgatg tttacagtaa cgaaactaac       180
gacgtgcctg ctgttactag cggaacagtt attgaagcaa acgattacgg taattttggt       240
ggtacattcg ttattagaga cgctaacgat aacgattgga tatatgggca tctacaacgt       300
ggctcaatgc gatttgttgt aggcgacaaa gtcaatcaag gtgacattat tggtttacaa       360
ggtaatagca actattacga caatcctatg agtgtacatt tacatttaca attacgccct       420
aaagacgcaa agaaagatga aaatcacaa gtatgtagtg gtttggctat ggaaaaatat       480
gacattacaa atttaaatgc taaacaagat aaatcaaaga tgggagcgt gaaagagttg       540 aaacatatct attcaaacca tattaaaggt aacaagatta cagcaccaaa acctagtatt       600
caaggtgtgg tcatccacaa tgattatggt agtatgacac ctagtcaata cttaccatgg       660
ttatatgcac gtgagaataa cggtacacac gttaacggtt gggctagtgt ttatgcaaat       720
agaaacgaag tgctttggta tcatccgaca gactacgtag agtggcattg tggtaatcaa       780
tgggcaaatg ctaacttaat cggatttgaa gtgtgtgagt cgtatcctgg tagaatctcg       840
gacaaattat tcttagaaaa tgaagaagcg acattgaaag tagctgcgga tgtgatgaag       900
tcgtacggat taccagttaa tcgcaacact gtacgtctgc ataacgaatt cttcggaact       960
tcttgtccac atcgttcgtg ggacttgcat gttggcaaag gtgagcctta cacaactact      1020
aatattaata aaatgaaaga ctacttcatc aaacgcatca acattatta tgacggtgga      1080 aagctagaag taagcaaagc agcaactatc aaacaatctg acgttaagca agaagttaaa      1140
aagcaagaag caaacaaat tgtgaaagca acagattgga aacagaataa agatggcatt      1200
tggtataaag ctgaacatgc ttcgttcaca gtgacagcac cagagggaat tatcacaaga      1260
tacaaaggtc cttggactgg tcacccacaa gctggtgtat tacaaaaagg tcaaacgatt      1320
aaatatgatg aggttcaaaa atttgacggt catgtttggg tatcgtggga aacgtttgag      1380
ggcgaaactg tatacatgcc ggtacgcaca tgggacgcta aaactggtaa agttggtaag      1440
ttgtggggcg aaattaaata a                                                1461

<210> SEQ ID NO 2
<211> LENGTH: 486
<212> TYPE: PRT
<213> ORGANISM: Staphylococcus bacteriophage 2638A

<400> SEQUENCE: 2

Met Leu Thr Ala Ile Asp Tyr Leu Thr Lys Lys Gly Trp Lys Ile Ser
1               5                   10                  15

Ser Asp Pro Arg Thr Tyr Asp Gly Tyr Pro Lys Asn Tyr Gly Tyr Arg
            20                  25                  30

Asn Tyr His Glu Asn Gly Ile Asn Tyr Asp Glu Phe Cys Gly Gly Tyr
        35                  40                  45

His Arg Ala Phe Asp Val Tyr Ser Asn Glu Thr Asn Asp Val Pro Ala
    50                  55                  60

Val Thr Ser Gly Thr Val Ile Glu Ala Asn Asp Tyr Gly Asn Phe Gly
65                  70                  75                  80

Gly Thr Phe Val Ile Arg Asp Ala Asn Asp Asn Asp Trp Ile Tyr Gly
                85                  90                  95

His Leu Gln Arg Gly Ser Met Arg Phe Val Val Gly Asp Lys Val Asn
            100                 105                 110
```

Gln Gly Asp Ile Ile Gly Leu Gln Gly Asn Ser Asn Tyr Tyr Asp Asn
            115                 120                 125

Pro Met Ser Val His Leu His Leu Gln Leu Arg Pro Lys Asp Ala Lys
        130                 135                 140

Lys Asp Glu Lys Ser Gln Val Cys Ser Gly Leu Ala Met Glu Lys Tyr
145                 150                 155                 160

Asp Ile Thr Asn Leu Asn Ala Lys Gln Asp Lys Ser Lys Asn Gly Ser
                165                 170                 175

Val Lys Glu Leu Lys His Ile Tyr Ser Asn His Ile Lys Gly Asn Lys
            180                 185                 190

Ile Thr Ala Pro Lys Pro Ser Ile Gln Gly Val Ile His Asn Asp
        195                 200                 205

Tyr Gly Ser Met Thr Pro Ser Gln Tyr Leu Pro Trp Leu Tyr Ala Arg
        210                 215                 220

Glu Asn Asn Gly Thr His Val Asn Gly Trp Ala Ser Val Tyr Ala Asn
225                 230                 235                 240

Arg Asn Glu Val Leu Trp Tyr His Pro Thr Asp Tyr Val Glu Trp His
                245                 250                 255

Cys Gly Asn Gln Trp Ala Asn Ala Asn Leu Ile Gly Phe Glu Val Cys
            260                 265                 270

Glu Ser Tyr Pro Gly Arg Ile Ser Asp Lys Leu Phe Leu Glu Asn Glu
        275                 280                 285

Glu Ala Thr Leu Lys Val Ala Ala Asp Val Met Lys Ser Tyr Gly Leu
        290                 295                 300

Pro Val Asn Arg Asn Thr Val Arg Leu His Asn Glu Phe Phe Gly Thr
305                 310                 315                 320

Ser Cys Pro His Arg Ser Trp Asp Leu His Val Gly Lys Gly Glu Pro
                325                 330                 335

Tyr Thr Thr Thr Asn Ile Asn Lys Met Lys Asp Tyr Phe Ile Lys Arg
            340                 345                 350

Ile Lys His Tyr Tyr Asp Gly Gly Lys Leu Glu Val Ser Lys Ala Ala
        355                 360                 365

Thr Ile Lys Gln Ser Asp Val Lys Gln Glu Val Lys Gln Glu Ala
        370                 375                 380

Lys Gln Ile Val Lys Ala Thr Asp Trp Lys Gln Asn Lys Asp Gly Ile
385                 390                 395                 400

Trp Tyr Lys Ala Glu His Ala Ser Phe Thr Val Thr Ala Pro Glu Gly
                405                 410                 415

Ile Ile Thr Arg Tyr Lys Gly Pro Trp Thr Gly His Pro Gln Ala Gly
            420                 425                 430

Val Leu Gln Lys Gly Gln Thr Ile Lys Tyr Asp Glu Val Gln Lys Phe
        435                 440                 445

Asp Gly His Val Trp Val Ser Trp Glu Thr Phe Glu Gly Glu Thr Val
        450                 455                 460

Tyr Met Pro Val Arg Thr Trp Asp Ala Lys Thr Gly Lys Val Gly Lys
465                 470                 475                 480

Leu Trp Gly Glu Ile Lys
            485

<210> SEQ ID NO 3
<211> LENGTH: 279
<212> TYPE: DNA
<213> ORGANISM: Staphylococcus simulans

<400> SEQUENCE: 3

```
tggaaaacaa acaaatatgg cacactatat aaatcagagt cagctagctt cacacctaat      60
acagatataa taacaagaac gactggtcca tttagaagca tgccgcagtc aggagtctta     120
aaagcaggtc aaacaattca ttatgatgaa gtgatgaaac aagacggtca tgtttgggta     180
ggttatacag gtaacagtgg ccaacgtatt tacttgcctg taagaacatg gaataaatct     240
actaatactt taggtgttct ttggggaact ataaagtga                            279
```

<210> SEQ ID NO 4
<211> LENGTH: 92
<212> TYPE: PRT
<213> ORGANISM: Staphylococcus simulans

<400> SEQUENCE: 4

```
Trp Lys Thr Asn Lys Tyr Gly Thr Leu Tyr Lys Ser Glu Ser Ala Ser
1               5                   10                  15

Phe Thr Pro Asn Thr Asp Ile Ile Thr Arg Thr Thr Gly Pro Phe Arg
                20                  25                  30

Ser Met Pro Gln Ser Gly Val Leu Lys Ala Gly Gln Thr Ile His Tyr
            35                  40                  45

Asp Glu Val Met Lys Gln Asp Gly His Val Trp Val Gly Tyr Thr Gly
        50                  55                  60

Asn Ser Gly Gln Arg Ile Tyr Leu Pro Val Arg Thr Trp Asn Lys Ser
65                  70                  75                  80

Thr Asn Thr Leu Gly Val Leu Trp Gly Thr Ile Lys
                85                  90
```

<210> SEQ ID NO 5
<211> LENGTH: 285
<212> TYPE: DNA
<213> ORGANISM: Staphylococcus bacteriophage 2638A

<400> SEQUENCE: 5

```
tggaaacaga ataaagatgg catttggtat aaagctgaac atgcttcgtt cacagtgaca      60
gcaccagagg gaattatcac aagatacaaa ggtccttgga ctggtcaccc acaagctggt     120
gtattacaaa aaggtcaaac gattaaatat gatgaggttc aaaaatttga cggtcatgtt     180
tgggtatcgt gggaaacgtt tgagggcgaa actgtataca tgccggtacg cacatgggac     240
gctaaaactg gtaagttggg taagttgtgg ggcgaaatta aataa                     285
```

<210> SEQ ID NO 6
<211> LENGTH: 94
<212> TYPE: PRT
<213> ORGANISM: Staphylococcus bacteriophage 2638A

<400> SEQUENCE: 6

```
Trp Lys Gln Asn Lys Asp Gly Ile Trp Tyr Lys Ala Glu His Ala Ser
1               5                   10                  15

Phe Thr Val Thr Ala Pro Glu Gly Ile Ile Thr Arg Tyr Lys Gly Pro
                20                  25                  30

Trp Thr Gly His Pro Gln Ala Gly Val Leu Gln Lys Gly Gln Thr Ile
            35                  40                  45

Lys Tyr Asp Glu Val Gln Lys Phe Asp Gly His Val Trp Val Ser Trp
        50                  55                  60

Glu Thr Phe Glu Gly Glu Thr Val Tyr Met Pro Val Arg Thr Trp Asp
65                  70                  75                  80
```

Ala Lys Thr Gly Lys Val Gly Lys Leu Trp Gly Glu Ile Lys
            85                  90

<210> SEQ ID NO 7
<211> LENGTH: 282
<212> TYPE: DNA
<213> ORGANISM: Staphylococcus bacteriophage phiNM3

<400> SEQUENCE: 7
ggtaaatctg caagtaaaat aacagttgga agtaaagcgc cttataacct taaatggtca    60
aaaggtgctt attttaatgc gaaaatcgac ggcttaggtg ctacttcagc cactagatac   120
ggtgataatc gtactaacta tagattcgat gttggacagg ctgtatacgc gcctggaaca   180
ttaatatatg tgtttgaaat tatagatggt tggtgtcgca tttattggaa caatcataat   240
gagtggatat ggcatgagag attgattgtg aaagaagtgt tt                      282

<210> SEQ ID NO 8
<211> LENGTH: 94
<212> TYPE: PRT
<213> ORGANISM: Staphylococcus bacteriophage phiNM3

<400> SEQUENCE: 8

Gly Lys Ser Ala Ser Lys Ile Thr Val Gly Ser Lys Ala Pro Tyr Asn
1               5                   10                  15

Leu Lys Trp Ser Lys Gly Ala Tyr Phe Asn Ala Lys Ile Asp Gly Leu
            20                  25                  30

Gly Ala Thr Ser Ala Thr Arg Tyr Gly Asp Asn Arg Thr Asn Tyr Arg
        35                  40                  45

Phe Asp Val Gly Gln Ala Val Tyr Ala Pro Gly Thr Leu Ile Tyr Val
    50                  55                  60

Phe Glu Ile Ile Asp Gly Trp Cys Arg Ile Tyr Trp Asn Asn His Asn
65                  70                  75                  80

Glu Trp Ile Trp His Glu Arg Leu Ile Val Lys Glu Val Phe
            85                  90

<210> SEQ ID NO 9
<211> LENGTH: 585
<212> TYPE: DNA
<213> ORGANISM: Staphylococcus bacteriophage K

<400> SEQUENCE: 9
atggctaaga ctcaagcaga aataaataaa cgtttagatg cttatgcaaa aggaacagta    60
gatagccctt acagagttaa aaaagctaca agttatgacc catcatttgg tgtaatggaa   120
gcaggagcca ttgatgcaga tggttactat cacgctcagt gtcaagacct tattacagac   180
tatgttttat ggttaacaga taataaagtt agaacttggg gtaatgctaa agaccaaatt   240
aaacagagtt atggtactgg atttaaaata catgaaaata aaccttctac tgtacctaaa   300
aaaggttgga ttgcggtatt tacatccggt agttatgaac agtggggtca taggtatt   360 gtatatgatg gaggtaatac ttctacattt actattttag agcaaaactg gaatggttat   420
gctaataaaa aacctacaaa acgtgtagat aattattacg gattaactca cttcattgaa   480
atacctgtaa aagcaggaac tactgttaaa aaagaaacag ctaagaaaag cgcaagtaaa   540
acgcctgcac ctaaaaagaa agcaacacta aagtttcta agaat              585

<210> SEQ ID NO 10
<211> LENGTH: 195
<212> TYPE: PRT

<213> ORGANISM: Staphylococcus bacteriophage K

<400> SEQUENCE: 10

```
Met Ala Lys Thr Gln Ala Glu Ile Asn Lys Arg Leu Asp Ala Tyr Ala
1               5                   10                  15
Lys Gly Thr Val Asp Ser Pro Tyr Arg Val Lys Ala Thr Ser Tyr
            20                  25                  30
Asp Pro Ser Phe Gly Val Met Glu Ala Gly Ala Ile Asp Ala Asp Gly
        35                  40                  45
Tyr Tyr His Ala Gln Cys Gln Asp Leu Ile Thr Asp Tyr Val Leu Trp
    50                  55                  60
Leu Thr Asp Asn Lys Val Arg Thr Trp Gly Asn Ala Lys Asp Gln Ile
65                  70                  75                  80
Lys Gln Ser Tyr Gly Thr Gly Phe Lys Ile His Glu Asn Lys Pro Ser
                85                  90                  95
Thr Val Pro Lys Lys Gly Trp Ile Ala Val Phe Thr Ser Gly Ser Tyr
            100                 105                 110
Glu Gln Trp Gly His Ile Gly Ile Val Tyr Asp Gly Gly Asn Thr Ser
        115                 120                 125
Thr Phe Thr Ile Leu Glu Gln Asn Trp Asn Gly Tyr Ala Asn Lys Lys
    130                 135                 140
Pro Thr Lys Arg Val Asp Asn Tyr Tyr Gly Leu Thr His Phe Ile Glu
145                 150                 155                 160
Ile Pro Val Lys Ala Gly Thr Thr Val Lys Lys Glu Thr Ala Lys Lys
                165                 170                 175
Ser Ala Ser Lys Thr Pro Ala Pro Lys Lys Ala Thr Leu Lys Val
            180                 185                 190
Ser Lys Asn
        195
```

<210> SEQ ID NO 11
<211> LENGTH: 420
<212> TYPE: DNA
<213> ORGANISM: Staphylococcus bacteriophage Twort

<400> SEQUENCE: 11

```
atgaaaaccc tgaaacaagc agagtcctac attaagagta agtaaatac aggaactgat      60
tttgatggtt tatatgggta tcagtgtatg gacttagcag tagattatat ttaccatgta    120
acagatggta aaataagaat gtggggtaat gctaaggatg cgataaataa ctcttttggt    180
ggtactgcta cggtatataa aaactaccct gcttttagac ctaagtacgg tgatgtagtc    240
gtatggacta ctggtaattt tgcaacttat ggtcatatcg caatagttac taaccctgac    300
ccttatggag accttcaata tgttacagtt cttgaacaaa actggaacgg taacgggatt    360
tataaaaccg agttagctac aatcagaaca cacgattaca caggaattac acattttatt    420
```

<210> SEQ ID NO 12
<211> LENGTH: 140
<212> TYPE: PRT
<213> ORGANISM: Staphylococcus bacteriophage Twort

<400> SEQUENCE: 12

```
Met Lys Thr Leu Lys Gln Ala Glu Ser Tyr Ile Lys Ser Lys Val Asn
1               5                   10                  15
Thr Gly Thr Asp Phe Asp Gly Leu Tyr Gly Tyr Gln Cys Met Asp Leu
            20                  25                  30
```

Ala Val Asp Tyr Ile Tyr His Val Thr Asp Gly Lys Ile Arg Met Trp
         35                  40                  45

Gly Asn Ala Lys Asp Ala Ile Asn Asn Ser Phe Gly Gly Thr Ala Thr
 50                  55                  60

Val Tyr Lys Asn Tyr Pro Ala Phe Arg Pro Lys Tyr Gly Asp Val Val
 65                  70                  75                  80

Val Trp Thr Thr Gly Asn Phe Ala Thr Tyr Gly His Ile Ala Ile Val
                 85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile
        130                 135                 140

<210> SEQ ID NO 13
<211> LENGTH: 438
<212> TYPE: DNA
<213> ORGANISM: Staphylococcus bacteriophage 2638A

<400> SEQUENCE: 13
atgctaactg ctattgacta tcttacgaaa aaaggttgga aaatatcatc tgaccctcgc      60
acttacgatg gttaccctaa aaactacggc tacagaaatt accatgaaaa cggcattaat     120
tatgatgagt tttgtggtgg ttatcataga gcttttgatg tttacagtaa cgaaactaac     180
gacgtgcctg ctgttactag cggaacagtt attgaagcaa acgattacgg taattttggt     240
ggtacattcg ttattagaga cgctaacgat aacgattgga tatatgggca tctacaacgt     300
ggctcaatgc gatttgttgt aggcgacaaa gtcaatcaag gtgacattat tggtttacaa     360
ggtaatagca actattacga caatcctatg agtgtacatt tacatttaca attacgccct     420
aaagacgcaa agaaagat                                                    438

<210> SEQ ID NO 14
<211> LENGTH: 146
<212> TYPE: PRT
<213> ORGANISM: Staphylococcus bacteriophage 2638A

<400> SEQUENCE: 14

Met Leu Thr Ala Ile Asp Tyr Leu Thr Lys Lys Gly Trp Lys Ile Ser
 1               5                  10                  15

Ser Asp Pro Arg Thr Tyr Asp Gly Tyr Pro Lys Asn Tyr Gly Tyr Arg
             20                  25                  30

Asn Tyr His Glu Asn Gly Ile Asn Tyr Asp Glu Phe Cys Gly Gly Tyr
         35                  40                  45

His Arg Ala Phe Asp Val Tyr Ser Asn Glu Thr Asn Asp Val Pro Ala
 50                  55                  60

Val Thr Ser Gly Thr Val Ile Glu Ala Asn Asp Tyr Gly Asn Phe Gly
 65                  70                  75                  80

Gly Thr Phe Val Ile Arg Asp Ala Asn Asp Asn Asp Trp Ile Tyr Gly
                 85                  90                  95

His Leu Gln Arg Gly Ser Met Arg Phe Val Val Gly Asp Lys Val Asn
            100                 105                 110

Gln Gly Asp Ile Ile Gly Leu Gln Gly Asn Ser Asn Tyr Tyr Asp Asn
        115                 120                 125

Pro Met Ser Val His Leu His Leu Gln Leu Arg Pro Lys Asp Ala Lys
        130                 135                 140

<210> SEQ ID NO 15
<211> LENGTH: 420
<212> TYPE: DNA
<213> ORGANISM: Staphylococcus simulans

<400> SEQUENCE: 15

```
gctgcaacac atgaacattc agcacaatgg ttgaataatt acaaaaaagg atatggttac      60
ggtccttatc cattaggtat aaatggcggt atgcactacg gagttgattt ttttatgaat     120
attggaacac cagtaaaagc tatttcaagc ggaaaaatag ttgaagctgg ttggagtaat     180
tacggaggag gtaatcaaat aggtcttatt gaaaatgatg gagtgcatag acaatggtat     240
atgcatctaa gtaaatataa tgttaaagta ggagattatg tcaaagctgg tcaaataatc     300
ggttggtctg gaagcactgg ttattctaca gcaccacatt tacacttcca aagaatggtt     360
aattcatttt caaattcaac tgcccaagat ccaatgcctt tcttaaagag cgcaggatat     420
```

<210> SEQ ID NO 16
<211> LENGTH: 140
<212> TYPE: PRT
<213> ORGANISM: Staphylococcus simulans

<400> SEQUENCE: 16

```
Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Ser Phe Ser Asn Ser Thr Ala
        115                 120                 125

Gln Asp Pro Met Pro Phe Leu Lys Ser Ala Gly Tyr
    130                 135                 140
```

<210> SEQ ID NO 17
<211> LENGTH: 510
<212> TYPE: DNA
<213> ORGANISM: Staphylococcus bacteriophage 2638A

<400> SEQUENCE: 17

```
ggtaacaaga ttacagcacc aaaacctagt attcaaggtg tggtcatcca caatgattat      60
ggtagtatga cacctagtca atacttacca tggttatatg cacgtgagaa taacggtaca     120
cacgttaacg gttgggctag tgtttatgca aatagaaacg aagtgctttg gtatcatccg     180
acagactacg tagagtggca ttgtggtaat caatgggcaa atgctaactt aatcggattt     240
gaagtgtgtg agtcgtatcc tggtagaatc tcggacaaat tattcttaga aaatgaagaa     300
```

```
gcgacattga aagtagctgc ggatgtgatg aagtcgtacg gattaccagt taatcgcaac    360
actgtacgtc tgcataacga attcttcgga acttcttgtc cacatcgttc gtgggacttg    420
catgttggca aaggtgagcc ttacacaact actaatatta ataaaatgaa agactacttc    480
atcaaacgca tcaaacatta ttatgacggt                                      510

<210> SEQ ID NO 18
<211> LENGTH: 169
<212> TYPE: PRT
<213> ORGANISM: Staphylococcus bacteriophage 2638A

<400> SEQUENCE: 18
```

Asn Lys Ile Thr Ala Pro Lys Pro Ser Ile Gln Gly Val Val Ile His
1               5                   10                  15

Asn Asp Tyr Gly Ser Met Thr Pro Ser Gln Tyr Leu Pro Trp Leu Tyr
            20                  25                  30

Ala Arg Glu Asn Asn Gly Thr His Val Asn Gly Trp Ala Ser Val Tyr
        35                  40                  45

Ala Asn Arg Asn Glu Val Leu Trp Tyr His Pro Thr Asp Tyr Val Glu
    50                  55                  60

Trp His Cys Gly Asn Gln Trp Ala Asn Ala Asn Leu Ile Gly Phe Glu
65                  70                  75                  80

Val Cys Glu Ser Tyr Pro Gly Arg Ile Ser Asp Lys Leu Phe Leu Glu
                85                  90                  95

Asn Glu Glu Ala Thr Leu Lys Val Ala Ala Asp Val Met Lys Ser Tyr
            100                 105                 110

Gly Leu Pro Val Asn Arg Asn Thr Val Arg Leu His Asn Glu Phe Phe
        115                 120                 125

Gly Thr Ser Cys Pro His Arg Ser Trp Asp Leu His Val Gly Lys Gly
    130                 135                 140

Glu Pro Tyr Thr Thr Thr Asn Ile Asn Lys Met Lys Asp Tyr Phe Ile
145                 150                 155                 160

Lys Arg Ile Lys His Tyr Tyr Asp Gly
                165

```
<210> SEQ ID NO 19
<211> LENGTH: 1407
<212> TYPE: DNA
<213> ORGANISM: artificial
<220> FEATURE:
<223> OTHER INFORMATION: artificial construct

<400> SEQUENCE: 19
atggctaaga ctcaagcaga aataaataaa cgtttagatg cttatgcaaa aggaacagta     60
gatagcccct tacagagttaa aaaagctaca agttatgacc catcatttgg tgtaatggaa   120
gcaggagcca ttgatgcaga tggttactat cacgctcagt gtcaagacct tattacagac   180
tatgttttat ggttaacaga taataaagtt agaacttggg gtaatgctaa agaccaaatt   240
aaacagagtt atggtactgg atttaaaata catgaaaata aaccttctac tgtacctaaa   300
aaaggttgga ttgcggtatt tacatccggt agttatgaac agtggggtca cataggtatt   360
gtatatgatg gaggtaatac ttctacattt actattttag agcaaaactg gaatggttat   420
gctaataaaa aacctacaaa acgtgtagat aattattacg gattaactca cttcattgaa   480
atacctgtaa aagcaggaac tactgttaaa aagaaacag ctaagaaaag cgcaagtaaa   540
acgcctgcac ctaaaaagaa agcaacacta aaagtttcta gaatgagct catggctaag   600

```
actcaagcag aaataaataa acgtttagat gcttatgcaa aaggaacagt agatagccct       660
tacagagtta aaaaagctac aagttatgac ccatcatttg gtgtaatgga agcaggagcc       720
attgatgcag atggttacta tcacgctcag tgtcaagacc ttattacaga ctatgtttta       780
tggttaacag ataataaagt tagaacttgg ggtaatgcta agaccaaat taaacagagt       840 tatggtactg gatttaaaat acatgaaaat aaaccttcta ctgtacctaa aaaaggttgg       900
attgcggtat ttcatccgg tagttatgaa cagtggggtc acataggtat tgtatatgat       960
ggaggtaata cttctacatt tactatttta gagcaaaact ggaatggtta tgctaataaa      1020
aaacctacaa aacgtgtaga taattattac ggattaactc acttcattga atacctgta       1080 aaagcaggaa aagcaggtgg tacagtaact ccaacgccga atacaggttg aaaacaaac      1140 aaatatggca cactatataa atcagagtca gctagcttca cacctaatac agatataata      1200
acaagaacga ctggtccatt tagaagcatg ccgcagtcag gagtcttaaa agcaggtcaa      1260
acaattcatt atgatgaagt gatgaaacaa gacggtcatg tttgggtagg ttatacaggt      1320
aacagtggcc aacgtattta cttgcctgta agaacatgga ataaatctac taatacttta      1380
ggtgttcttt ggggaactat aaagtaa                                          1407

<210> SEQ ID NO 20
<211> LENGTH: 468
<212> TYPE: PRT
<213> ORGANISM: artificial
<220> FEATURE:
<223> OTHER INFORMATION: artificial construct

<400> SEQUENCE: 20

Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
                20                  25                  30

Asp Pro Ser Phe Gly Val Met Glu Ala Gly Ala Ile Asp Ala Asp Gly
            35                  40                  45

Tyr Tyr His Ala Gln Cys Gln Asp Leu Ile Thr Asp Tyr Val Leu Trp
        50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
    130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Ala Thr Leu Lys Val
            180                 185                 190

Ser Lys Asn Glu Leu Met Ala Lys Thr Gln Ala Glu Ile Asn Lys Arg
        195                 200                 205

Leu Asp Ala Tyr Ala Lys Gly Thr Val Asp Ser Pro Tyr Arg Val Lys
    210                 215                 220
```

Lys Ala Thr Ser Tyr Asp Pro Ser Phe Gly Val Met Glu Ala Gly Ala
225                 230                 235                 240

Ile Asp Ala Asp Gly Tyr Tyr His Ala Gln Cys Gln Asp Leu Ile Thr
            245                 250                 255

Asp Tyr Val Leu Trp Leu Thr Asp Asn Lys Val Arg Thr Trp Gly Asn
        260                 265                 270

Ala Lys Asp Gln Ile Lys Gln Ser Tyr Gly Thr Gly Phe Lys Ile His
    275                 280                 285

Glu Asn Lys Pro Ser Thr Val Pro Lys Lys Gly Trp Ile Ala Val Phe
290                 295                 300

Thr Ser Gly Ser Tyr Glu Gln Trp Gly His Ile Gly Ile Val Tyr Asp
305                 310                 315                 320

Gly Gly Asn Thr Ser Thr Phe Thr Ile Leu Glu Gln Asn Trp Asn Gly
            325                 330                 335

Tyr Ala Asn Lys Lys Pro Thr Lys Arg Val Asp Asn Tyr Tyr Gly Leu
        340                 345                 350

Thr His Phe Ile Glu Ile Pro Val Lys Ala Gly Lys Ala Gly Gly Thr
    355                 360                 365

Val Thr Pro Thr Pro Asn Thr Gly Trp Lys Thr Asn Lys Tyr Gly Thr
370                 375                 380

Leu Tyr Lys Ser Glu Ser Ala Ser Phe Thr Pro Asn Thr Asp Ile Ile
385                 390                 395                 400

Thr Arg Thr Thr Gly Pro Phe Arg Ser Met Pro Gln Ser Gly Val Leu
            405                 410                 415

Lys Ala Gly Gln Thr Ile His Tyr Asp Glu Val Met Lys Gln Asp Gly
        420                 425                 430

His Val Trp Val Gly Tyr Thr Gly Asn Ser Gly Gln Arg Ile Tyr Leu
    435                 440                 445

Pro Val Arg Thr Trp Asn Lys Ser Thr Asn Thr Leu Gly Val Leu Trp
450                 455                 460

Gly Thr Ile Lys
465

<210> SEQ ID NO 21
<211> LENGTH: 1209
<212> TYPE: DNA
<213> ORGANISM: artificial
<220> FEATURE:
<223> OTHER INFORMATION: artificial construct

<400> SEQUENCE: 21
gctgcaacac atgaacattc agcacaatgg ttgaataatt acaaaaaagg atatggttac      60
ggtccttatc cattaggtat aaatggcggt atgcactacg gagttgattt ttttatgaat     120
attggaacac cagtaaaagc tatttcaagc ggaaaaatag ttgaagctgg ttggagtaat     180
tacggaggag gtaatcaaat aggtcttatt gaaaatgatg gagtgcatag acaatggtat     240
atgcatctaa gtaaatataa tgttaaagta ggagattatg tcaaagctgg tcaaataatc     300
ggttggtctg gaagcactgg ttattctaca gcaccacatt tacacttcca agaatggtt      360 aattcatttt caaattcaac tgcccaagat ccatgccctt tcttaaagag cgcaggatat     420
ggaaaagcag gtggtacagt aactccaacg ccgaatacag gtgagctcgc tgcaacacat     480
gaacattcag cacaatggtt gaataattac aaaaaaggat atggttacgg tccttatcca     540
ttaggtataa atggcggtat gcactacgga gttgattttt tatgaatat tggaacacca     600

```
gtaaaagcta tttcaagcgg aaaaatagtt gaagctggtt ggagtaatta cggaggaggt    660
aatcaaatag gtcttattga aaatgatgga gtgcatagac aatggtatat gcatctaagt    720
aaatataatg ttaaagtagg agattatgtc aaagctggtc aaataatcgg ttggtctgga    780
agcactggtt attctacagc accacattta cacttccaaa gaatggttaa ttcatttca    840 aattcaactg cccaagatcc aatgccttc ttaaagagcg caggatatgg aaaagcaggt    900
ggtacagtaa ctccaacgcc gaatacaggt tggaaaacaa acaaatatgg cacactatat    960
aaatcagagt cagctagctt cacacctaat acagatataa taacaagaac gactggtcca   1020
tttagaagca tgccgcagtc aggagtctta aaagcaggtc aaacaattca ttatgatgaa   1080
gtgatgaaac aagacggtca tgtttgggta ggttatacag gtaacagtgg ccaacgtatt   1140
tacttgcctg taagaacatg gaataaatct actaatactt taggtgttct ttggggaact   1200
ataaagtaa                                                           1209
```

<210> SEQ ID NO 22
<211> LENGTH: 402
<212> TYPE: PRT
<213> ORGANISM: artificial
<220> FEATURE:
<223> OTHER INFORMATION: artificial construct

<400> SEQUENCE: 22

```
Ala Ala Thr His Glu His Ser Ala Gln Trp Leu Asn Asn Tyr Lys Lys
 1               5                  10                  15

Gly Tyr Gly Tyr Gly Pro Tyr Pro Leu Gly Ile Asn Gly Gly Met His
                20                  25                  30

Tyr Gly Val Asp Phe Phe Met Asn Ile Gly Thr Pro Val Lys Ala Ile
            35                  40                  45

Ser Ser Gly Lys Ile Val Glu Ala Gly Trp Ser Asn Tyr Gly Gly Gly
        50                  55                  60

Asn Gln Ile Gly Leu Ile Glu Asn Asp Gly Val His Arg Gln Trp Tyr
 65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Ser Phe Ser Asn Ser Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Glu Leu Ala Ala Thr His
145                 150                 155                 160

Glu His Ser Ala Gln Trp Leu Asn Asn Tyr Lys Lys Gly Tyr Gly Tyr
                165                 170                 175

Gly Pro Tyr Pro Leu Gly Ile Asn Gly Gly Met His Tyr Gly Val Asp
            180                 185                 190

Phe Phe Met Asn Ile Gly Thr Pro Val Lys Ala Ile Ser Ser Gly Lys
        195                 200                 205

Ile Val Glu Ala Gly Trp Ser Asn Tyr Gly Gly Gly Asn Gln Ile Gly
    210                 215                 220

Leu Ile Glu Asn Asp Gly Val His Arg Gln Trp Tyr Met His Leu Ser
225                 230                 235                 240

Lys Tyr Asn Val Lys Val Gly Asp Tyr Val Lys Ala Gly Gln Ile Ile
                245                 250                 255
```

Gly Trp Ser Gly Ser Thr Gly Tyr Ser Thr Ala Pro His Leu His Phe
            260                 265                 270

Gln Arg Met Val Asn Ser Phe Ser Asn Ser Thr Ala Gln Asp Pro Met
        275                 280                 285

Pro Phe Leu Lys Ser Ala Gly Tyr Gly Lys Ala Gly Gly Thr Val Thr
    290                 295                 300

Pro Thr Pro Asn Thr Gly Trp Lys Thr Asn Lys Tyr Gly Thr Leu Tyr
305                 310                 315                 320

Lys Ser Glu Ser Ala Ser Phe Thr Pro Asn Thr Asp Ile Ile Thr Arg
                325                 330                 335

Thr Thr Gly Pro Phe Arg Ser Met Pro Gln Ser Gly Val Leu Lys Ala
            340                 345                 350

Gly Gln Thr Ile His Tyr Asp Glu Val Met Lys Gln Asp Gly His Val
        355                 360                 365

Trp Val Gly Tyr Thr Gly Asn Ser Gly Gln Arg Ile Tyr Leu Pro Val
    370                 375                 380

Arg Thr Trp Asn Lys Ser Thr Asn Thr Leu Gly Val Leu Trp Gly Thr
385                 390                 395                 400

Ile Lys

<210> SEQ ID NO 23
<211> LENGTH: 1686
<212> TYPE: DNA
<213> ORGANISM: artificial
<220> FEATURE:
<223> OTHER INFORMATION: artificial construct

<400> SEQUENCE: 23
gcaaagaaag atgaaaaatc acaagtatgt agtggtttgg ctatggaaaa atatgacatt      60
acaaatttaa atgctaaaca agataaatca agaatgggga gcgtgaaaga gttgaaacat     120
atctattcaa accatattaa aggtaacaag attacagcac caaaacctag tattcaaggt     180
gtggtcatcc acaatgatta tggtagtatg acacctagtc aatacttacc atggttatat     240
gcacgtgaga ataacggtac acacgttaac ggttgggcta gtgtttatgc aaatagaaac     300
gaagtgcttt ggtatcatcc gacagactac gtagagtggc attgtggtaa tcaatgggca     360
aatgctaact taatcggatt tgaagtgtgt gagtcgtatc ctggtagaat ctcggacaaa     420
ttattcttag aaaatgaaga agcgacattg aaagtagctg cggatgtgat gaagtcgtac     480
ggattaccag ttaatcgcaa cactgtacgt ctgcataacg aattcttcgg aacttcttgt     540
ccacatcgtt cgtgggactt gcatgttggc aaaggtgagc cttacacaac tactaatatt     600
aataaaatga agactactt catcaaacgc atcaaacatt attatgacgg tgagctcgca     660
aagaaagatg aaaaatcaca gtatgtagt ggtttggcta tggaaaaata tgacattaca     720
aatttaaatg ctaaacaaga taatcaaag aatgggagcg tgaaagagtt gaaacatatc     780
tattcaaacc atattaaagg taacaagatt acagcaccaa aacctagtat tcaaggtgtg     840
gtcatccaca tgattatgg tagtatgaca cctagtcaat acttaccatg gttatatgca     900
cgtgagaata acggtacaca cgttaacggt tgggctagtg tttatgcaaa tagaaacgaa     960
gtgctttggt atcatccgac agactacgta gagtggcatt gtggtaatca atgggcaaat    1020
gctaacttaa tcggatttga agtgtgtgag tcgtatcctg gtagaatctc ggacaaatta    1080
ttcttagaaa atgaagaagc gacattgaaa gtagctgcgg atgtgatgaa gtcgtacgga    1140
ttaccagtta atcgcaacac tgtacgtctg cataacgaat tcttcggaac ttcttgtcca    1200

-continued

```
catcgttcgt gggacttgca tgttggcaaa ggtgagcctt acacaactac taatattaat    1260
aaaatgaaag actacttcat caaacgcatc aaacattatt atgacggtgg aaagctagaa    1320
gtaagcaaag cagcaactat caaacaatct gacgttaagc aagaagttaa aaagcaagaa    1380 gcaaacaaa ttgtgaaagc aacagattgg aaaacaaaca aatatggcac actatataaa     1440
tcagagtcag ctagcttcac acctaataca gatataataa caagaacgac tggtccattt    1500
agaagcatgc cgcagtcagg agtcttaaaa gcaggtcaaa caattcatta tgatgaagtg    1560
atgaaacaag acggtcatgt ttgggtaggt tatacaggta acagtggcca acgtatttac    1620
ttgcctgtaa aacatggaa taaatctact aatactttag gtgttctttg gggaactata    1680
aagtaa                                                                1686
```

<210> SEQ ID NO 24
<211> LENGTH: 561
<212> TYPE: PRT
<213> ORGANISM: artificial
<220> FEATURE:
<223> OTHER INFORMATION: artificial construct

<400> SEQUENCE: 24

```
Ala Lys Lys Asp Glu Lys Ser Gln Val Cys Ser Gly Leu Ala Met Glu
1               5                   10                  15

Lys Tyr Asp Ile Thr Asn Leu Asn Ala Lys Gln Asp Lys Ser Lys Asn
            20                  25                  30

Gly Ser Val Lys Glu Leu Lys His Ile Tyr Ser Asn His Ile Lys Gly
        35                  40                  45

Asn Lys Ile Thr Ala Pro Lys Pro Ser Ile Gln Gly Val Val Ile His
    50                  55                  60

Asn Asp Tyr Gly Ser Met Thr Pro Ser Gln Tyr Leu Pro Trp Leu Tyr
65                  70                  75                  80

Ala Arg Glu Asn Asn Gly Thr His Val Asn Gly Trp Ala Ser Val Tyr
                85                  90                  95

Ala Asn Arg Asn Glu Val Leu Trp Tyr His Pro Thr Asp Tyr Val Glu
            100                 105                 110

Trp His Cys Gly Asn Gln Trp Ala Asn Ala Asn Leu Ile Gly Phe Glu
        115                 120                 125

Val Cys Glu Ser Tyr Pro Gly Arg Ile Ser Asp Lys Leu Phe Leu Glu
    130                 135                 140

Asn Glu Glu Ala Thr Leu Lys Val Ala Ala Asp Val Met Lys Ser Tyr
145                 150                 155                 160

Gly Leu Pro Val Asn Arg Asn Thr Val Arg Leu His Asn Glu Phe Phe
                165                 170                 175

Gly Thr Ser Cys Pro His Arg Ser Trp Asp Leu His Val Gly Lys Gly
            180                 185                 190

Glu Pro Tyr Thr Thr Thr Asn Ile Asn Lys Met Lys Asp Tyr Phe Ile
        195                 200                 205

Lys Arg Ile Lys His Tyr Tyr Asp Gly Glu Leu Ala Lys Lys Asp Glu
    210                 215                 220

Lys Ser Gln Val Cys Ser Gly Leu Ala Met Glu Lys Tyr Asp Ile Thr
225                 230                 235                 240

Asn Leu Asn Ala Lys Gln Asp Lys Ser Lys Asn Gly Ser Val Lys Glu
                245                 250                 255

Leu Lys His Ile Tyr Ser Asn His Ile Lys Gly Asn Lys Ile Thr Ala
            260                 265                 270
```

```
Pro Lys Pro Ser Ile Gln Gly Val Val Ile His Asn Asp Tyr Gly Ser
        275                 280                 285

Met Thr Pro Ser Gln Tyr Leu Pro Trp Leu Tyr Ala Arg Glu Asn Asn
    290                 295                 300

Gly Thr His Val Asn Gly Trp Ala Ser Val Tyr Ala Asn Arg Asn Glu
305                 310                 315                 320

Val Leu Trp Tyr His Pro Thr Asp Tyr Val Glu Trp His Cys Gly Asn
                325                 330                 335

Gln Trp Ala Asn Ala Asn Leu Ile Gly Phe Glu Val Cys Glu Ser Tyr
            340                 345                 350

Pro Gly Arg Ile Ser Asp Lys Leu Phe Leu Glu Asn Glu Glu Ala Thr
        355                 360                 365

Leu Lys Val Ala Ala Asp Val Met Lys Ser Tyr Gly Leu Pro Val Asn
    370                 375                 380

Arg Asn Thr Val Arg Leu His Asn Glu Phe Phe Gly Thr Ser Cys Pro
385                 390                 395                 400

His Arg Ser Trp Asp Leu His Val Gly Lys Gly Glu Pro Tyr Thr Thr
                405                 410                 415

Thr Asn Ile Asn Lys Met Lys Asp Tyr Phe Ile Lys Arg Ile Lys His
            420                 425                 430

Tyr Tyr Asp Gly Gly Lys Leu Glu Val Ser Lys Ala Ala Thr Ile Lys
        435                 440                 445

Gln Ser Asp Val Lys Gln Glu Val Lys Lys Gln Glu Ala Lys Gln Ile
    450                 455                 460

Val Lys Ala Thr Asp Trp Lys Thr Asn Lys Tyr Gly Thr Leu Tyr Lys
465                 470                 475                 480

Ser Glu Ser Ala Ser Phe Thr Pro Asn Thr Asp Ile Ile Thr Arg Thr
                485                 490                 495

Thr Gly Pro Phe Arg Ser Met Pro Gln Ser Gly Val Leu Lys Ala Gly
            500                 505                 510

Gln Thr Ile His Tyr Asp Glu Val Met Lys Gln Asp Gly His Val Trp
        515                 520                 525

Val Gly Tyr Thr Gly Asn Ser Gly Gln Arg Ile Tyr Leu Pro Val Arg
    530                 535                 540

Thr Trp Asn Lys Ser Thr Asn Thr Leu Gly Val Leu Trp Gly Thr Ile
545                 550                 555                 560

Lys

<210> SEQ ID NO 25
<211> LENGTH: 1131
<212> TYPE: DNA
<213> ORGANISM: artificial
<220> FEATURE:
<223> OTHER INFORMATION: artificial construct

<400> SEQUENCE: 25
atgagaggat cgcatcacca tcaccatcac ggatctggct ctggatctgg tatcgaggga    60
aggccttata tggaactgg atccgcatgc gagctcgcaa agaaagatga aaaatcacaa     120
gtatgtagtg gtttggctat ggaaaaatat gacattacaa atttaaatgc taaacaagat   180
aaatcaaaga atgggagcgt gaaagagttg aaacatatct attcaaacca tattaaaggt   240
aacaagatta cagcaccaaa acctagtatt caaggtgtgg tcatccacaa tgattatggt   300
agtatgacac ctagtcaata cttaccatgg ttatatgcac gtgagaataa cggtacacac   360
```

-continued

```
gttaacggtt gggctagtgt ttatgcaaat agaaacgaag tgctttggta tcatccgaca    420
gactacgtag agtggcattg tggtaatcaa tgggcaaatg ctaacttaat cggatttgaa    480
gtgtgtgagt cgtatcctgg tagaatctcg gacaaattat tcttagaaaa tgaagaagcg    540
acattgaaag tagctgcgga tgtgatgaag tcgtacggat taccagttaa tcgcaacact    600
gtacgtctgc ataacgaatt cttcggaact tcttgtccac atcgttcgtg ggacttgcat    660
gttggcaaag gtgagcctta cacaactact aatattaata aaatgaaaga ctacttcatc    720
aaacgcatca acattatta tgacggtgga aagctagaag taagcaaagc agcaactatc    780
aaacaatctg acgttaagca agaagttaaa agcaagaag caaaacaaat tgtgaaagca    840
acagattgga aacagaataa agatggcatt tggtataaag ctgaacatgc ttcgttcaca    900
gtgacagcac cagagggaat tatcacaaga tacaaaggtc cttggactgg tcacccacaa    960
gctggtgtat acaaaaagg tcaaacgatt aaatatgatg aggttcaaaa atttgacggt   1020
catgtttggg tatcgtggga aacgtttgag ggcgaaactg tatacatgcc ggtacgcaca   1080
tgggacgcta aaactggtaa agttggtaag ttgtggggcg aaattaaata a            1131
```

<210> SEQ ID NO 26
<211> LENGTH: 376
<212> TYPE: PRT
<213> ORGANISM: artificial
<220> FEATURE:
<223> OTHER INFORMATION: artificial construct

<400> SEQUENCE: 26

```
Met Arg Gly Ser His His His His His His Gly Ser Gly Ser
1               5                   10                  15

Gly Ile Glu Gly Arg Pro Tyr Asn Gly Thr Gly Ser Ala Cys Glu Leu
            20                  25                  30

Ala Lys Lys Asp Glu Lys Ser Gln Val Cys Ser Gly Leu Ala Met Glu
        35                  40                  45

Lys Tyr Asp Ile Thr Asn Leu Asn Ala Lys Gln Asp Lys Ser Lys Asn
    50                  55                  60

Gly Ser Val Lys Glu Leu Lys His Ile Tyr Ser Asn His Ile Lys Gly
65                  70                  75                  80

Asn Lys Ile Thr Ala Pro Lys Pro Ser Ile Gln Gly Val Val Ile His
                85                  90                  95

Asn Asp Tyr Gly Ser Met Thr Pro Ser Gln Tyr Leu Pro Trp Leu Tyr
            100                 105                 110

Ala Arg Glu Asn Asn Gly Thr His Val Asn Gly Trp Ala Ser Val Tyr
        115                 120                 125

Ala Asn Arg Asn Glu Val Leu Trp Tyr His Pro Thr Asp Tyr Val Glu
    130                 135                 140

Trp His Cys Gly Asn Gln Trp Ala Asn Ala Asn Leu Ile Gly Phe Glu
145                 150                 155                 160

Val Cys Glu Ser Tyr Pro Gly Arg Ile Ser Asp Lys Leu Phe Leu Glu
                165                 170                 175

Asn Glu Glu Ala Thr Leu Lys Val Ala Ala Asp Val Met Lys Ser Tyr
            180                 185                 190

Gly Leu Pro Val Asn Arg Asn Thr Val Arg Leu His Asn Glu Phe Phe
        195                 200                 205

Gly Thr Ser Cys Pro His Arg Ser Trp Asp Leu His Val Gly Lys Gly
    210                 215                 220

Glu Pro Tyr Thr Thr Thr Asn Ile Asn Lys Met Lys Asp Tyr Phe Ile
```

```
              225                 230                 235                 240
Lys Arg Ile Lys His Tyr Tyr Asp Gly Gly Lys Leu Glu Val Ser Lys
                245                 250                 255

Ala Ala Thr Ile Lys Gln Ser Asp Val Lys Gln Glu Val Lys Lys Gln
                260                 265                 270

Glu Ala Lys Gln Ile Val Lys Ala Thr Asp Trp Lys Gln Asn Lys Asp
                275                 280                 285

Gly Ile Trp Tyr Lys Ala Glu His Ala Ser Phe Thr Val Thr Ala Pro
            290                 295                 300

Glu Gly Ile Ile Thr Arg Tyr Lys Gly Pro Trp Thr Gly His Pro Gln
305                 310                 315                 320

Ala Gly Val Leu Gln Lys Gly Gln Thr Ile Lys Tyr Asp Glu Val Gln
                325                 330                 335

Lys Phe Asp Gly His Val Trp Val Ser Trp Glu Thr Phe Glu Gly Glu
                340                 345                 350

Thr Val Tyr Met Pro Val Arg Thr Trp Asp Ala Lys Thr Gly Lys Val
                355                 360                 365

Gly Lys Leu Trp Gly Glu Ile Lys
        370                 375

<210> SEQ ID NO 27
<211> LENGTH: 1125
<212> TYPE: DNA
<213> ORGANISM: artificial
<220> FEATURE:
<223> OTHER INFORMATION: artificial construct

<400> SEQUENCE: 27
atgagaggat cgcatcacca tcaccatcac ggatctggct ctggatctgg tatcgaggga      60
aggccttata tggaactgga tccgcatgc gagctcgcaa agaaagatga aaatcacaa      120 gtatgtagtg gtttggctat ggaaaaatat gacattacaa atttaaatgc taaacaagat    180
aaatcaaaga atgggagcgt gaaagagttg aaacatatct attcaaacca tattaaaggt    240
aacaagatta cagcaccaaa acctagtatt caaggtgtgg tcatccacaa tgattatggt    300
agtatgacac tagtcaata cttaccatgg ttatatgcac gtgagaataa cggtacacac     360
gttaacggtt gggctagtgt ttatgcaaat agaaacgaag tgctttggta tcatccgaca    420
gactacgtag agtggcattg tggtaatcaa tgggcaaatg ctaacttaat cggatttgaa    480
gtgtgtgagt cgtatcctgg tagaatctcg gacaaattat tcttagaaaa tgaagaagcg    540
acattgaaag tagctgcgga tgtgatgaag tcgtacggat taccagttaa tcgcaacact    600
gtacgtctgc ataacgaatt cttcggaact tcttgtccac atcgttcgtg ggacttgcat    660
gttggcaaag gtgagcctta cacaactact aatattaata aaatgaaaga ctacttcatc    720
aaacgcatca acattatta tgacggtgga aagctagaag taagcaaagc agcaactatc    780
aaacaatctg acgttaagca agaagttaaa agcaagaag caaaacaaat tgtgaaagca    840
acagattgga aacaaacaa atatggcaca ctatataaat cagagtcagc tagcttcaca    900
cctaatacag atataataac aagaacgact ggtccattta gaagcatgcc gcagtcagga   960
gtcttaaaag caggtcaaac aattcattat gatgaagtga tgaaacaaga cggtcatgtt  1020
tgggtaggtt atacaggtaa cagtggccaa cgtatttact tgcctgtaag aacatggaat  1080
aaatctacta atactttagg tgttctttgg ggaactataa agtaa                   1125

<210> SEQ ID NO 28
```

<211> LENGTH: 374
<212> TYPE: PRT
<213> ORGANISM: artificial
<220> FEATURE:
<223> OTHER INFORMATION: artificial construct

<400> SEQUENCE: 28

Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Ala Lys Lys Asp Glu Lys Ser Gln Val Cys Ser Gly Leu Ala Met Glu
        35                  40                  45

Lys Tyr Asp Ile Thr Asn Leu Asn Ala Lys Gln Asp Lys Ser Lys Asn
    50                  55                  60

Gly Ser Val Lys Glu Leu Lys His Ile Tyr Ser Asn His Ile Lys Gly
65                  70                  75                  80

Asn Lys Ile Thr Ala Pro Lys Pro Ser Ile Gln Gly Val Val Ile His
                85                  90                  95

Asn Asp Tyr Gly Ser Met Thr Pro Ser Gln Tyr Leu Pro Trp Leu Tyr
            100                 105                 110

Ala Arg Glu Asn Asn Gly Thr His Val Asn Gly Trp Ala Ser Val Tyr
        115                 120                 125

Ala Asn Arg Asn Glu Val Leu Trp Tyr His Pro Thr Asp Tyr Val Glu
    130                 135                 140

Trp His Cys Gly Asn Gln Trp Ala Asn Ala Asn Leu Ile Gly Phe Glu
145                 150                 155                 160

Val Cys Glu Ser Tyr Pro Gly Arg Ile Ser Asp Lys Leu Phe Leu Glu
                165                 170                 175

Asn Glu Glu Ala Thr Leu Lys Val Ala Ala Asp Val Met Lys Ser Tyr
            180                 185                 190

Gly Leu Pro Val Asn Arg Asn Thr Val Arg Leu His Asn Glu Phe Phe
        195                 200                 205

Gly Thr Ser Cys Pro His Arg Ser Trp Asp Leu His Val Gly Lys Gly
    210                 215                 220

Glu Pro Tyr Thr Thr Thr Asn Ile Asn Lys Met Lys Asp Tyr Phe Ile
225                 230                 235                 240

Lys Arg Ile Lys His Tyr Tyr Asp Gly Gly Lys Leu Glu Val Ser Lys
                245                 250                 255

Ala Ala Thr Ile Lys Gln Ser Asp Val Lys Gln Glu Val Lys Lys Gln
            260                 265                 270

Glu Ala Lys Gln Ile Val Lys Ala Thr Asp Trp Lys Thr Asn Lys Tyr
        275                 280                 285

Gly Thr Leu Tyr Lys Ser Glu Ser Ala Ser Phe Thr Pro Asn Thr Asp
    290                 295                 300

Ile Ile Thr Arg Thr Thr Gly Pro Phe Arg Ser Met Pro Gln Ser Gly
305                 310                 315                 320

Val Leu Lys Ala Gly Gln Thr Ile His Tyr Asp Glu Val Met Lys Gln
                325                 330                 335

Asp Gly His Val Trp Val Gly Tyr Thr Gly Asn Ser Gly Gln Arg Ile
            340                 345                 350

Tyr Leu Pro Val Arg Thr Trp Asn Lys Ser Asn Thr Leu Gly Val
        355                 360                 365

Leu Trp Gly Thr Ile Lys
    370

<210> SEQ ID NO 29
<211> LENGTH: 1131
<212> TYPE: DNA
<213> ORGANISM: artificial
<220> FEATURE:
<223> OTHER INFORMATION: artificial construct

<400> SEQUENCE: 29

```
atgagaggat cgcatcacca tcaccatcac ggatctggct ctggatctgg tatcgaggga    60
aggcettata atggaactgg atccgcatgc gagctcgcaa agaaagatga aaatcacaa    120
gtatgtagtg gtttggctat ggaaaaatat gacattacaa atttaaatgc taaacaagat   180
aaatcaaaga atgggagcgt gaaagagttg aaacatatct attcaaacca tattaaaggt   240
aacaagatta cagcaccaaa acctagtatt caaggtgtgg tcatccacaa tgattatggt   300
agtatgacac tagtcaata cttaccatgg ttatatgcac gtgagaataa cggtacacac    360
gttaacggtt gggctagtgt ttatgcaaat agaaacgaag tgctttggta tcatccgaca   420
gactacgtag agtggcattg tggtaatcaa tgggcaaatg ctaacttaat cggatttgaa   480
gtgtgtgagt cgtatcctgg tagaatctcg gacaaattat tcttagaaaa tgaagaagcg   540
acattgaaag tagctgcgga tgtgatgaag tcgtacggat taccagttaa tcgcaacact   600
gtacgtctgc ataacgaatt cttcggaact tcttgtccac atcgttcgtg ggacttgcat   660
gttggcaaag gtgagcctta cacaactact aatattaata aaatgaaaga ctacttcatc   720
aaacgcatca acattatta tgacggtgga aagctagaag taagcaaagc agcaactatc   780
aaacaatctg acgttaagca agaagttaaa aagcaagaag caaaacaaat tgtgaaagca   840
acagatggta aatctgcaag taaataaca gttggaagta aagcgcctta taaccttaaa   900
tggtcaaaag gtgcttattt taatgcgaaa atcgacggct taggtgctac ttcagccact   960
agatacggtg ataatcgtac taactataga ttcgatgttg gacaggctgt atacgcgcct  1020
ggaacattaa tatatgtgtt tgaaattata gatggttggt gtcgcattta ttggaacaat  1080
cataatgagt ggatatggca tgagagattg attgtgaaag aagtgtttta a           1131
```

<210> SEQ ID NO 30
<211> LENGTH: 376
<212> TYPE: PRT
<213> ORGANISM: artificial
<220> FEATURE:
<223> OTHER INFORMATION: artificial construct

<400> SEQUENCE: 30

```
Met Arg Gly Ser His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Ala Lys Lys Asp Glu Lys Ser Gln Val Cys Ser Gly Leu Ala Met Glu
        35                  40                  45

Lys Tyr Asp Ile Thr Asn Leu Asn Ala Lys Gln Asp Lys Ser Lys Asn
    50                  55                  60

Gly Ser Val Lys Glu Leu Lys His Ile Tyr Ser Asn His Ile Lys Gly
65                  70                  75                  80

Asn Lys Ile Thr Ala Pro Lys Pro Ser Ile Gln Gly Val Val Ile His
                85                  90                  95

Asn Asp Tyr Gly Ser Met Thr Pro Ser Gln Tyr Leu Pro Trp Leu Tyr
            100                 105                 110
```

Ala Arg Glu Asn Asn Gly Thr His Val Asn Gly Trp Ala Ser Val Tyr
            115                 120                 125

Ala Asn Arg Asn Glu Val Leu Trp Tyr His Pro Thr Asp Tyr Val Glu
        130                 135                 140

Trp His Cys Gly Asn Gln Trp Ala Asn Ala Asn Leu Ile Gly Phe Glu
145                 150                 155                 160

Val Cys Glu Ser Tyr Pro Gly Arg Ile Ser Asp Lys Leu Phe Leu Glu
                165                 170                 175

Asn Glu Glu Ala Thr Leu Lys Val Ala Ala Asp Val Met Lys Ser Tyr
            180                 185                 190

Gly Leu Pro Val Asn Arg Asn Thr Val Arg Leu His Asn Glu Phe Phe
        195                 200                 205

Gly Thr Ser Cys Pro His Arg Ser Trp Asp Leu His Val Gly Lys Gly
    210                 215                 220

Glu Pro Tyr Thr Thr Thr Asn Ile Asn Lys Met Lys Asp Tyr Phe Ile
225                 230                 235                 240

Lys Arg Ile Lys His Tyr Tyr Asp Gly Gly Lys Leu Glu Val Ser Lys
                245                 250                 255

Ala Ala Thr Ile Lys Gln Ser Asp Val Lys Gln Glu Val Lys Lys Gln
            260                 265                 270

Glu Ala Lys Gln Ile Val Lys Ala Thr Asp Gly Lys Ser Ala Ser Lys
        275                 280                 285

Ile Thr Val Gly Ser Lys Ala Pro Tyr Asn Leu Lys Trp Ser Lys Gly
    290                 295                 300

Ala Tyr Phe Asn Ala Lys Ile Asp Gly Leu Gly Ala Thr Ser Ala Thr
305                 310                 315                 320

Arg Tyr Gly Asp Asn Arg Thr Asn Tyr Arg Phe Asp Val Gly Gln Ala
                325                 330                 335

Val Tyr Ala Pro Gly Thr Leu Ile Tyr Val Phe Glu Ile Ile Asp Gly
            340                 345                 350

Trp Cys Arg Ile Tyr Trp Asn His Asn Glu Trp Ile Trp His Glu
        355                 360                 365

Arg Leu Ile Val Lys Glu Val Phe
    370                 375

<210> SEQ ID NO 31
<211> LENGTH: 975
<212> TYPE: DNA
<213> ORGANISM: artificial
<220> FEATURE:
<223> OTHER INFORMATION: artificial construct

<400> SEQUENCE: 31
atgagaggat cgcatcacca tcaccatcac ggatctggct ctggatctgg tatcgaggga      60
aggccttata tggaactgg atccgcatgc gagctcatgg ctaagactca agcagaaata     120
aataaacgtt tagatgctta tgcaaaagga acagtagata gcccttacag agttaaaaaa     180
gctacaagtt atgacccatc atttggtgta atggaagcag gagccattga tgcagatggt     240
tactatcacg ctcagtgtca agaccttatt acagactatg tttatggtt aacagataat     300 aaagttagaa cttggggtaa tgctaaagac caaattaaac agagttatgg tactggattt     360
aaaatacatg aaaataaacc ttctactgta cctaaaaaag gttggattgc ggtatttaca     420
tccggtagtt atgaacagtg gggtcacata ggtattgtat atgatggagg taatacttct     480
acatttacta tttttagagca aaactggaat ggttatgcta ataaaaaacc tacaaaacgt     540

-continued

```
gtagataatt attacggatt aactcacttc attgaaatac ctgtaaaagc aggaaagcta    600
gaagtaagca aagcagcaac tatcaaacaa tctgacgtta agcaagaagt taaaaagcaa    660
gaagcaaaac aaattgtgaa agcaacagat tggaaacaga ataaagatgg catttggtat    720
aaagctgaac atgcttcgtt cacagtgaca gcaccagagg gaattatcac aagatacaaa    780
ggtccttgga ctggtcaccc acaagctggt gtattacaaa aggtcaaac gattaaatat     840 gatgaggttc aaaatttga cggtcatgtt tgggtatcgt gggaaacgtt tgagggcgaa     900
actgtataca tgccggtacg cacatgggac gctaaaactg gtaaagttgg taagttgtgg    960
ggcgaaatta aataa                                                     975
```

<210> SEQ ID NO 32
<211> LENGTH: 324
<212> TYPE: PRT
<213> ORGANISM: artificial
<220> FEATURE:
<223> OTHER INFORMATION: artificial construct

<400> SEQUENCE: 32

```
Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
                20                  25                  30

Met Ala Lys Thr Gln Ala Glu Ile Asn Lys Arg Leu Asp Ala Tyr Ala
            35                  40                  45

Lys Gly Thr Val Asp Ser Pro Tyr Arg Val Lys Lys Ala Thr Ser Tyr
        50                  55                  60

Asp Pro Ser Phe Gly Val Met Glu Ala Gly Ala Ile Asp Ala Asp Gly
65                  70                  75                  80

Tyr Tyr His Ala Gln Cys Gln Asp Leu Ile Thr Asp Tyr Val Leu Trp
                85                  90                  95

Leu Thr Asp Asn Lys Val Arg Thr Trp Gly Asn Ala Lys Asp Gln Ile
            100                 105                 110

Lys Gln Ser Tyr Gly Thr Gly Phe Lys Ile His Glu Asn Lys Pro Ser
        115                 120                 125

Thr Val Pro Lys Lys Gly Trp Ile Ala Val Phe Thr Ser Gly Ser Tyr
    130                 135                 140

Glu Gln Trp Gly His Ile Gly Ile Val Tyr Asp Gly Gly Asn Thr Ser
145                 150                 155                 160

Thr Phe Thr Ile Leu Glu Gln Asn Trp Asn Gly Tyr Ala Asn Lys Lys
                165                 170                 175

Pro Thr Lys Arg Val Asp Asn Tyr Tyr Gly Leu Thr His Phe Ile Glu
            180                 185                 190

Ile Pro Val Lys Ala Gly Lys Leu Glu Val Ser Lys Ala Ala Thr Ile
        195                 200                 205

Lys Gln Ser Asp Val Lys Gln Glu Val Lys Gln Glu Ala Lys Gln
    210                 215                 220

Ile Val Lys Ala Thr Asp Trp Lys Gln Asn Lys Asp Gly Ile Trp Tyr
225                 230                 235                 240

Lys Ala Glu His Ala Ser Phe Thr Val Thr Ala Pro Glu Gly Ile Ile
                245                 250                 255

Thr Arg Tyr Lys Gly Pro Trp Thr Gly His Pro Gln Ala Gly Val Leu
            260                 265                 270

Gln Lys Gly Gln Thr Ile Lys Tyr Asp Glu Val Gln Lys Phe Asp Gly
```

His Val Trp Val Ser Trp Glu Thr Phe Glu Gly Glu Thr Val Tyr Met
    275                 280                 285

Pro Val Arg Thr Trp Asp Ala Lys Thr Gly Lys Val Gly Lys Leu Trp
290                 295                 300

Gly Glu Ile Lys
305                 310                 315                 320

<210> SEQ ID NO 33
<211> LENGTH: 912
<212> TYPE: DNA
<213> ORGANISM: artificial
<220> FEATURE:
<223> OTHER INFORMATION: artificial construct

<400> SEQUENCE: 33
atgagaggat cgcatcacca tcaccatcac ggatctggct ctggatctgg tatcgaggga      60
aggcccttata tggaactgg atccgcatgc gagctcatgg ctaagactca agcagaaata    120
aataaacgtt tagatgctta tgcaaaagga acagtagata gcccttacag agttaaaaaa    180
gctacaagtt atgacccatc atttggtgta atggaagcag gagccattga tgcagatggt    240
tactatcacg ctcagtgtca agaccttatt acagactatg tttatggtt aacagataat    300
aaagttagaa cttggggtaa tgctaaagac caaattaaac agagttatgg tactggatt     360
aaaatacatg aaaataaacc ttctactgta cctaaaaaag gttggattgc ggtatttaca    420
tccggtagtt atgaacagtg gggtcacata ggtattgtat atgatggagg taatacttct    480
acatttacta ttttagagca aaactggaat ggttatgcta ataaaaaacc tacaaaacgt    540
gtagataatt attacggatt aactcacttc attgaaatac ctgtaaaagc aggaaaagca    600
ggtggtacag taactccaac gccgaataca ggttggaaaa caaacaaata tggcacacta    660
tataaatcag agtcagctag cttcacacct aatacagata taataacaag aacgactggt    720
ccatttagaa gcatgccgca gtcaggagtc ttaaaagcag gtcaaacaat tcattatgat    780
gaagtgatga acaagacgg tcatgtttgg gtaggttata caggtaacag tggccaacgt    840
atttacttgc ctgtaagaac atggaataaa tctactaata ctttaggtgt tctttgggga    900
actataaagt aa                                                         912

<210> SEQ ID NO 34
<211> LENGTH: 303
<212> TYPE: PRT
<213> ORGANISM: artificial
<220> FEATURE:
<223> OTHER INFORMATION: artificial construct

<400> SEQUENCE: 34

Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
                20                  25                  30

Met Ala Lys Thr Gln Ala Glu Ile Asn Lys Arg Leu Asp Ala Tyr Ala
            35                  40                  45

Lys Gly Thr Val Asp Ser Pro Tyr Arg Val Lys Lys Ala Thr Ser Tyr
        50                  55                  60

Asp Pro Ser Phe Gly Val Met Glu Ala Gly Ala Ile Asp Ala Asp Gly
65                  70                  75                  80

Tyr Tyr His Ala Gln Cys Gln Asp Leu Ile Thr Asp Tyr Val Leu Trp
                85                  90                  95

Leu Thr Asp Asn Lys Val Arg Thr Trp Gly Asn Ala Lys Asp Gln Ile
                100                 105                 110

Lys Gln Ser Tyr Gly Thr Gly Phe Lys Ile His Glu Asn Lys Pro Ser
            115                 120                 125

Thr Val Pro Lys Lys Gly Trp Ile Ala Val Phe Thr Ser Gly Ser Tyr
        130                 135                 140

Glu Gln Trp Gly His Ile Gly Ile Val Tyr Asp Gly Gly Asn Thr Ser
145                 150                 155                 160

Thr Phe Thr Ile Leu Glu Gln Asn Trp Asn Gly Tyr Ala Asn Lys Lys
                165                 170                 175

Pro Thr Lys Arg Val Asp Asn Tyr Tyr Gly Leu Thr His Phe Ile Glu
            180                 185                 190

Ile Pro Val Lys Ala Gly Lys Ala Gly Gly Thr Val Thr Pro Thr Pro
        195                 200                 205

Asn Thr Gly Trp Lys Thr Asn Lys Tyr Gly Thr Leu Tyr Lys Ser Glu
    210                 215                 220

Ser Ala Ser Phe Thr Pro Asn Thr Asp Ile Ile Thr Arg Thr Thr Gly
225                 230                 235                 240

Pro Phe Arg Ser Met Pro Gln Ser Gly Val Leu Lys Ala Gly Gln Thr
                245                 250                 255

Ile His Tyr Asp Glu Val Met Lys Gln Asp Gly His Val Trp Val Gly
            260                 265                 270

Tyr Thr Gly Asn Ser Gly Gln Arg Ile Tyr Leu Pro Val Arg Thr Trp
        275                 280                 285

Asn Lys Ser Thr Asn Thr Leu Gly Val Leu Trp Gly Thr Ile Lys
    290                 295                 300

<210> SEQ ID NO 35
<211> LENGTH: 966
<212> TYPE: DNA
<213> ORGANISM: artificial
<220> FEATURE:
<223> OTHER INFORMATION: artificial construct

<400> SEQUENCE: 35

```
atgagaggat cgcatcacca tcaccatcac ggatctggct ctggatctgg tatcgaggga    60
aggcccttata tggaactgg atccgcatgc gagctcatgg ctaagactca agcagaaata   120
aataaacgtt tagatgctta tgcaaaagga acagtagata gcccttacag agttaaaaaa   180
gctacaagtt atgacccatc atttggtgta atggaagcag gagccattga tgcagatggt   240
tactatcacg ctcagtgtca agaccttatt acagactatg tttatggtt aacagataat   300
aaagttagaa cttggggtaa tgctaaagac caaattaaac agagttatgg tactggattt   360
aaaatacatg aaaataaacc ttctactgta cctaaaaaag gttggattgc ggtatttaca   420
tccggtagtt atgaacagtg gggtcacata ggtattgtat atgatggagg taatacttct   480
acatttacta ttttagagca aaactggaat ggttatgcta ataaaaaacc tacaaaacgt   540
gtagataatt attacggatt aactcacttc attgaaatac ctgtaaaagc aggaactact   600
gttaaaaaag aaacagctaa gaaaagcgca agtaaaacgc tgcacctaa aaagaaagca   660
acactaaaag tttctaagaa tggtaaatct gcaagtaaaa taacagttgg aagtaaagcg   720
ccttataacc ttaaatggtc aaaaggtgct tattttaatg cgaaaatcga cggcttaggt   780
gctacttcag ccactagata cggtgataat cgtactaact atagattcga tgttggacag   840
gctgtatacg cgcctggaac attaatatat gtgtttgaaa ttatagatgg ttggtgtcgc   900
```

```
atttattgga acaatcataa tgagtggata tggcatgaga gattgattgt gaaagaagtg    960
ttttaa                                                                966
```

<210> SEQ ID NO 36
<211> LENGTH: 321
<212> TYPE: PRT
<213> ORGANISM: artificial
<220> FEATURE:
<223> OTHER INFORMATION: artificial construct

<400> SEQUENCE: 36

```
Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Met Ala Lys Thr Gln Ala Glu Ile Asn Lys Arg Leu Asp Ala Tyr Ala
        35                  40                  45

Lys Gly Thr Val Asp Ser Pro Tyr Arg Val Lys Ala Thr Ser Tyr
    50                  55                  60

Asp Pro Ser Phe Gly Val Met Glu Ala Gly Ala Ile Asp Ala Asp Gly
65                  70                  75                  80

Tyr Tyr His Ala Gln Cys Gln Asp Leu Ile Thr Asp Tyr Val Leu Trp
                85                  90                  95

Leu Thr Asp Asn Lys Val Arg Thr Trp Gly Asn Ala Lys Asp Gln Ile
            100                 105                 110

Lys Gln Ser Tyr Gly Thr Gly Phe Lys Ile His Glu Asn Lys Pro Ser
        115                 120                 125

Thr Val Pro Lys Lys Gly Trp Ile Ala Val Phe Thr Ser Gly Ser Tyr
    130                 135                 140

Glu Gln Trp Gly His Ile Gly Ile Val Tyr Asp Gly Gly Asn Thr Ser
145                 150                 155                 160

Thr Phe Thr Ile Leu Glu Gln Asn Trp Asn Gly Tyr Ala Asn Lys Lys
                165                 170                 175

Pro Thr Lys Arg Val Asp Asn Tyr Tyr Gly Leu Thr His Phe Ile Glu
            180                 185                 190

Ile Pro Val Lys Ala Gly Thr Thr Val Lys Lys Glu Thr Ala Lys Lys
        195                 200                 205

Ser Ala Ser Lys Thr Pro Ala Pro Lys Lys Ala Thr Leu Lys Val
    210                 215                 220

Ser Lys Asn Gly Lys Ser Ala Ser Lys Ile Thr Val Gly Ser Lys Ala
225                 230                 235                 240

Pro Tyr Asn Leu Lys Trp Ser Lys Gly Ala Tyr Phe Asn Ala Lys Ile
                245                 250                 255

Asp Gly Leu Gly Ala Thr Ser Ala Thr Arg Tyr Gly Asp Asn Arg Thr
            260                 265                 270

Asn Tyr Arg Phe Asp Val Gly Gln Ala Val Tyr Ala Pro Gly Thr Leu
        275                 280                 285

Ile Tyr Val Phe Glu Ile Ile Asp Gly Trp Cys Arg Ile Tyr Trp Asn
    290                 295                 300

Asn His Asn Glu Trp Ile Trp His Glu Arg Leu Ile Val Lys Glu Val
305                 310                 315                 320

Phe
```

<210> SEQ ID NO 37

<211> LENGTH: 927
<212> TYPE: DNA
<213> ORGANISM: artificial
<220> FEATURE:
<223> OTHER INFORMATION: artificial construct

<400> SEQUENCE: 37

```
atgagaggat cgcatcacca tcaccatcac ggatctggct ctggatctgg tatcgaggga      60
aggcnttata tggaactgg atccgcatgc gagctcatga aaaccctgaa acaagcagag     120
```
(Note: the above sequence is reproduced verbatim from the page)

```
atgagaggat cgcatcacca tcaccatcac ggatctggct ctggatctgg tatcgaggga      60
aggcnttata tggaactgg atccgcatgc gagctcatga aaaccctgaa acaagcagag     120
tcctacatta agagtaaagt aaatacagga actgattttg atggtttata tgggtatcag    180
tgtatggact tagcagtaga ttatatttac catgtaacag atggtaaaat aagaatgtgg    240
ggtaatgcta aggatgcgat aaataactct tttggtggta ctgctacggt atataaaaac    300
taccctgctt ttagacctaa gtacggtgat gtagtcgtat ggactactgg taattttgca    360
acttatggtc atatcgcaat agttactaac cctgacccta atggagacct tcaatatgtt    420
acagttcttg aacaaaactg gaacggtaac gggatttata aaccgagtt agctacaatc    480
agaacacacg attacacagg aattacacat tttattagac ctaactttgc tactgaatca    540
agtgtaaaaa agaaagatac aaagaaaaaa ccaaaaccat caaatagaga tggaataaat    600
aaagataaaa ttgtatatga tagaactaat attaattaca attggaaaca gaataaagat    660
ggcatttggt ataaagctga acatgcttcg ttcacagtga cagcaccaga gggaattatc    720
acaagataca aaggtccttg gactggtcac ccacaagctg tgtattaca aaaaggtcaa     780
acgattaaat atgatgaggt tcaaaaattt gacggtcatg tttgggtatc gtgggaaacg    840
tttgagggcg aaactgtata catgccggta cgcacatggg acgctaaaac tggtaaagtt    900
ggtaagttgt ggggcgaaat taaataa                                         927
```

<210> SEQ ID NO 38
<211> LENGTH: 308
<212> TYPE: PRT
<213> ORGANISM: artificial
<220> FEATURE:
<223> OTHER INFORMATION: artificial construct

<400> SEQUENCE: 38

```
Met Arg Gly Ser His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Met Lys Thr Leu Lys Gln Ala Glu Ser Tyr Ile Lys Ser Lys Val Asn
        35                  40                  45

Thr Gly Thr Asp Phe Asp Gly Leu Tyr Gly Tyr Gln Cys Met Asp Leu
    50                  55                  60

Ala Val Asp Tyr Ile Tyr His Val Thr Asp Gly Lys Ile Arg Met Trp
65                  70                  75                  80

Gly Asn Ala Lys Asp Ala Ile Asn Asn Ser Phe Gly Gly Thr Ala Thr
                85                  90                  95

Val Tyr Lys Asn Tyr Pro Ala Phe Arg Pro Lys Tyr Gly Asp Val Val
            100                 105                 110

Val Trp Thr Thr Gly Asn Phe Ala Thr Tyr Gly His Ile Ala Ile Val
        115                 120                 125

Thr Asn Pro Asp Pro Tyr Gly Asp Leu Gln Tyr Val Thr Val Leu Glu
    130                 135                 140

Gln Asn Trp Asn Gly Asn Gly Ile Tyr Lys Thr Glu Leu Ala Thr Ile
145                 150                 155                 160
```

```
Arg Thr His Asp Tyr Thr Gly Ile Thr His Phe Ile Arg Pro Asn Phe
            165                 170                 175
Ala Thr Glu Ser Ser Val Lys Lys Asp Thr Lys Lys Pro Lys
        180                 185                 190
Pro Ser Asn Arg Asp Gly Ile Asn Lys Asp Lys Ile Val Tyr Asp Arg
            195                 200                 205
Thr Asn Ile Asn Tyr Asn Trp Lys Gln Asn Lys Asp Gly Ile Trp Tyr
        210                 215                 220
Lys Ala Glu His Ala Ser Phe Thr Val Thr Ala Pro Glu Gly Ile Ile
225                 230                 235                 240
Thr Arg Tyr Lys Gly Pro Trp Thr Gly His Pro Gln Ala Gly Val Leu
                245                 250                 255
Gln Lys Gly Gln Thr Ile Lys Tyr Asp Glu Val Gln Lys Phe Asp Gly
            260                 265                 270
His Val Trp Val Ser Trp Glu Thr Phe Glu Gly Glu Thr Val Tyr Met
        275                 280                 285
Pro Val Arg Thr Trp Asp Ala Lys Thr Gly Lys Val Gly Lys Leu Trp
        290                 295                 300
Gly Glu Ile Lys
305

<210> SEQ ID NO 39
<211> LENGTH: 921
<212> TYPE: DNA
<213> ORGANISM: artificial
<220> FEATURE:
<223> OTHER INFORMATION: artificial construct

<400> SEQUENCE: 39
atgagaggat cgcatcacca tcaccatcac ggatctggct ctggatctgg tatcgaggga      60
aggcettata tggaactgg atccgcatgc gagctcatga aaaccctgaa acaagcagag      120
tcctacatta agagtaaagt aaatacagga actgattttg atggtttata tgggtatcag    180
tgtatggact tagcagtaga ttatatttac catgtaacag atggtaaaat aagaatgtgg    240
ggtaatgcta aggatgcgat aaataactct tttggtggta ctgctacggt atataaaaac    300
taccctgctt ttagacctaa gtacggtgat gtagtcgtat ggactactgg taattttgca    360
acttatggtc atatcgcaat agttactaac cctgacccttt atggagacct tcaatatgtt  420
acagttcttg aacaaaactg gaacggtaac gggatttata aaccgagtt agctacaatc    480
agaacacacg attacacagg aattacacat tttattagac taactttgc tactgaatca    540
agtgtaaaaa agaaagatac aaagaaaaaa ccaaaaccat caaatagaga tggaataaat  600
aaagataaaa ttgtatatga tagaactaat attaattaca attggaaaac aaacaaatat    660
ggcacactat ataatcaga gtcagctagc ttcacaccta atacagatat aataacaaga    720
acgactggtc catttagaag catgccgcag tcaggagtct taaaagcagg tcaaacaatt    780
cattatgatg aagtgatgaa acaagacggt catgtttggg taggttatac aggtaacagt    840
ggccaacgta tttacttgcc tgtaagaaca tggaataaat ctactaatac tttaggtgtt    900
ctttggggaa ctataaagta a                                              921

<210> SEQ ID NO 40
<211> LENGTH: 306
<212> TYPE: PRT
<213> ORGANISM: artificial
<220> FEATURE:
```

<223> OTHER INFORMATION: artificial construct

<400> SEQUENCE: 40

| | | | | | | | | | | | | | | |
|---|---|---|---|---|---|---|---|---|---|---|---|---|---|---|
| Met | Arg | Gly | Ser | His | His | His | His | His | His | Gly | Ser | Gly | Ser | Gly | Ser |
| 1 | | | | 5 | | | | | 10 | | | | | 15 |
| Gly | Ile | Glu | Gly | Arg | Pro | Tyr | Asn | Gly | Thr | Ser | Ala | Cys | Glu | Leu |
| | | | 20 | | | | | 25 | | | | | 30 | |
| Met | Lys | Thr | Leu | Lys | Gln | Ala | Glu | Ser | Tyr | Ile | Lys | Ser | Lys | Val | Asn |
| | | | 35 | | | | | 40 | | | | | 45 | |
| Thr | Gly | Thr | Asp | Phe | Asp | Gly | Leu | Tyr | Gly | Tyr | Gln | Cys | Met | Asp | Leu |
| | 50 | | | | | 55 | | | | | 60 | | | | |
| Ala | Val | Asp | Tyr | Ile | Tyr | His | Val | Thr | Asp | Gly | Lys | Ile | Arg | Met | Trp |
| 65 | | | | | 70 | | | | | 75 | | | | | 80 |
| Gly | Asn | Ala | Lys | Asp | Ala | Ile | Asn | Asn | Ser | Phe | Gly | Gly | Thr | Ala | Thr |
| | | | | 85 | | | | | 90 | | | | | 95 | |
| Val | Tyr | Lys | Asn | Tyr | Pro | Ala | Phe | Arg | Pro | Lys | Tyr | Gly | Asp | Val | Val |
| | | | 100 | | | | | 105 | | | | | 110 | | |
| Val | Trp | Thr | Thr | Gly | Asn | Phe | Ala | Thr | Tyr | Gly | His | Ile | Ala | Ile | Val |
| | | | 115 | | | | | 120 | | | | | 125 | | |
| Thr | Asn | Pro | Asp | Pro | Tyr | Gly | Asp | Leu | Gln | Tyr | Val | Thr | Val | Leu | Glu |
| | 130 | | | | | 135 | | | | | 140 | | | | |
| Gln | Asn | Trp | Asn | Gly | Asn | Gly | Ile | Tyr | Lys | Thr | Glu | Leu | Ala | Thr | Ile |
| 145 | | | | | 150 | | | | | 155 | | | | | 160 |
| Arg | Thr | His | Asp | Tyr | Thr | Gly | Ile | Thr | His | Phe | Ile | Arg | Pro | Asn | Phe |
| | | | | 165 | | | | | 170 | | | | | 175 | |
| Ala | Thr | Glu | Ser | Ser | Val | Lys | Lys | Lys | Asp | Thr | Lys | Lys | Lys | Pro | Lys |
| | | | | 180 | | | | | 185 | | | | | 190 | |
| Pro | Ser | Asn | Arg | Asp | Gly | Ile | Asn | Lys | Asp | Lys | Ile | Val | Tyr | Asp | Arg |
| | | | 195 | | | | | 200 | | | | | 205 | | |
| Thr | Asn | Ile | Asn | Tyr | Asn | Trp | Lys | Thr | Asn | Lys | Tyr | Gly | Thr | Leu | Tyr |
| | 210 | | | | | 215 | | | | | 220 | | | | |
| Lys | Ser | Glu | Ser | Ala | Ser | Phe | Thr | Pro | Asn | Thr | Asp | Ile | Ile | Thr | Arg |
| 225 | | | | | 230 | | | | | 235 | | | | | 240 |
| Thr | Thr | Gly | Pro | Phe | Arg | Ser | Met | Pro | Gln | Ser | Gly | Val | Leu | Lys | Ala |
| | | | | 245 | | | | | 250 | | | | | 255 | |
| Gly | Gln | Thr | Ile | His | Tyr | Asp | Glu | Val | Met | Lys | Gln | Asp | Gly | His | Val |
| | | | 260 | | | | | 265 | | | | | 270 | | |
| Trp | Val | Gly | Tyr | Thr | Gly | Asn | Ser | Gly | Gln | Arg | Ile | Tyr | Leu | Pro | Val |
| | | | 275 | | | | | 280 | | | | | 285 | | |
| Arg | Thr | Trp | Asn | Lys | Ser | Thr | Asn | Thr | Leu | Gly | Val | Leu | Trp | Gly | Thr |
| | 290 | | | | | 295 | | | | | 300 | | | | |
| Ile | Lys | | | | | | | | | | | | | | |
| 305 | | | | | | | | | | | | | | | |

<210> SEQ ID NO 41
<211> LENGTH: 927
<212> TYPE: DNA
<213> ORGANISM: artificial
<220> FEATURE:
<223> OTHER INFORMATION: artificial construct

<400> SEQUENCE: 41

```
atgagaggat cgcatcacca tcaccatcac ggatctggct ctggatctgg tatcgaggga      60
aggccttata tggaactgg atccgcatgc gagctcatga aaaccctgaa acaagcagag     120
tcctacatta agagtaaagt aaatacagga actgattttg atggtttata tgggtatcag    180
```

```
tgtatggact tagcagtaga ttatatttac catgtaacag atggtaaaat aagaatgtgg    240
ggtaatgcta aggatgcgat aaataactct tttggtggta ctgctacggt atataaaaac    300
taccctgctt ttagacctaa gtacggtgat gtagtcgtat ggactactgg taattttgca    360
acttatggtc atatcgcaat agttactaac cctgacccct tatggagacct tcaatatgtt    420 acagttcttg aacaaaactg gaacggtaac gggatttata aaccgagtt agctacaatc    480 agaacacacg attacacagg aattacacat tttattagac ctaactttgc tactgaatca    540
agtgtaaaaa agaaagatac aaagaaaaaa ccaaaaccat caaatagaga tggaataaat    600
aaagataaaa ttgtatatga tagaactaat attaattaca atggtaaatc tgcaagtaaa    660
ataacagttg gaagtaaagc gccttataac cttaaatggt caaaaggtgc ttattttaat    720
gcgaaaatcg acggcttagg tgctacttca gccactagat acggtgataa tcgtactaac    780
tatagattcg atgttggaca ggctgtatac gcgcctggaa cattaatata tgtgtttgaa    840
attatagatg gttggtgtcg catttattgg aacaatcata atgagtggat atggcatgag    900
agattgattg tgaaagaagt gttttaa                                         927
```

<210> SEQ ID NO 42
<211> LENGTH: 308
<212> TYPE: PRT
<213> ORGANISM: artificial
<220> FEATURE:
<223> OTHER INFORMATION: artificial construct

<400> SEQUENCE: 42

```
Met Arg Gly Ser His His His His His His Gly Ser Gly Ser
1               5                   10                  15

Gly Ile Glu Gly Arg Pro Tyr Asn Gly Thr Gly Ser Ala Cys Glu Leu
                20                  25                  30

Met Lys Thr Leu Lys Gln Ala Glu Ser Tyr Ile Lys Ser Lys Val Asn
            35                  40                  45

Thr Gly Thr Asp Phe Asp Gly Leu Tyr Gly Tyr Gln Cys Met Asp Leu
        50                  55                  60

Ala Val Asp Tyr Ile Tyr His Val Thr Asp Gly Lys Ile Arg Met Trp
65                  70                  75                  80

Gly Asn Ala Lys Asp Ala Ile Asn Asn Ser Phe Gly Gly Thr Ala Thr
                85                  90                  95

Val Tyr Lys Asn Tyr Pro Ala Phe Arg Pro Lys Tyr Gly Asp Val Val
                100                 105                 110

Val Trp Thr Thr Gly Asn Phe Ala Thr Tyr Gly His Ile Ala Ile Val
            115                 120                 125

Thr Asn Pro Asp Pro Tyr Gly Asp Leu Gln Tyr Val Thr Val Leu Glu
        130                 135                 140

Gln Asn Trp Asn Gly Asn Gly Ile Tyr Lys Thr Glu Leu Ala Thr Ile
145                 150                 155                 160

Arg Thr His Asp Tyr Thr Gly Ile Thr His Phe Ile Arg Pro Asn Phe
                165                 170                 175

Ala Thr Glu Ser Ser Val Lys Lys Lys Asp Thr Lys Lys Lys Pro Lys
            180                 185                 190

Pro Ser Asn Arg Asp Gly Ile Asn Lys Asp Lys Ile Val Tyr Asp Arg
        195                 200                 205

Thr Asn Ile Asn Tyr Asn Gly Lys Ser Ala Ser Lys Ile Thr Val Gly
        210                 215                 220
```

```
Ser Lys Ala Pro Tyr Asn Leu Lys Trp Ser Lys Gly Ala Tyr Phe Asn
225                 230                 235                 240

Ala Lys Ile Asp Gly Leu Gly Ala Thr Ser Ala Thr Arg Tyr Gly Asp
            245                 250                 255

Asn Arg Thr Asn Tyr Arg Phe Asp Val Gly Gln Ala Val Tyr Ala Pro
            260                 265                 270

Gly Thr Leu Ile Tyr Val Phe Glu Ile Ile Asp Gly Trp Cys Arg Ile
        275                 280                 285

Tyr Trp Asn Asn His Asn Glu Trp Ile Trp His Glu Arg Leu Ile Val
    290                 295                 300

Lys Glu Val Phe
305

<210> SEQ ID NO 43
<211> LENGTH: 843
<212> TYPE: DNA
<213> ORGANISM: artificial
<220> FEATURE:
<223> OTHER INFORMATION: artificial construct

<400> SEQUENCE: 43
atgagaggat cgcatcacca tcaccatcac ggatctggct ctggatctgg tatcgaggga    60
aggccttata tggaactgg atccgcatgc gagctcgctg caacacatga acattcagca   120
caatggttga ataattacaa aaaggatat ggttacggtc cttatccatt aggtataaat   180
ggcggtatgc actacggagt tgattttttt atgaatattg aacaccagt aaaagctatt   240 tcaagcggaa aatagttga agctggttgg agtaattacg gaggaggtaa tcaaataggt   300
cttattgaaa tgatggagt gcatagacaa tggtatatgc atctaagtaa atataatgtt   360
aaagtaggag attatgtcaa agctggtcaa ataatcggtt ggtctggaag cactggttat   420
tctacagcac cacatttaca cttccaaaga atggttaatt cattttcaaa ttcaactgcc   480
caagatccaa tgcctttctt aaagagcgca ggatatggaa aagcaggtgg tacagtaact   540
ccaacgccga atacaggttg aaacagaat aaagatggca tttggtataa agctgaacat   600
gcttcgttca cagtgacagc accagaggga attatcacaa gatacaaagg tccttggact   660
ggtcacccac aagctggtgt attacaaaaa ggtcaaacga ttaaatatga tgaggttcaa   720
aaatttgacg gtcatgtttg ggtatcgtgg gaaacgtttg agggcgaaac tgtatacatg   780
ccggtacgca catgggacgc taaaactggt aaagttggta agttgtgggg cgaaattaaa   840
taa                                                                 843

<210> SEQ ID NO 44
<211> LENGTH: 280
<212> TYPE: PRT
<213> ORGANISM: artificial
<220> FEATURE:
<223> OTHER INFORMATION: artificial construct

<400> SEQUENCE: 44

Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Ala Ala Thr His Glu His Ser Ala Gln Trp Leu Asn Asn Tyr Lys Lys
        35                  40                  45

Gly Tyr Gly Tyr Gly Pro Tyr Pro Leu Gly Ile Asn Gly Gly Met His
    50                  55                  60
```

Tyr Gly Val Asp Phe Phe Met Asn Ile Gly Thr Pro Val Lys Ala Ile
65                  70                  75                  80

Ser Ser Gly Lys Ile Val Glu Ala Gly Trp Ser Asn Tyr Gly Gly Gly
                85                  90                  95

Asn Gln Ile Gly Leu Ile Glu Asn Asp Gly Val His Arg Gln Trp Tyr
            100                 105                 110

Met His Leu Ser Lys Tyr Asn Val Lys Val Gly Asp Tyr Val Lys Ala
        115                 120                 125

Gly Gln Ile Ile Gly Trp Ser Gly Ser Thr Gly Tyr Ser Thr Ala Pro
    130                 135                 140

His Leu His Phe Gln Arg Met Val Asn Ser Phe Ser Asn Ser Thr Ala
145                 150                 155                 160

Gln Asp Pro Met Pro Phe Leu Lys Ser Ala Gly Tyr Gly Lys Ala Gly
                165                 170                 175

Gly Thr Val Thr Pro Thr Pro Asn Thr Gly Trp Lys Gln Asn Lys Asp
            180                 185                 190

Gly Ile Trp Tyr Lys Ala Glu His Ala Ser Phe Thr Val Thr Ala Pro
        195                 200                 205

Glu Gly Ile Ile Thr Arg Tyr Lys Gly Pro Trp Thr Gly His Pro Gln
    210                 215                 220

Ala Gly Val Leu Gln Lys Gly Gln Thr Ile Lys Tyr Asp Glu Val Gln
225                 230                 235                 240

Lys Phe Asp Gly His Val Trp Val Ser Trp Glu Thr Phe Glu Gly Glu
                245                 250                 255

Thr Val Tyr Met Pro Val Arg Thr Trp Asp Ala Lys Thr Gly Lys Val
            260                 265                 270

Gly Lys Leu Trp Gly Glu Ile Lys
        275                 280

<210> SEQ ID NO 45
<211> LENGTH: 837
<212> TYPE: DNA
<213> ORGANISM: artificial
<220> FEATURE:
<223> OTHER INFORMATION: artificial construct

<400> SEQUENCE: 45
atgagaggat cgcatcacca tcaccatcac ggatctggct ctggatctgg tatcgaggga      60 aggcct tata tggaactgg atccgcatgc gagctcgctg caacacatga acattcagca    120
caatggttga ataattacaa aaaaggatat ggttacggtc cttatccatt aggtataaat    180
ggcggtatgc actacggagt tgatttttt atgaatattg gaacaccagt aaaagctatt    240
tcaagcggaa aatagttga agctggttgg agtaattacg gaggaggtaa tcaaataggt    300
cttattgaaa atgatggagt gcatagacaa tggtatatgc atctaagtaa atataatgtt    360
aaagtaggag attatgtcaa agctggtcaa ataatcggtt ggtctggaag cactggttat    420
tctacagcac cacatttaca cttccaaaga atggttaatt catttttcaaa ttcaactgcc    480 caagatccaa tgccttctct aaagagcgca ggatatggaa aagcaggtgg tacagtaact    540
ccaacgccga atacaggttg aaaacaaac aaatatggca cactatataa atcagagtca    600
gctagcttca cacctaatac agatataata acaagaacga ctggtccatt tagaagcatg    660
ccgcagtcag gagtcttaaa agcaggtcaa acaattcatt atgatgaagt gatgaaacaa    720
gacggtcatg tttgggtagg ttatacaggt aacagtggcc aacgtattta cttgcctgta    780
agaacatgga ataaatctac taatacttta ggtgttcttt ggggaactat aaagtaa        837

<210> SEQ ID NO 46
<211> LENGTH: 278
<212> TYPE: PRT
<213> ORGANISM: artificial
<220> FEATURE:
<223> OTHER INFORMATION: artificial construct

<400> SEQUENCE: 46

Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Ala Ala Thr His Glu His Ser Ala Gln Trp Leu Asn Asn Tyr Lys Lys
        35                  40                  45

Gly Tyr Gly Tyr Gly Pro Tyr Pro Leu Gly Ile Asn Gly Gly Met His
    50                  55                  60

Tyr Gly Val Asp Phe Phe Met Asn Ile Gly Thr Pro Val Lys Ala Ile
65                  70                  75                  80

Ser Ser Gly Lys Ile Val Glu Ala Gly Trp Ser Asn Tyr Gly Gly Gly
                85                  90                  95

Asn Gln Ile Gly Leu Ile Glu Asn Asp Gly Val His Arg Gln Trp Tyr
            100                 105                 110

Met His Leu Ser Lys Tyr Asn Val Lys Val Gly Asp Tyr Val Lys Ala
        115                 120                 125

Gly Gln Ile Ile Gly Trp Ser Gly Ser Thr Gly Tyr Ser Thr Ala Pro
    130                 135                 140

His Leu His Phe Gln Arg Met Val Asn Ser Phe Ser Asn Ser Thr Ala
145                 150                 155                 160

Gln Asp Pro Met Pro Phe Leu Lys Ser Ala Gly Tyr Gly Lys Ala Gly
                165                 170                 175

Gly Thr Val Thr Pro Thr Pro Asn Thr Gly Trp Lys Thr Asn Lys Tyr
            180                 185                 190

Gly Thr Leu Tyr Lys Ser Glu Ser Ala Ser Phe Thr Pro Asn Thr Asp
        195                 200                 205

Ile Ile Thr Arg Thr Thr Gly Pro Phe Arg Ser Met Pro Gln Ser Gly
    210                 215                 220

Val Leu Lys Ala Gly Gln Thr Ile His Tyr Asp Glu Val Met Lys Gln
225                 230                 235                 240

Asp Gly His Val Trp Val Gly Tyr Thr Gly Asn Ser Gly Gln Arg Ile
                245                 250                 255

Tyr Leu Pro Val Arg Thr Trp Asn Lys Ser Thr Asn Thr Leu Gly Val
            260                 265                 270

Leu Trp Gly Thr Ile Lys
        275

<210> SEQ ID NO 47
<211> LENGTH: 843
<212> TYPE: DNA
<213> ORGANISM: artificial
<220> FEATURE:
<223> OTHER INFORMATION: artificial construct

<400> SEQUENCE: 47
atgagaggat cgcatcacca tcaccatcac ggatctggct ctggatctgg tatcgaggga        60 aggcctttata atggaactgg atccgcatgc gagctcgctg caacacatga acattcagca       120

-continued

```
caatggttga ataattacaa aaaaggatat ggttacggtc cttatccatt aggtataaat      180
ggcggtatgc actacggagt tgatttttt atgaatattg aacaccagt aaaagctatt       240 tcaagcggaa aaatagttga agctggttgg agtaattacg gaggaggtaa tcaaataggt      300
cttattgaaa atgatggagt gcatagacaa tggtatatgc atctaagtaa atataatgtt     360
aaagtaggag attatgtcaa agctggtcaa ataatcggtt ggtctggaag cactggttat      420
tctacagcac cacatttaca cttccaaaga atggttaatt catttcaaa ttcaactgcc       480 caagatccaa tgcctttctt aaagagcgca ggatatggaa aagcaggtgg tacagtaact      540
ccaacgccga atacaggtgg taaatctgca agtaaaataa cagttggaag taaagcgcct     600 tataaccta aatggtcaaa aggtgcttat tttaatgcga aaatcgacgg cttaggtgct       660
acttcagcca ctagatacgg tgataatcgt actaactata gattcgatgt tggacaggct     720
gtatacgcgc ctggaacatt aatatatgtg tttgaaatta tagatggttg gtgtcgcatt      780
tattggaaca atcataatga gtggatatgg catgagagat tgattgtgaa agaagtgttt     840
taa                                                                    843
```

<210> SEQ ID NO 48
<211> LENGTH: 280
<212> TYPE: PRT
<213> ORGANISM: artificial
<220> FEATURE:
<223> OTHER INFORMATION: artificial construct

<400> SEQUENCE: 48

```
Met Arg Gly Ser His His His His His His Gly Ser Gly Ser
1               5                   10                  15

Gly Ile Glu Gly Arg Pro Tyr Asn Gly Thr Gly Ser Ala Cys Glu Leu
            20                  25                  30

Ala Ala Thr His Glu His Ser Ala Gln Trp Leu Asn Asn Tyr Lys Lys
        35                  40                  45

Gly Tyr Gly Tyr Gly Pro Tyr Pro Leu Gly Ile Asn Gly Gly Met His
    50                  55                  60

Tyr Gly Val Asp Phe Phe Met Asn Ile Gly Thr Pro Val Lys Ala Ile
65                  70                  75                  80

Ser Ser Gly Lys Ile Val Glu Ala Gly Trp Ser Asn Tyr Gly Gly Gly
                85                  90                  95

Asn Gln Ile Gly Leu Ile Glu Asn Asp Gly Val His Arg Gln Trp Tyr
            100                 105                 110

Met His Leu Ser Lys Tyr Asn Val Lys Val Gly Asp Tyr Val Lys Ala
        115                 120                 125

Gly Gln Ile Ile Gly Trp Ser Gly Ser Thr Gly Tyr Ser Thr Ala Pro
    130                 135                 140

His Leu His Phe Gln Arg Met Val Asn Ser Phe Ser Asn Ser Thr Ala
145                 150                 155                 160

Gln Asp Pro Met Pro Phe Leu Lys Ser Ala Gly Tyr Gly Lys Ala Gly
                165                 170                 175

Gly Thr Val Thr Pro Thr Pro Asn Thr Gly Gly Lys Ser Ala Ser Lys
            180                 185                 190

Ile Thr Val Gly Ser Lys Ala Pro Tyr Asn Leu Lys Trp Ser Lys Gly
        195                 200                 205

Ala Tyr Phe Asn Ala Lys Ile Asp Gly Leu Gly Ala Thr Ser Ala Thr
    210                 215                 220
```

Arg Tyr Gly Asp Asn Arg Thr Asn Tyr Arg Phe Asp Val Gly Gln Ala
225                 230                 235                 240

Val Tyr Ala Pro Gly Thr Leu Ile Tyr Val Phe Glu Ile Ile Asp Gly
                245                 250                 255

Trp Cys Arg Ile Tyr Trp Asn Asn His Asn Glu Trp Ile Trp His Glu
            260                 265                 270

Arg Leu Ile Val Lys Glu Val Phe
            275                 280

<210> SEQ ID NO 49
<211> LENGTH: 1755
<212> TYPE: DNA
<213> ORGANISM: artificial
<220> FEATURE:
<223> OTHER INFORMATION: artificial construct

<400> SEQUENCE: 49

| | | | | | |
|---|---|---|---|---|---|
| atgagaggat | cgcatcacca | tcaccatcac | ggatctggct | ctggatctgg | tatcgaggga | 60 |
| agggcaaaga | aagatgaaaa | atcacaagta | tgtagtggtt | tggctatgga | aaaatatgac | 120 |
| attacaaatt | taaatgctaa | acaagataaa | tcaaagaatg | ggagcgtgaa | agagttgaaa | 180 |
| catatctatt | caaaccatat | taaaggtaac | aagattacag | caccaaaacc | tagtattcaa | 240 |
| ggtgtggtca | tccacaatga | ttatggtagt | atgacaccta | gtcaatactt | accatggtta | 300 |
| tatgcacgtg | agaataacgg | tacacacgtt | aacggttggg | ctagtgttta | tgcaaataga | 360 |
| aacgaagtgc | tttggtatca | tccgacagac | tacgtagagt | ggcattgtgg | taatcaatgg | 420 |
| gcaaatgcta | acttaatcgg | atttgaagtg | tgtgagtcgt | atcctggtag | aatctcggac | 480 |
| aaattattct | tagaaaatga | agaagcgaca | ttgaaagtag | ctgcggatgt | gatgaagtcg | 540 |
| tacgattac | cagttaatcg | caacactgta | cgtctgcata | acgaattctt | cggaacttct | 600 |
| tgtccacatc | gttcgtggga | cttgcatgtt | ggcaaaggtg | agccttacac | aactactaat | 660 |
| attaataaaa | tgaaagacta | cttcatcaaa | cgcatcaaac | attattatga | cggtgagctc | 720 |
| gcaaagaaag | atgaaaaatc | acaagtatgt | agtggtttgg | ctatggaaaa | atatgacatt | 780 |
| acaaatttaa | atgctaaaca | agataaatca | agaatggga | gcgtgaaaga | gttgaaacat | 840 |
| atctattcaa | accatattaa | aggtaacaag | attacagcac | caaaacctag | tattcaaggt | 900 |
| gtggtcatcc | acaatgatta | tggtagtatg | acacctagtc | aatacttacc | atggttatat | 960 |
| gcacgtgaga | taacggtac | acacgttaac | ggttgggcta | gtgtttatgc | aaatagaaac | 1020 |
| gaagtgcttt | ggtatcatcc | gacagactac | gtagagtggc | attgtggtaa | tcaatgggca | 1080 |
| aatgctaact | taatcggatt | tgaagtgtgt | gagtcgtatc | ctggtagaat | ctcggacaaa | 1140 |
| ttattcttag | aaaatgaaga | agcgacattg | aaagtagctg | cggatgtgat | gaagtcgtac | 1200 |
| ggattaccag | ttaatcgcaa | cactgtacgt | ctgcataacg | aattcttcgg | aacttcttgt | 1260 |
| ccacatcgtt | cgtgggactt | gcatgttggc | aaaggtgagc | cttacacaac | tactaatatt | 1320 |
| aataaaatga | aagactactt | catcaaacgc | atcaaacatt | attatgacgg | tggaaagcta | 1380 |
| gaagtaagca | agcagcaac | tatcaaacaa | tctgacgtta | agcaagaagt | taaaaagcaa | 1440 |
| gaagcaaaac | aaattgtgaa | agcaacagat | tggaaacaga | ataagatgg | catttggtat | 1500 |
| aaagctgaac | atgcttcgtt | cacagtgaca | gcaccagagg | gaattatcac | aagatacaaa | 1560 |
| ggtccttgga | ctggtcaccc | acaagctggt | gtattacaaa | aaggtcaaac | gattaaatat | 1620 |
| gatgaggttc | aaaaatttga | cggtcatgtt | tgggtatcgt | gggaaacgtt | tgagggcgaa | 1680 |
| actgtataca | tgccggtacg | cacatgggac | gctaaaactg | gtaaagttgg | taagttgtgg | 1740 | ggcgaaatta aataa                                                    1755

<210> SEQ ID NO 50
<211> LENGTH: 584
<212> TYPE: PRT
<213> ORGANISM: artificial
<220> FEATURE:
<223> OTHER INFORMATION: artificial construct

<400> SEQUENCE: 50

Met Arg Gly Ser His His His His His His Gly Ser Gly Ser Gly Ser
1               5                   10                  15

Gly Ile Glu Gly Arg Ala Lys Lys Asp Glu Lys Ser Gln Val Cys Ser
            20                  25                  30

Gly Leu Ala Met Glu Lys Tyr Asp Ile Thr Asn Leu Asn Ala Lys Gln
        35                  40                  45

Asp Lys Ser Lys Asn Gly Ser Val Lys Glu Leu Lys His Ile Tyr Ser
    50                  55                  60

Asn His Ile Lys Gly Asn Lys Ile Thr Ala Pro Lys Pro Ser Ile Gln
65                  70                  75                  80

Gly Val Val Ile His Asn Asp Tyr Gly Ser Met Thr Pro Ser Gln Tyr
                85                  90                  95

Leu Pro Trp Leu Tyr Ala Arg Glu Asn Asn Gly Thr His Val Asn Gly
            100                 105                 110

Trp Ala Ser Val Tyr Ala Asn Arg Asn Glu Val Leu Trp Tyr His Pro
        115                 120                 125

Thr Asp Tyr Val Glu Trp His Cys Gly Asn Gln Trp Ala Asn Ala Asn
    130                 135                 140

Leu Ile Gly Phe Glu Val Cys Glu Ser Tyr Pro Gly Arg Ile Ser Asp
145                 150                 155                 160

Lys Leu Phe Leu Glu Asn Glu Glu Ala Thr Leu Lys Val Ala Ala Asp
                165                 170                 175

Val Met Lys Ser Tyr Gly Leu Pro Val Asn Arg Asn Thr Val Arg Leu
            180                 185                 190

His Asn Glu Phe Phe Gly Thr Ser Cys Pro His Arg Ser Trp Asp Leu
        195                 200                 205

His Val Gly Lys Gly Glu Pro Tyr Thr Thr Thr Asn Ile Asn Lys Met
    210                 215                 220

Lys Asp Tyr Phe Ile Lys Arg Ile Lys His Tyr Tyr Asp Gly Glu Leu
225                 230                 235                 240

Ala Lys Lys Asp Glu Lys Ser Gln Val Cys Ser Gly Leu Ala Met Glu
                245                 250                 255

Lys Tyr Asp Ile Thr Asn Leu Asn Ala Lys Gln Asp Lys Ser Lys Asn
            260                 265                 270

Gly Ser Val Lys Glu Leu Lys His Ile Tyr Ser Asn His Ile Lys Gly
        275                 280                 285

Asn Lys Ile Thr Ala Pro Lys Pro Ser Ile Gln Gly Val Val Ile His
    290                 295                 300

Asn Asp Tyr Gly Ser Met Thr Pro Ser Gln Tyr Leu Pro Trp Leu Tyr
305                 310                 315                 320

Ala Arg Glu Asn Asn Gly Thr His Val Asn Gly Trp Ala Ser Val Tyr
                325                 330                 335

Ala Asn Arg Asn Glu Val Leu Trp Tyr His Pro Thr Asp Tyr Val Glu
            340                 345                 350

Trp His Cys Gly Asn Gln Trp Ala Asn Ala Asn Leu Ile Gly Phe Glu
            355                 360                 365

Val Cys Glu Ser Tyr Pro Gly Arg Ile Ser Asp Lys Leu Phe Leu Glu
    370                 375                 380

Asn Glu Glu Ala Thr Leu Lys Val Ala Ala Asp Val Met Lys Ser Tyr
385                 390                 395                 400

Gly Leu Pro Val Asn Arg Asn Thr Val Arg Leu His Asn Glu Phe Phe
                405                 410                 415

Gly Thr Ser Cys Pro His Arg Ser Trp Asp Leu His Val Gly Lys Gly
            420                 425                 430

Glu Pro Tyr Thr Thr Thr Asn Ile Asn Lys Met Lys Asp Tyr Phe Ile
        435                 440                 445

Lys Arg Ile Lys His Tyr Tyr Asp Gly Gly Lys Leu Glu Val Ser Lys
    450                 455                 460

Ala Ala Thr Ile Lys Gln Ser Asp Val Lys Gln Glu Val Lys Lys Gln
465                 470                 475                 480

Glu Ala Lys Gln Ile Val Lys Ala Thr Asp Trp Lys Gln Asn Lys Asp
                485                 490                 495

Gly Ile Trp Tyr Lys Ala Glu His Ala Ser Phe Thr Val Thr Ala Pro
            500                 505                 510

Glu Gly Ile Ile Thr Arg Tyr Lys Gly Pro Trp Thr Gly His Pro Gln
        515                 520                 525

Ala Gly Val Leu Gln Lys Gly Gln Thr Ile Lys Tyr Asp Glu Val Gln
    530                 535                 540

Lys Phe Asp Gly His Val Trp Val Ser Trp Glu Thr Phe Glu Gly Glu
545                 550                 555                 560

Thr Val Tyr Met Pro Val Arg Thr Trp Asp Ala Lys Thr Gly Lys Val
                565                 570                 575

Gly Lys Leu Trp Gly Glu Ile Lys
            580

<210> SEQ ID NO 51
<211> LENGTH: 1749
<212> TYPE: DNA
<213> ORGANISM: artificial
<220> FEATURE:
<223> OTHER INFORMATION: artificial construct

<400> SEQUENCE: 51
atgagaggat cgcatcacca tcaccatcac ggatctggct ctggatctgg tatcgaggga    60
agggcaaaga aagatgaaaa atcacaagta tgtagtggta tggctatgga aaaatatgac   120
attacaaatt taaatgctaa acaagataaa tcaaagaatg ggagcgtgaa agagttgaaa   180
catatctatt caaaccatat taaaggtaac aagattacag caccaaaacc tagtattcaa   240
ggtgtggtca tccacaatga ttatggtagt atgacaccta gtcaatactt accatggtta   300
tatgcacgtg agaataacgg tacacacgtt aacggttggg ctagtgttta tgcaaataga   360
aacgaagtgc tttggtatca tccgacagac tacgtagagt ggcattgtgg taatcaatgg   420
gcaaatgcta acttaatcgg atttgaagtg tgtgagtcgt atcctggtag aatctcggac   480
aaattattct tagaaaatga agaagcgaca ttgaaagtag ctgcggatgt gatgaagtcg   540
tacggattac cagttaatcg caacactgta cgtctgcata cgaattcttc cggaacttct   600
tgtccacatc gttcgtggga cttgcatgtt ggcaaaggtg agccttacac aactactaat   660
attaataaaa tgaaagacta cttcatcaaa cgcatcaaac attattatga cggtgagctc   720

-continued

```
gcaaagaaag atgaaaaatc acaagtatgt agtggtttgg ctatggaaaa atatgacatt   780
acaaatttaa atgctaaaca agataaatca aagaatggga gcgtgaaaga gttgaaacat   840
atctattcaa accatattaa aggtaacaag attacagcac caaaacctag tattcaaggt   900
gtggtcatcc acaatgatta tggtagtatg acacctagtc aatacttacc atggttatat   960
gcacgtgaga ataacggtac acacgttaac ggttgggcta gtgtttatgc aaatagaaac  1020
gaagtgcttt ggtatcatcc gacagactac gtagagtggc attgtggtaa tcaatgggca  1080
aatgctaact taatcggatt tgaagtgtgt gagtcgtatc ctggtagaat ctcggacaaa  1140
ttattcttag aaaatgaaga agcgacattg aaagtagctg cggatgtgat gaagtcgtac  1200
ggattaccag ttaatcgcaa cactgtacgt ctgcataacg aattcttcgg aacttcttgt  1260
ccacatcgtt cgtgggactt gcatgttggc aaaggtgagc cttacacaac tactaatatt  1320
aataaaatga agactactt catcaaacgc atcaaacatt attatgacgg tggaaagcta  1380
gaagtaagca aagcagcaac tatcaaacaa tctgacgtta agcaagaagt taaaaagcaa  1440
gaagcaaaac aaattgtgaa agcaacagat tggaaaacaa acaaatatgg cacactatat  1500
aaatcagagt cagctagctt cacacctaat acagatataa taacaagaac gactggtcca  1560
tttagaagca tgccgcagtc aggagtctta aaagcaggtc aaacaattca ttatgatgaa  1620
gtgatgaaac aagacggtca tgtttgggta ggttatacag gtaacagtgg ccaacgtatt  1680
tacttgcctg taagaacatg gaataaatct actaatactt taggtgttct ttggggaact  1740
ataaagtaa                                                         1749
```

<210> SEQ ID NO 52
<211> LENGTH: 582
<212> TYPE: PRT
<213> ORGANISM: artificial
<220> FEATURE:
<223> OTHER INFORMATION: artificial construct

<400> SEQUENCE: 52

```
Met Arg Gly Ser His His His His His His Gly Ser Gly Ser Gly Ser
1               5                   10                  15

Gly Ile Glu Gly Arg Ala Lys Lys Asp Glu Lys Ser Gln Val Cys Ser
            20                  25                  30

Gly Leu Ala Met Glu Lys Tyr Asp Ile Thr Asn Leu Asn Ala Lys Gln
        35                  40                  45

Asp Lys Ser Lys Asn Gly Ser Val Lys Glu Leu Lys His Ile Tyr Ser
    50                  55                  60

Asn His Ile Lys Gly Asn Lys Ile Thr Ala Pro Lys Pro Ser Ile Gln
65                  70                  75                  80

Gly Val Val Ile His Asn Asp Tyr Gly Ser Met Thr Pro Ser Gln Tyr
                85                  90                  95

Leu Pro Trp Leu Tyr Ala Arg Glu Asn Asn Gly Thr His Val Asn Gly
            100                 105                 110

Trp Ala Ser Val Tyr Ala Asn Arg Asn Glu Val Leu Trp Tyr His Pro
        115                 120                 125

Thr Asp Tyr Val Glu Trp His Cys Gly Asn Gln Trp Ala Asn Ala Asn
    130                 135                 140

Leu Ile Gly Phe Glu Val Cys Glu Ser Tyr Pro Gly Arg Ile Ser Asp
145                 150                 155                 160

Lys Leu Phe Leu Glu Asn Glu Glu Ala Thr Leu Lys Val Ala Ala Asp
                165                 170                 175
```

```
Val Met Lys Ser Tyr Gly Leu Pro Val Asn Arg Asn Thr Val Arg Leu
            180                 185                 190
His Asn Glu Phe Phe Gly Thr Ser Cys Pro His Arg Ser Trp Asp Leu
        195                 200                 205
His Val Gly Lys Gly Glu Pro Tyr Thr Thr Thr Asn Ile Asn Lys Met
        210                 215                 220
Lys Asp Tyr Phe Ile Lys Arg Ile Lys His Tyr Tyr Asp Gly Glu Leu
225                 230                 235                 240
Ala Lys Lys Asp Glu Lys Ser Gln Val Cys Ser Gly Leu Ala Met Glu
                245                 250                 255
Lys Tyr Asp Ile Thr Asn Leu Asn Ala Lys Gln Asp Lys Ser Lys Asn
            260                 265                 270
Gly Ser Val Lys Glu Leu Lys His Ile Tyr Ser Asn His Ile Lys Gly
        275                 280                 285
Asn Lys Ile Thr Ala Pro Lys Pro Ser Ile Gln Gly Val Val Ile His
290                 295                 300
Asn Asp Tyr Gly Ser Met Thr Pro Ser Gln Tyr Leu Pro Trp Leu Tyr
305                 310                 315                 320
Ala Arg Glu Asn Asn Gly Thr His Val Asn Gly Trp Ala Ser Val Tyr
                325                 330                 335
Ala Asn Arg Asn Glu Val Leu Trp Tyr His Pro Thr Asp Tyr Val Glu
            340                 345                 350
Trp His Cys Gly Asn Gln Trp Ala Asn Ala Asn Leu Ile Gly Phe Glu
        355                 360                 365
Val Cys Glu Ser Tyr Pro Gly Arg Ile Ser Asp Lys Leu Phe Leu Glu
        370                 375                 380
Asn Glu Glu Ala Thr Leu Lys Val Ala Ala Asp Val Met Lys Ser Tyr
385                 390                 395                 400
Gly Leu Pro Val Asn Arg Asn Thr Val Arg Leu His Asn Glu Phe Phe
                405                 410                 415
Gly Thr Ser Cys Pro His Arg Ser Trp Asp Leu His Val Gly Lys Gly
            420                 425                 430
Glu Pro Tyr Thr Thr Thr Asn Ile Asn Lys Met Lys Asp Tyr Phe Ile
        435                 440                 445
Lys Arg Ile Lys His Tyr Tyr Asp Gly Gly Lys Leu Glu Val Ser Lys
        450                 455                 460
Ala Ala Thr Ile Lys Gln Ser Asp Val Lys Gln Glu Val Lys Lys Gln
465                 470                 475                 480
Glu Ala Lys Gln Ile Val Lys Ala Thr Asp Trp Lys Thr Asn Lys Tyr
                485                 490                 495
Gly Thr Leu Tyr Lys Ser Glu Ser Ala Ser Phe Thr Pro Asn Thr Asp
            500                 505                 510
Ile Ile Thr Arg Thr Thr Gly Pro Phe Arg Ser Met Pro Gln Ser Gly
        515                 520                 525
Val Leu Lys Ala Gly Gln Thr Ile His Tyr Asp Glu Val Met Lys Gln
        530                 535                 540
Asp Gly His Val Trp Val Gly Tyr Thr Gly Asn Ser Gly Gln Arg Ile
545                 550                 555                 560
Tyr Leu Pro Val Arg Thr Trp Asn Lys Ser Thr Asn Thr Leu Gly Val
                565                 570                 575
Leu Trp Gly Thr Ile Lys
            580
```

<210> SEQ ID NO 53
<211> LENGTH: 1755
<212> TYPE: DNA
<213> ORGANISM: artificial
<220> FEATURE:
<223> OTHER INFORMATION: artificial construct

<400> SEQUENCE: 53

```
atgagaggat cgcatcacca tcaccatcac ggatctggct ctggatctgg tatcgaggga      60
agggcaaaga aagatgaaaa atcacaagta tgtagtggtt tggctatgga aaaatatgac     120
attacaaatt taaatgctaa acaagataaa tcaaagaatg ggagcgtgaa agagttgaaa     180
catatctatt caaaccatat taaaggtaac aagattacag caccaaaacc tagtattcaa     240
ggtgtggtca tccacaatga ttatggtagt atgacaccta gtcaatactt accatggtta     300
tatgcacgtg agaataacgg tacacacgtt aacggttggg ctagtgttta tgcaaataga     360
aacgaagtgc tttggtatca tccgacagac tacgtagagt ggcattgtgg taatcaatgg     420
gcaaatgcta acttaatcgg atttgaagtg tgtgagtcgt atcctggtag aatctcggac     480
aaattattct tagaaaatga agaagcgaca ttgaaagtag ctgcggatgt gatgaagtcg     540
tacggattac cagttaatcg caacactgta cgtctgcata cgaattctt cggaacttct      600
tgtccacatc gttcgtggga cttgcatgtt ggcaaaggtg agccttacac aactactaat     660
attaataaaa tgaaagacta cttcatcaaa cgcatcaaac attattatga cggtgagctc     720
gcaaagaaag atgaaaaatc acaagtatgt agtggtttgg ctatgaaaaa atatgacatt     780
acaaatttaa atgctaaaca agataaatca agaatgggag cgtgaaaga gttgaaacat      840
atctattcaa accatattaa aggtaacaag attacagcac aaaacctag tattcaaggt      900
gtggtcatcc acaatgatta tggtagtatg acacctagtc aatacttacc atggttatat     960
gcacgtgaga taacggtac acacgttaac ggttgggcta gtgtttatgc aaatagaaac    1020
gaagtgcttt ggtatcatcc gacagactac gtagagtggc attgtggtaa tcaatgggca    1080
aatgctaact taatcggatt tgaagtgtgt gagtcgtatc ctggtagaat ctcggacaaa    1140
ttattcttag aaaatgaaga agcgacattg aaagtagctg cggatgtgat gaagtcgtac    1200
ggattaccag ttaatcgcaa cactgtacgt ctgcataacg aattcttcgg aacttcttgt    1260
ccacatcgtt cgtgggactt gcatgttggc aaaggtgagc cttacacaac tactaatatt    1320
aataaaatga agactactt catcaaacgc atcaaacatt attatgacgg tgaaagcta      1380
gaagtaagca agcagcaac tatcaaacaa tctgacgtta agcaagaagt taaaagcaa      1440
gaagcaaaac aaattgtgaa agcaacagat ggtaaatctg caagtaaaat aacagttgga    1500
agtaaagcgc ttataaccct taaatggtca aaaggtgctt atttttaatgc gaaaatcgac    1560
ggcttaggtg ctacttcagc cactagatac ggtgataatc gtactaacta tagattcgat    1620
gttggacagg ctgtatacgc gcctggaaca ttaatatatg tgtttgaaat tatagatggt    1680
tggtgtcgca tttattggaa caatcataat gagtggatat ggcatgagag attgattgtg    1740
aaagaagtgt tttaa                                                    1755
```

<210> SEQ ID NO 54
<211> LENGTH: 584
<212> TYPE: PRT
<213> ORGANISM: artificial
<220> FEATURE:
<223> OTHER INFORMATION: artificial construct

<400> SEQUENCE: 54

-continued

```
Met Arg Gly Ser His His His His His His Gly Ser Gly Ser Gly Ser
1               5                   10                  15

Gly Ile Glu Gly Arg Ala Lys Lys Asp Glu Lys Ser Gln Val Cys Ser
            20                  25                  30

Gly Leu Ala Met Glu Lys Tyr Asp Ile Thr Asn Leu Asn Ala Lys Gln
        35                  40                  45

Asp Lys Ser Lys Asn Gly Ser Val Lys Glu Leu Lys His Ile Tyr Ser
    50                  55                  60

Asn His Ile Lys Gly Asn Lys Ile Thr Ala Pro Lys Pro Ser Ile Gln
65                  70                  75                  80

Gly Val Val Ile His Asn Asp Tyr Gly Ser Met Thr Pro Ser Gln Tyr
                85                  90                  95

Leu Pro Trp Leu Tyr Ala Arg Glu Asn Asn Gly Thr His Val Asn Gly
            100                 105                 110

Trp Ala Ser Val Tyr Ala Asn Arg Asn Glu Val Leu Trp Tyr His Pro
        115                 120                 125

Thr Asp Tyr Val Glu Trp His Cys Gly Asn Gln Trp Ala Asn Ala Asn
    130                 135                 140

Leu Ile Gly Phe Glu Val Cys Glu Ser Tyr Pro Gly Arg Ile Ser Asp
145                 150                 155                 160

Lys Leu Phe Leu Glu Asn Glu Glu Ala Thr Leu Lys Val Ala Ala Asp
                165                 170                 175

Val Met Lys Ser Tyr Gly Leu Pro Val Asn Arg Asn Thr Val Arg Leu
            180                 185                 190

His Asn Glu Phe Phe Gly Thr Ser Cys Pro His Arg Ser Trp Asp Leu
        195                 200                 205

His Val Gly Lys Gly Glu Pro Tyr Thr Thr Thr Asn Ile Asn Lys Met
    210                 215                 220

Lys Asp Tyr Phe Ile Lys Arg Ile Lys His Tyr Tyr Asp Gly Glu Leu
225                 230                 235                 240

Ala Lys Lys Asp Glu Lys Ser Gln Val Cys Ser Gly Leu Ala Met Glu
                245                 250                 255

Lys Tyr Asp Ile Thr Asn Leu Asn Ala Lys Gln Asp Lys Ser Lys Asn
            260                 265                 270

Gly Ser Val Lys Glu Leu Lys His Ile Tyr Ser Asn His Ile Lys Gly
        275                 280                 285

Asn Lys Ile Thr Ala Pro Lys Pro Ser Ile Gln Gly Val Val Ile His
    290                 295                 300

Asn Asp Tyr Gly Ser Met Thr Pro Ser Gln Tyr Leu Pro Trp Leu Tyr
305                 310                 315                 320

Ala Arg Glu Asn Asn Gly Thr His Val Asn Gly Trp Ala Ser Val Tyr
                325                 330                 335

Ala Asn Arg Asn Glu Val Leu Trp Tyr His Pro Thr Asp Tyr Val Glu
            340                 345                 350

Trp His Cys Gly Asn Gln Trp Ala Asn Ala Asn Leu Ile Gly Phe Glu
        355                 360                 365

Val Cys Glu Ser Tyr Pro Gly Arg Ile Ser Asp Lys Leu Phe Leu Glu
    370                 375                 380

Asn Glu Glu Ala Thr Leu Lys Val Ala Ala Asp Val Met Lys Ser Tyr
385                 390                 395                 400

Gly Leu Pro Val Asn Arg Asn Thr Val Arg Leu His Asn Glu Phe Phe
                405                 410                 415

Gly Thr Ser Cys Pro His Arg Ser Trp Asp Leu His Val Gly Lys Gly
```

```
                     420             425             430
Glu Pro Tyr Thr Thr Thr Asn Ile Asn Lys Met Lys Asp Tyr Phe Ile
                435             440             445

Lys Arg Ile Lys His Tyr Tyr Asp Gly Gly Lys Leu Glu Val Ser Lys
            450             455             460

Ala Ala Thr Ile Lys Gln Ser Asp Val Lys Gln Glu Val Lys Lys Gln
465             470             475             480

Glu Ala Lys Gln Ile Val Lys Ala Thr Asp Gly Lys Ser Ala Ser Lys
                485             490             495

Ile Thr Val Gly Ser Lys Ala Pro Tyr Asn Leu Lys Trp Ser Lys Gly
            500             505             510

Ala Tyr Phe Asn Ala Lys Ile Asp Gly Leu Gly Ala Thr Ser Ala Thr
            515             520             525

Arg Tyr Gly Asp Asn Arg Thr Asn Tyr Arg Phe Asp Val Gly Gln Ala
            530             535             540

Val Tyr Ala Pro Gly Thr Leu Ile Tyr Val Phe Glu Ile Ile Asp Gly
545             550             555             560

Trp Cys Arg Ile Tyr Trp Asn Asn His Asn Glu Trp Ile Trp His Glu
                565             570             575

Arg Leu Ile Val Lys Glu Val Phe
            580

<210> SEQ ID NO 55
<211> LENGTH: 1533
<212> TYPE: DNA
<213> ORGANISM: artificial
<220> FEATURE:
<223> OTHER INFORMATION: artificial construct

<400> SEQUENCE: 55
atgagaggat cgcatcacca tcaccatcac ggatctggct ctggatctgg tatcgaggga    60
aggatggcta agactcaagc agaaataaat aaacgtttag atgcttatgc aaaaggaaca   120
gtagatagcc cttacagagt taaaaagct acaagttatg acccatcatt tggtgtaatg    180
gaagcaggag ccattgatgc agatggttac tatcacgctc agtgtcaaga ccttattaca   240
gactatgttt tatggttaac agataataaa gttagaactt ggggtaatgc taaagaccaa   300
attaaacaga gttatggtac tggatttaaa atacatgaaa ataaaccttc tactgtacct   360
aaaaaaggtt ggattgcggt atttacatcc ggtagttatg aacagtgggg tcacataggt   420
attgtatatg atggaggtaa tacttctaca tttactattt tagagcaaaa ctggaatggt   480
tatgctaata aaaaacctac aaaacgtgta gataattatt acggattaac tcacttcatt   540
gaaatacctg taaagcagg aactactgtt aaaaagaaa cagctaagaa agcgcaagt     600 aaaacgcctg cacctaaaaa gaaagcaaca ctaaaagttt ctaagaatga gctcatggct   660
aagactcaag cagaaataaa taacgtttta gatgcttatg caaaggaac agtagatagc    720 ccttacagag ttaaaaagc tacaagttat gacccatcat tggtgtaat ggaagcagga    780 gccattgatg cagatggtta ctatcacgct cagtgtcaag accttattac agactatgtt   840
ttatggttaa cagataataa agttagaact tggggtaatg ctaaagacca aattaaacag   900
agttatggta ctggatttaa aatacatgaa ataaaccctt ctactgtacc taaaaaaggt   960
tggattgcgg tatttacatc cggtagttat gaacagtggg gtcacatagg tattgtatat  1020
gatggaggta atacttctac atttactatt ttagagcaaa actggaatgg ttatgctaat  1080
aaaaaaccta caaaacgtgt agataattat tacggattaa ctcacttcat tgaaatacct  1140
```

-continued

```
gtaaaagcag gaaagctaga agtaagcaaa gcagcaacta tcaaacaatc tgacgttaag      1200
caagaagtta aaaagcaaga agcaaaacaa attgtgaaag caacagattg gaaacagaat      1260
aaagatggca tttggtataa agctgaacat gcttcgttca cagtgacagc accagaggga      1320
attatcacaa gatacaaagg tccttggact ggtcacccac aagctggtgt attacaaaaa      1380
ggtcaaacga ttaaatatga tgaggttcaa aaatttgacg gtcatgtttg ggtatcgtgg      1440
gaaacgtttg agggcgaaac tgtatacatg ccggtacgca catgggacgc taaaactggt      1500
aaagttggta agttgtgggg cgaaattaaa taa                                   1533
```

<210> SEQ ID NO 56
<211> LENGTH: 510
<212> TYPE: PRT
<213> ORGANISM: artificial
<220> FEATURE:
<223> OTHER INFORMATION: artificial construct

<400> SEQUENCE: 56

```
Met Arg Gly Ser His His His His His Gly Ser Gly Ser Gly Ser
1               5                  10                  15

Gly Ile Glu Gly Arg Met Ala Lys Thr Gln Ala Glu Ile Asn Lys Arg
            20                  25                  30

Leu Asp Ala Tyr Ala Lys Gly Thr Val Asp Ser Pro Tyr Arg Val Lys
        35                  40                  45

Lys Ala Thr Ser Tyr Asp Pro Ser Phe Gly Val Met Glu Ala Gly Ala
    50                  55                  60

Ile Asp Ala Asp Gly Tyr Tyr His Ala Gln Cys Gln Asp Leu Ile Thr
65                  70                  75                  80

Asp Tyr Val Leu Trp Leu Thr Asp Asn Lys Val Arg Thr Trp Gly Asn
                85                  90                  95

Ala Lys Asp Gln Ile Lys Gln Ser Tyr Gly Thr Gly Phe Lys Ile His
            100                 105                 110

Glu Asn Lys Pro Ser Thr Val Pro Lys Lys Gly Trp Ile Ala Val Phe
        115                 120                 125

Thr Ser Gly Ser Tyr Glu Gln Trp Gly His Ile Gly Ile Val Tyr Asp
    130                 135                 140

Gly Gly Asn Thr Ser Thr Phe Thr Ile Leu Glu Gln Asn Trp Asn Gly
145                 150                 155                 160

Tyr Ala Asn Lys Lys Pro Thr Lys Arg Val Asp Asn Tyr Tyr Gly Leu
                165                 170                 175

Thr His Phe Ile Glu Ile Pro Val Lys Ala Gly Thr Thr Val Lys Lys
            180                 185                 190

Glu Thr Ala Lys Lys Ser Ala Ser Lys Thr Pro Ala Pro Lys Lys Lys
        195                 200                 205

Ala Thr Leu Lys Val Ser Lys Asn Glu Leu Met Ala Lys Thr Gln Ala
    210                 215                 220

Glu Ile Asn Lys Arg Leu Asp Ala Tyr Ala Lys Gly Thr Val Asp Ser
225                 230                 235                 240

Pro Tyr Arg Val Lys Lys Ala Thr Ser Tyr Asp Pro Ser Phe Gly Val
                245                 250                 255

Met Glu Ala Gly Ala Ile Asp Ala Asp Gly Tyr Tyr His Ala Gln Cys
            260                 265                 270

Gln Asp Leu Ile Thr Asp Tyr Val Leu Trp Leu Thr Asp Asn Lys Val
        275                 280                 285
```

```
Arg Thr Trp Gly Asn Ala Lys Asp Gln Ile Lys Gln Ser Tyr Gly Thr
        290                 295                 300

Gly Phe Lys Ile His Glu Asn Lys Pro Ser Thr Val Pro Lys Lys Gly
305                 310                 315                 320

Trp Ile Ala Val Phe Thr Ser Gly Ser Tyr Glu Gln Trp Gly His Ile
                325                 330                 335

Gly Ile Val Tyr Asp Gly Gly Asn Thr Ser Thr Phe Thr Ile Leu Glu
            340                 345                 350

Gln Asn Trp Asn Gly Tyr Ala Asn Lys Lys Pro Thr Lys Arg Val Asp
        355                 360                 365

Asn Tyr Tyr Gly Leu Thr His Phe Ile Glu Ile Pro Val Lys Ala Gly
370                 375                 380

Lys Leu Glu Val Ser Lys Ala Ala Thr Ile Lys Gln Ser Asp Val Lys
385                 390                 395                 400

Gln Glu Val Lys Lys Gln Ala Lys Gln Ile Val Lys Ala Thr Asp
                405                 410                 415

Trp Lys Gln Asn Lys Asp Gly Ile Trp Tyr Lys Ala Glu His Ala Ser
                420                 425                 430

Phe Thr Val Thr Ala Pro Glu Gly Ile Ile Thr Arg Tyr Lys Gly Pro
                435                 440                 445

Trp Thr Gly His Pro Gln Ala Gly Val Leu Gln Lys Gly Gln Thr Ile
        450                 455                 460

Lys Tyr Asp Glu Val Gln Lys Phe Asp Gly His Val Trp Val Ser Trp
465                 470                 475                 480

Glu Thr Phe Glu Gly Glu Thr Val Tyr Met Pro Val Arg Thr Trp Asp
                485                 490                 495

Ala Lys Thr Gly Lys Val Gly Lys Leu Trp Gly Glu Ile Lys
                500                 505                 510

<210> SEQ ID NO 57
<211> LENGTH: 1470
<212> TYPE: DNA
<213> ORGANISM: artificial
<220> FEATURE:
<223> OTHER INFORMATION: artificial construct

<400> SEQUENCE: 57
atgagaggat cgcatcacca tcaccatcac ggatctggct ctggatctgg tatcgaggga      60
aggatggcta agactcaagc agaaataaat aaacgtttag atgcttatgc aaaaggaaca     120
gtagatagcc ttacagagt taaaaaagct acaagttatg acccatcatt tggtgtaatg     180
gaagcaggag ccattgatgc agatggttac tatcacgctc agtgtcaaga ccttattaca     240
gactatgttt atggttaac agataataaa gttagaactt ggggtaatgc taaagaccaa     300
attaaacaga gttatggtac tggatttaaa atacatgaaa ataaaccttc tactgtacct     360
aaaaaaggtt ggattgcggt atttacatcc ggtagttatg aacagtgggg tcacataggt     420
attgtatatg atggaggtaa tacttctaca tttactattt tagagcaaaa ctggaatggt     480
tatgctaata aaaaacctac aaaacgtgta gataattatt acggattaac tcacttcatt     540
gaaatacctg taaagcagg aactactgtt aaaaagaaa cagctaagaa aagcgcaagt     600
aaaacgcctg cacctaaaaa gaaagcaaca ctaaagtttt ctaagaatga gctcatggct     660
aagactcaag cagaaataaa taacgtttta gatgcttatg caaaggaac agtagatagc     720 ccttacagag ttaaaaaagc tacaagttat gacccatcat tggtgtaat ggaagcagga     780 gccattgatg cagatggtta ctatcacgct cagtgtcaag accttattac agactatgtt     840
```

```
ttatggttaa cagataataa agttagaact tggggtaatg ctaaagacca aattaaacag      900
agttatggta ctggatttaa aatacatgaa aataaacctt ctactgtacc taaaaaaggt      960
tggattgcgg tatttacatc cggtagttat gaacagtggg gtcacatagg tattgtatat     1020
gatggaggta atacttctac atttactatt ttagagcaaa actggaatgg ttatgctaat     1080
aaaaaaccta caaacgtgt agataattat tacggattaa ctcacttcat tgaaatacct     1140
```

```
gtaaaagcag gaaaagcagg tggtacagta actccaacgc cgaatacagg ttggaaaaca     1200
aacaaatatg gcacactata taaatcagag tcagctagct tcacacctaa tacagatata     1260
ataacaagaa cgactggtcc atttagaagc atgccgcagt caggagtctt aaaagcaggt     1320
caaacaattc attatgatga agtgatgaaa caagacggtc atgtttgggt aggttataca     1380
ggtaacagtg gccaacgtat ttacttgcct gtaagaacat ggaataaatc tactaatact     1440
ttaggtgttc tttggggaac tataaagtaa                                      1470
```

<210> SEQ ID NO 58
<211> LENGTH: 489
<212> TYPE: PRT
<213> ORGANISM: artificial
<220> FEATURE:
<223> OTHER INFORMATION: artificial construct

<400> SEQUENCE: 58

```
Met Arg Gly Ser His His His His His His Gly Ser Gly Ser Gly Ser
1               5                   10                  15

Gly Ile Glu Gly Arg Met Ala Lys Thr Gln Ala Glu Ile Asn Lys Arg
            20                  25                  30

Leu Asp Ala Tyr Ala Lys Gly Thr Val Asp Ser Pro Tyr Arg Val Lys
        35                  40                  45

Lys Ala Thr Ser Tyr Asp Pro Ser Phe Gly Val Met Glu Ala Gly Ala
    50                  55                  60

Ile Asp Ala Asp Gly Tyr Tyr His Ala Gln Cys Gln Asp Leu Ile Thr
65                  70                  75                  80

Asp Tyr Val Leu Trp Leu Thr Asp Asn Lys Val Arg Thr Trp Gly Asn
                85                  90                  95

Ala Lys Asp Gln Ile Lys Gln Ser Tyr Gly Thr Gly Phe Lys Ile His
            100                 105                 110

Glu Asn Lys Pro Ser Thr Val Pro Lys Lys Gly Trp Ile Ala Val Phe
        115                 120                 125

Thr Ser Gly Ser Tyr Glu Gln Trp Gly His Ile Gly Ile Val Tyr Asp
    130                 135                 140

Gly Gly Asn Thr Ser Thr Phe Thr Ile Leu Glu Gln Asn Trp Asn Gly
145                 150                 155                 160

Tyr Ala Asn Lys Lys Pro Thr Lys Arg Val Asp Asn Tyr Tyr Gly Leu
                165                 170                 175

Thr His Phe Ile Glu Ile Pro Val Lys Ala Gly Thr Thr Val Lys Lys
            180                 185                 190

Glu Thr Ala Lys Lys Ser Ala Ser Lys Thr Pro Ala Pro Lys Lys Lys
        195                 200                 205

Ala Thr Leu Lys Val Ser Lys Asn Glu Leu Met Ala Lys Thr Gln Ala
    210                 215                 220

Glu Ile Asn Lys Arg Leu Asp Ala Tyr Ala Lys Gly Thr Val Asp Ser
225                 230                 235                 240

Pro Tyr Arg Val Lys Lys Ala Thr Ser Tyr Asp Pro Ser Phe Gly Val
```

```
                        245                 250                 255
Met Glu Ala Gly Ala Ile Asp Ala Asp Gly Tyr Tyr His Ala Gln Cys
            260                 265                 270

Gln Asp Leu Ile Thr Asp Tyr Val Leu Trp Leu Thr Asp Asn Lys Val
            275                 280                 285

Arg Thr Trp Gly Asn Ala Lys Asp Gln Ile Lys Gln Ser Tyr Gly Thr
            290                 295                 300

Gly Phe Lys Ile His Glu Asn Lys Pro Ser Thr Val Pro Lys Lys Gly
305                 310                 315                 320

Trp Ile Ala Val Phe Thr Ser Gly Ser Tyr Glu Gln Trp Gly His Ile
                325                 330                 335

Gly Ile Val Tyr Asp Gly Gly Asn Thr Ser Thr Phe Thr Ile Leu Glu
                340                 345                 350

Gln Asn Trp Asn Gly Tyr Ala Asn Lys Lys Pro Thr Lys Arg Val Asp
            355                 360                 365

Asn Tyr Tyr Gly Leu Thr His Phe Ile Glu Ile Pro Val Lys Ala Gly
370                 375                 380

Lys Ala Gly Gly Thr Val Thr Pro Thr Pro Asn Thr Gly Trp Lys Thr
385                 390                 395                 400

Asn Lys Tyr Gly Thr Leu Tyr Lys Ser Glu Ser Ala Ser Phe Thr Pro
                405                 410                 415

Asn Thr Asp Ile Ile Thr Arg Thr Thr Gly Pro Phe Arg Ser Met Pro
            420                 425                 430

Gln Ser Gly Val Leu Lys Ala Gly Gln Thr Ile His Tyr Asp Glu Val
            435                 440                 445

Met Lys Gln Asp Gly His Val Trp Val Gly Tyr Thr Gly Asn Ser Gly
            450                 455                 460

Gln Arg Ile Tyr Leu Pro Val Arg Thr Trp Asn Lys Ser Thr Asn Thr
465                 470                 475                 480

Leu Gly Val Leu Trp Gly Thr Ile Lys
                485
```

<210> SEQ ID NO 59
<211> LENGTH: 1524
<212> TYPE: DNA
<213> ORGANISM: artificial
<220> FEATURE:
<223> OTHER INFORMATION: artificial construct

<400> SEQUENCE: 59

| | | | | | |
|---|---|---|---|---|---|
| atgagaggat | cgcatcacca | tcaccatcac | ggatctggct | ctggatctgg | tatcgaggga | 60 |
| aggatggcta | agactcaagc | agaaataaat | aaacgtttag | atgcttatgc | aaaaggaaca | 120 |
| gtagatagcc | cttacagagt | taaaaaagct | acaagttatg | acccatcatt | tggtgtaatg | 180 |
| gaagcaggag | ccattgatgc | agatggttac | tatcacgctc | agtgtcaaga | ccttattaca | 240 |
| gactatgttt | tatggttaac | agataataaa | gttagaactt | ggggtaatgc | taaagaccaa | 300 |
| attaaacaga | gttatggtac | tggatttaaa | atacatgaaa | ataaaccttc | tactgtacct | 360 |
| aaaaaaggtt | ggattgcggt | atttacatcc | ggtagttatg | aacagtgggg | tcacataggt | 420 |
| attgtatatg | atggaggtaa | tacttctaca | tttactattt | tagagcaaaa | ctggaatggt | 480 |
| tatgctaata | aaaaacctac | aaaacgtgta | gataattatt | acggattaac | tcacttcatt | 540 |
| gaaatacctg | taaagcagg | aactactgtt | aaaaaagaaa | cagctaagaa | agcgcaagt | 600 |
| aaaacgcctg | cacctaaaaa | gaaagcaaca | ctaaagtttt | ctaagaatga | gctcatggct | 660 |

```
aagactcaag cagaaataaa taaacgttta gatgcttatg caaaaggaac agtagatagc    720
ccttacagag ttaaaaaagc tacaagttat gacccatcat ttggtgtaat ggaagcagga    780
gccattgatg cagatggtta ctatcacgct cagtgtcaag accttattac agactatgtt    840
ttatggttaa cagataataa agttagaact tggggtaatg ctaaagacca aattaaacag    900
agttatggta ctggatttaa aatacatgaa aataaaccct ctactgtacc taaaaaggt     960 tggattgcgg tatttacatc cggtagttat gaacagtggg gtcacatagg tattgtatat   1020
gatggaggta atacttctac atttactatt ttagagcaaa actggaatgg ttatgctaat   1080
aaaaaaccta caaacgtgt agataattat tacggattaa ctcacttcat tgaaatacct    1140
gtaaaagcag gaactactgt taaaaaagaa acagctaaga aaagcgcaag taaaacgcct   1200
gcacctaaaa agaaagcaac actaaaagtt tctaagaatg gtaaatctgc aagtaaaata   1260
acagttggaa gtaaagcgcc ttataacctt aaatggtcaa aaggtgctta ttttaatgcg   1320
aaaatcgacg gcttaggtgc tacttcagcc actagatacg gtgataatcg tactaactat   1380
agattcgatg ttggacaggc tgtatacgcg cctggaacat aatatatgt gtttgaaatt    1440 atagatggtt ggtgtcgcat ttattggaac aatcataatg agtggatatg catgagaga    1500 ttgattgtga aagaagtgtt ttaa                                          1524

<210> SEQ ID NO 60
<211> LENGTH: 507
<212> TYPE: PRT
<213> ORGANISM: artificial
<220> FEATURE:
<223> OTHER INFORMATION: artificial construct

<400> SEQUENCE: 60

Met Arg Gly Ser His His His His His Gly Ser Gly Ser Gly Ser
1               5                   10                  15

Gly Ile Glu Gly Arg Met Ala Lys Thr Gln Ala Glu Ile Asn Lys Arg
            20                  25                  30

Leu Asp Ala Tyr Ala Lys Gly Thr Val Asp Ser Pro Tyr Arg Val Lys
        35                  40                  45

Lys Ala Thr Ser Tyr Asp Pro Ser Phe Gly Val Met Glu Ala Gly Ala
    50                  55                  60

Ile Asp Ala Asp Gly Tyr Tyr His Ala Gln Cys Gln Asp Leu Ile Thr
65                  70                  75                  80

Asp Tyr Val Leu Trp Leu Thr Asp Asn Lys Val Arg Thr Trp Gly Asn
                85                  90                  95

Ala Lys Asp Gln Ile Lys Gln Ser Tyr Gly Thr Gly Phe Lys Ile His
            100                 105                 110

Glu Asn Lys Pro Ser Thr Val Pro Lys Lys Gly Trp Ile Ala Val Phe
        115                 120                 125

Thr Ser Gly Ser Tyr Glu Gln Trp Gly His Ile Gly Ile Val Tyr Asp
    130                 135                 140

Gly Gly Asn Thr Ser Thr Phe Thr Ile Leu Glu Gln Asn Trp Asn Gly
145                 150                 155                 160

Tyr Ala Asn Lys Lys Pro Thr Lys Arg Val Asp Asn Tyr Tyr Gly Leu
                165                 170                 175

Thr His Phe Ile Glu Ile Pro Val Lys Ala Gly Thr Thr Val Lys Lys
            180                 185                 190

Glu Thr Ala Lys Lys Ser Ala Ser Lys Thr Pro Ala Pro Lys Lys Lys
        195                 200                 205
```

```
Ala Thr Leu Lys Val Ser Lys Asn Glu Leu Met Ala Lys Thr Gln Ala
    210             215                 220
Glu Ile Asn Lys Arg Leu Asp Ala Tyr Ala Lys Gly Thr Val Asp Ser
225             230                 235                 240
Pro Tyr Arg Val Lys Lys Ala Thr Ser Tyr Asp Pro Ser Phe Gly Val
                245                 250                 255
Met Glu Ala Gly Ala Ile Asp Ala Asp Gly Tyr Tyr His Ala Gln Cys
            260                 265                 270
Gln Asp Leu Ile Thr Asp Tyr Val Leu Trp Leu Thr Asp Asn Lys Val
            275                 280                 285
Arg Thr Trp Gly Asn Ala Lys Asp Gln Ile Lys Gln Ser Tyr Gly Thr
290             295                 300
Gly Phe Lys Ile His Glu Asn Lys Pro Ser Thr Val Pro Lys Lys Gly
305             310                 315                 320
Trp Ile Ala Val Phe Thr Ser Gly Ser Tyr Glu Gln Trp Gly His Ile
                325                 330                 335
Gly Ile Val Tyr Asp Gly Gly Asn Thr Ser Thr Phe Thr Ile Leu Glu
            340                 345                 350
Gln Asn Trp Asn Gly Tyr Ala Asn Lys Lys Pro Thr Lys Arg Val Asp
            355                 360                 365
Asn Tyr Tyr Gly Leu Thr His Phe Ile Glu Ile Pro Val Lys Ala Gly
370             375                 380
Thr Thr Val Lys Lys Glu Thr Ala Lys Lys Ser Ala Ser Lys Thr Pro
385             390                 395                 400
Ala Pro Lys Lys Lys Ala Thr Leu Lys Val Ser Lys Asn Gly Lys Ser
                405                 410                 415
Ala Ser Lys Ile Thr Val Gly Ser Lys Ala Pro Tyr Asn Leu Lys Trp
            420                 425                 430
Ser Lys Gly Ala Tyr Phe Asn Ala Lys Ile Asp Gly Leu Gly Ala Thr
            435                 440                 445
Ser Ala Thr Arg Tyr Gly Asp Asn Arg Thr Asn Tyr Arg Phe Asp Val
450             455                 460
Gly Gln Ala Val Tyr Ala Pro Gly Thr Leu Ile Tyr Val Phe Glu Ile
465             470                 475                 480
Ile Asp Gly Trp Cys Arg Ile Tyr Trp Asn Asn His Asn Glu Trp Ile
                485                 490                 495
Trp His Glu Arg Leu Ile Val Lys Glu Val Phe
            500                 505

<210> SEQ ID NO 61
<211> LENGTH: 1446
<212> TYPE: DNA
<213> ORGANISM: artificial
<220> FEATURE:
<223> OTHER INFORMATION: artificial construct

<400> SEQUENCE: 61
atgagaggat cgcatcacca tcaccatcac ggatctggct ctggatctgg tatcgaggga      60
aggatgaaaa ccctgaaaca agcagagtcc tacattaaga gtaaagtaaa tacaggaact     120
gattttgatg gtttatatgg gtatcagtgt atggacttag cagtagatta tatttaccat     180
gtaacagatg gtaaaataag aatgtggggt aatgctaagg atgcgataaa taactctttt     240
ggtggtactg ctacggtata taaaaactac cctgctttta gacctaagta cggtgatgta     300
gtcgtatgga ctactggtaa ttttgcaact tatggtcata tcgcaatagt tactaaccct     360
```

```
gacccttatg gagaccttca atatgttaca gttcttgaac aaaactggaa cggtaacggg    420
atttataaaa ccgagttagc tacaatcaga acacacgatt acacaggaat tacacatttt    480
attagaccta actttgctac tgaatcaagt gtaaaaaaga agatacaaa gaaaaaacca    540 aaaccatcaa atagagatgg aataaataaa gataaaattg tatatgatag aactaatatt    600
aattacaatg agctcatgaa acccctgaaa caagcagagt cctacattaa gagtaaagta    660
aatacaggaa ctgattttga tggtttatat gggtatcagt gtatggactt agcagtagat    720
tatatttacc atgtaacaga tggtaaaata agaatgtggg gtaatgctaa ggatgcgata    780
aataactctt ttggtggtac tgctacggta tataaaaact accctgcttt tagacctaag    840
tacggtgatg tagtcgtatg gactactggt aattttgcaa cttatggtca tatcgcaata    900
gttactaacc ctgacccctta tggagacctt caatatgtta cagttcttga acaaaactgg    960
aacggtaacg ggatttataa aaccgagtta gctacaatca gaacacacga ttacacagga    1020
attacacatt ttattagacc taactttgct actgaatcaa gtgtaaaaaa gaaagataca    1080
aagaaaaaac caaaccatc aaatagagat ggaataaata aagataaaat tgtatatgat    1140
agaactaata ttaattacaa ttggaaacag aataaagatg gcatttggta taaagctgaa    1200
catgcttcgt tcacagtgac agcaccagag ggaattatca aagatacaa aggtccttgg    1260 actggtcacc cacaagctgg tgtattcaa aaaggtcaaa cgattaaata tgatgaggtt    1320
caaaaatttg acggtcatgt ttgggtatcg tgggaaacgt ttgagggcga aactgtatac    1380
atgccggtac gcacatggga cgctaaaact ggtaaagttg gtaagttgtg gggcgaaatt    1440
aaataa                                                                1446
```

<210> SEQ ID NO 62
<211> LENGTH: 481
<212> TYPE: PRT
<213> ORGANISM: artificial
<220> FEATURE:
<223> OTHER INFORMATION: artificial construct

<400> SEQUENCE: 62

```
Met Arg Gly Ser His His His His His His Gly Ser Gly Ser Gly Ser
1               5                   10                  15

Gly Ile Glu Gly Arg Met Lys Thr Leu Lys Gln Ala Glu Ser Tyr Ile
                20                  25                  30

Lys Ser Lys Val Asn Thr Gly Thr Asp Phe Asp Gly Leu Tyr Gly Tyr
            35                  40                  45

Gln Cys Met Asp Leu Ala Val Asp Tyr Ile Tyr His Val Thr Asp Gly
        50                  55                  60

Lys Ile Arg Met Trp Gly Asn Ala Lys Asp Ala Ile Asn Asn Ser Phe
65                  70                  75                  80

Gly Gly Thr Ala Thr Val Tyr Lys Asn Tyr Pro Ala Phe Arg Pro Lys
                85                  90                  95

Tyr Gly Asp Val Val Trp Thr Thr Gly Asn Phe Ala Thr Tyr Gly
                100                 105                 110

His Ile Ala Ile Val Thr Asn Pro Asp Pro Tyr Gly Asp Leu Gln Tyr
            115                 120                 125

Val Thr Val Leu Glu Gln Asn Trp Asn Gly Asn Gly Ile Tyr Lys Thr
        130                 135                 140

Glu Leu Ala Thr Ile Arg Thr His Asp Tyr Thr Gly Ile Thr His Phe
145                 150                 155                 160

Ile Arg Pro Asn Phe Ala Thr Glu Ser Ser Val Lys Lys Lys Asp Thr
```

165                 170                 175
Lys Lys Lys Pro Lys Pro Ser Asn Arg Asp Gly Ile Asn Lys Asp Lys
            180                 185                 190

Ile Val Tyr Asp Arg Thr Asn Ile Asn Tyr Asn Glu Leu Met Lys Thr
            195                 200                 205

Leu Lys Gln Ala Glu Ser Tyr Ile Lys Ser Lys Val Asn Thr Gly Thr
        210                 215                 220

Asp Phe Asp Gly Leu Tyr Gly Tyr Gln Cys Met Asp Leu Ala Val Asp
225                 230                 235                 240

Tyr Ile Tyr His Val Thr Asp Gly Lys Ile Arg Met Trp Gly Asn Ala
                245                 250                 255

Lys Asp Ala Ile Asn Asn Ser Phe Gly Gly Thr Ala Thr Val Tyr Lys
            260                 265                 270

Asn Tyr Pro Ala Phe Arg Pro Lys Tyr Gly Asp Val Val Val Trp Thr
        275                 280                 285

Thr Gly Asn Phe Ala Thr Tyr Gly His Ile Ala Ile Val Thr Asn Pro
    290                 295                 300

Asp Pro Tyr Gly Asp Leu Gln Tyr Val Thr Val Leu Glu Gln Asn Trp
305                 310                 315                 320

Asn Gly Asn Gly Ile Tyr Lys Thr Glu Leu Ala Thr Ile Arg Thr His
                325                 330                 335

Asp Tyr Thr Gly Ile Thr His Phe Ile Arg Pro Asn Phe Ala Thr Glu
            340                 345                 350

Ser Ser Val Lys Lys Lys Asp Thr Lys Lys Lys Pro Lys Pro Ser Asn
        355                 360                 365

Arg Asp Gly Ile Asn Lys Asp Lys Ile Val Tyr Asp Arg Thr Asn Ile
370                 375                 380

Asn Tyr Asn Trp Lys Gln Asn Lys Asp Gly Ile Trp Tyr Lys Ala Glu
385                 390                 395                 400

His Ala Ser Phe Thr Val Thr Ala Pro Glu Gly Ile Ile Thr Arg Tyr
                405                 410                 415

Lys Gly Pro Trp Thr Gly His Pro Gln Ala Gly Val Leu Gln Lys Gly
            420                 425                 430

Gln Thr Ile Lys Tyr Asp Glu Val Gln Lys Phe Asp Gly His Val Trp
        435                 440                 445

Val Ser Trp Glu Thr Phe Glu Gly Glu Thr Val Tyr Met Pro Val Arg
        450                 455                 460

Thr Trp Asp Ala Lys Thr Gly Lys Val Gly Lys Leu Trp Gly Glu Ile
465                 470                 475                 480

Lys

<210> SEQ ID NO 63
<211> LENGTH: 1440
<212> TYPE: DNA
<213> ORGANISM: artificial
<220> FEATURE:
<223> OTHER INFORMATION: artificial construct

<400> SEQUENCE: 63
atgagaggat cgcatcacca tcaccatcac ggatctggct ctggatctgg tatcgaggga    60
aggatgaaaa ccctgaaaca agcagagtcc tacattaaga gtaaagtaaa tacaggaact   120
gattttgatg gtttatatgg gtatcagtgt atggacttag cagtagatta tatttaccat   180
gtaacagatg gtaaaataag aatgtggggt aatgctaagg atgcgataaa taactctttt   240

```
ggtggtactg ctacggtata taaaaactac cctgctttta gacctaagta cggtgatgta    300
gtcgtatgga ctactggtaa ttttgcaact tatggtcata tcgcaatagt tactaaccct    360
gacccttatg gagaccttca atatgttaca gttcttgaac aaaactggaa cggtaacggg    420
atttataaaa ccgagttagc tacaatcaga acacacgatt acacaggaat tacacatttt    480
attagaccta actttgctac tgaatcaagt gtaaaaaga aagatacaaa gaaaaaacca    540
aaaccatcaa atagagatgg aataaataaa gataaaattg tatatgatag aactaatatt    600
aattacaatg agctcatgaa accctgaaa caagcagagt cctacattaa gagtaaagta    660
aatacaggaa ctgattttga tggtttatat gggtatcagt gtatggactt agcagtagat    720
tatatttacc atgtaacaga tggtaaaata agaatgtggg gtaatgctaa ggatgcgata    780
aataactctt ttggtggtac tgctacggta tataaaaact accctgcttt tagacctaag    840
tacggtgatg tagtcgtatg gactactggt aattttgcaa cttatggtca tatcgcaata    900
gttactaacc ctgacccttta tggagacctt caatatgtta cagttcttga acaaaactgg    960
aacggtaacg ggatttataa aaccgagtta gctacaatca gaacacacga ttacacagga  1020
attacacatt ttattagacc taactttgct actgaatcaa gtgtaaaaaa gaaagataca  1080
aagaaaaaac caaaaccatc aaatagagat ggaataaata agataaaaat tgtatatgat  1140
agaactaata ttaattacaa ttggaaaaca acaaatatg gcacactata taatcagag  1200 tcagctagct tcacacctaa tacagatata ataacaagaa cgactggtcc atttagaagc  1260
atgccgcagt caggagtctt aaaagcaggt caaacaattc attatgatga agtgatgaaa  1320
caagacggtc atgtttgggt aggttataca ggtaacagtg ccaacgtat ttacttgcct  1380 gtaagaacat ggaataaatc tactaatact ttaggtgttc tttggggaac tataaagtaa  1440
```

<210> SEQ ID NO 64
<211> LENGTH: 479
<212> TYPE: PRT
<213> ORGANISM: artificial
<220> FEATURE:
<223> OTHER INFORMATION: artificial construct

<400> SEQUENCE: 64

```
Met Arg Gly Ser His His His His His Gly Ser Gly Ser Gly Ser
1               5                   10                  15

Gly Ile Glu Gly Arg Met Lys Thr Leu Lys Gln Ala Glu Ser Tyr Ile
            20                  25                  30

Lys Ser Lys Val Asn Thr Gly Thr Asp Phe Asp Gly Leu Tyr Gly Tyr
        35                  40                  45

Gln Cys Met Asp Leu Ala Val Asp Tyr Ile Tyr His Val Thr Asp Gly
    50                  55                  60

Lys Ile Arg Met Trp Gly Asn Ala Lys Asp Ala Ile Asn Asn Ser Phe
65                  70                  75                  80

Gly Gly Thr Ala Thr Val Tyr Lys Asn Tyr Pro Ala Phe Arg Pro Lys
                85                  90                  95

Tyr Gly Asp Val Val Val Trp Thr Thr Gly Asn Phe Ala Thr Tyr Gly
            100                 105                 110

His Ile Ala Ile Val Thr Asn Pro Asp Pro Tyr Gly Asp Leu Gln Tyr
        115                 120                 125

Val Thr Val Leu Glu Gln Asn Trp Asn Gly Asn Gly Ile Tyr Lys Thr
    130                 135                 140

Glu Leu Ala Thr Ile Arg Thr His Asp Tyr Thr Gly Ile Thr His Phe
145                 150                 155                 160
```

```
Ile Arg Pro Asn Phe Ala Thr Glu Ser Ser Val Lys Lys Asp Thr
                165                 170                 175
Lys Lys Lys Pro Lys Pro Ser Asn Arg Asp Gly Ile Asn Lys Asp Lys
            180                 185                 190
Ile Val Tyr Asp Arg Thr Asn Ile Asn Tyr Asn Glu Leu Met Lys Thr
        195                 200                 205
Leu Lys Gln Ala Glu Ser Tyr Ile Lys Ser Lys Val Asn Thr Gly Thr
    210                 215                 220
Asp Phe Asp Gly Leu Tyr Gly Tyr Gln Cys Met Asp Leu Ala Val Asp
225                 230                 235                 240
Tyr Ile Tyr His Val Thr Asp Gly Lys Ile Arg Met Trp Gly Asn Ala
                245                 250                 255
Lys Asp Ala Ile Asn Asn Ser Phe Gly Gly Thr Ala Thr Val Tyr Lys
            260                 265                 270
Asn Tyr Pro Ala Phe Arg Pro Lys Tyr Gly Asp Val Val Trp Thr
        275                 280                 285
Thr Gly Asn Phe Ala Thr Tyr Gly His Ile Ala Ile Val Thr Asn Pro
    290                 295                 300
Asp Pro Tyr Gly Asp Leu Gln Tyr Val Thr Val Leu Glu Gln Asn Trp
305                 310                 315                 320
Asn Gly Asn Gly Ile Tyr Lys Thr Glu Leu Ala Thr Ile Arg Thr His
                325                 330                 335
Asp Tyr Thr Gly Ile Thr His Phe Ile Arg Pro Asn Phe Ala Thr Glu
            340                 345                 350
Ser Ser Val Lys Lys Asp Thr Lys Lys Pro Lys Pro Ser Asn
    355                 360                 365
Arg Asp Gly Ile Asn Lys Asp Lys Ile Val Tyr Asp Arg Thr Asn Ile
370                 375                 380
Asn Tyr Asn Trp Lys Thr Asn Lys Tyr Gly Thr Leu Tyr Lys Ser Glu
385                 390                 395                 400
Ser Ala Ser Phe Thr Pro Asn Thr Asp Ile Ile Thr Arg Thr Gly
            405                 410                 415
Pro Phe Arg Ser Met Pro Gln Ser Gly Val Leu Lys Ala Gly Gln Thr
        420                 425                 430
Ile His Tyr Asp Glu Val Met Lys Gln Asp Gly His Val Trp Val Gly
    435                 440                 445
Tyr Thr Gly Asn Ser Gly Gln Arg Ile Tyr Leu Pro Val Arg Thr Trp
    450                 455                 460
Asn Lys Ser Thr Asn Thr Leu Gly Val Leu Trp Gly Thr Ile Lys
465                 470                 475
```

<210> SEQ ID NO 65
<211> LENGTH: 1446
<212> TYPE: DNA
<213> ORGANISM: artificial
<220> FEATURE:
<223> OTHER INFORMATION: artificial construct

<400> SEQUENCE: 65

```
atgagaggat cgcatcacca tcaccatcac ggatctggct ctggatctgg tatcgaggga    60
aggatgaaaa ccctgaaaca agcagagtcc tacattaaga gtaaagtaaa tacaggaact   120
gattttgatg gtttatatgg gtatcagtgt atggacttag cagtagatta tatttaccat   180
gtaacagatg gtaaaataag aatgtgtggt aatgctaagg atgcgataaa taactctttt   240
```

```
ggtggtactg ctacggtata taaaaactac cctgctttta gacctaagta cggtgatgta    300
gtcgtatgga ctactggtaa ttttgcaact tatggtcata tcgcaatagt tactaaccct    360
gacccttatg gagaccttca atatgttaca gttcttgaac aaaactggaa cggtaacggg    420
atttataaaa ccgagttagc tacaatcaga acacacgatt acacaggaat tacacatttt    480
attagaccta actttgctac tgaatcaagt gtaaaaaga aagatacaaa gaaaaaacca    540
aaaccatcaa atagagatgg aataaataaa gataaaattg tatatgatag aactaatatt    600
aattacaatg agctcatgaa accctgaaaa caagcagagt cctacattaa gagtaaagta    660
aatacaggaa ctgattttga tggtttatat gggtatcagt gtatggactt agcagtagat    720
tatatttacc atgtaacaga tggtaaaata agaatgtggg gtaatgctaa ggatgcgata    780
aataactctt ttggtggtac tgctacggta tataaaaact accctgcttt tagacctaag    840
tacggtgatg tagtcgtatg gactactggt aattttgcaa cttatggtca tatcgcaata    900
gttactaacc ctgacccttta tggagacctt caatatgtta cagttcttga acaaaactgg    960
aacggtaacg ggatttataa aaccgagtta gctacaatca gaacacacga ttacacagga    1020
attacacatt ttattagacc taactttgct actgaatcaa gtgtaaaaaa gaaagataca    1080
aagaaaaaac caaaaccatc aaatagagat ggaataaata agataaaat tgtatatgat    1140 agaactaata ttaattacaa tggtaaatct gcaagtaaaa taacagttgg aagtaaagcg    1200
ccttataacc ttaaatggtc aaaaggtgct tattttaatg cgaaaatcga cggcttaggt    1260
gctacttcag ccactagata cggtgataat cgtactaact atagattcga tgttggacag    1320
gctgtatacg cgcctggaac attaatatat gtgtttgaaa ttatagatgg ttggtgtcgc    1380
atttattgga caatcataa tgagtggata tggcatgaga gattgattgt gaaagaagtg    1440
ttttaa                                                                1446
```

<210> SEQ ID NO 66
<211> LENGTH: 481
<212> TYPE: PRT
<213> ORGANISM: artificial
<220> FEATURE:
<223> OTHER INFORMATION: artificial construct

<400> SEQUENCE: 66

Met Arg Gly Ser His His His His His His Gly Ser Gly Ser Gly Ser
1               5                   10                  15

Gly Ile Glu Gly Arg Met Lys Thr Leu Lys Gln Ala Glu Ser Tyr Ile
            20                  25                  30

Lys Ser Lys Val Asn Thr Gly Thr Asp Phe Asp Gly Leu Tyr Gly Tyr
        35                  40                  45

Gln Cys Met Asp Leu Ala Val Asp Tyr Ile Tyr His Val Thr Asp Gly
    50                  55                  60

Lys Ile Arg Met Trp Gly Asn Ala Lys Asp Ala Ile Asn Asn Ser Phe
65                  70                  75                  80

Gly Gly Thr Ala Thr Val Tyr Lys Asn Tyr Pro Ala Phe Arg Pro Lys
                85                  90                  95

Tyr Gly Asp Val Val Val Trp Thr Thr Gly Asn Phe Ala Thr Tyr Gly
            100                 105                 110

His Ile Ala Ile Val Thr Asn Pro Asp Pro Tyr Gly Asp Leu Gln Tyr
        115                 120                 125

Val Thr Val Leu Glu Gln Asn Trp Asn Gly Asn Gly Ile Tyr Lys Thr
    130                 135                 140

```
Glu Leu Ala Thr Ile Arg Thr His Asp Tyr Thr Gly Ile Thr His Phe
145                 150                 155                 160

Ile Arg Pro Asn Phe Ala Thr Glu Ser Ser Val Lys Lys Lys Asp Thr
            165                 170                 175

Lys Lys Lys Pro Lys Pro Ser Asn Arg Asp Gly Ile Asn Lys Asp Lys
        180                 185                 190

Ile Val Tyr Asp Arg Thr Asn Ile Asn Tyr Asn Glu Leu Met Lys Thr
    195                 200                 205

Leu Lys Gln Ala Glu Ser Tyr Ile Lys Ser Lys Val Asn Thr Gly Thr
210                 215                 220

Asp Phe Asp Gly Leu Tyr Gly Tyr Gln Cys Met Asp Leu Ala Val Asp
225                 230                 235                 240

Tyr Ile Tyr His Val Thr Asp Gly Lys Ile Arg Met Trp Gly Asn Ala
            245                 250                 255

Lys Asp Ala Ile Asn Asn Ser Phe Gly Gly Thr Ala Thr Val Tyr Lys
            260                 265                 270

Asn Tyr Pro Ala Phe Arg Pro Lys Tyr Gly Asp Val Val Val Trp Thr
        275                 280                 285

Thr Gly Asn Phe Ala Thr Tyr Gly His Ile Ala Ile Val Thr Asn Pro
    290                 295                 300

Asp Pro Tyr Gly Asp Leu Gln Tyr Val Thr Val Leu Glu Gln Asn Trp
305                 310                 315                 320

Asn Gly Asn Gly Ile Tyr Lys Thr Glu Leu Ala Thr Ile Arg Thr His
            325                 330                 335

Asp Tyr Thr Gly Ile Thr His Phe Ile Arg Pro Asn Phe Ala Thr Glu
            340                 345                 350

Ser Ser Val Lys Lys Lys Asp Thr Lys Lys Lys Pro Lys Pro Ser Asn
        355                 360                 365

Arg Asp Gly Ile Asn Lys Asp Lys Ile Val Tyr Asp Arg Thr Asn Ile
370                 375                 380

Asn Tyr Asn Gly Lys Ser Ala Ser Lys Ile Thr Val Gly Ser Lys Ala
385                 390                 395                 400

Pro Tyr Asn Leu Lys Trp Ser Lys Gly Ala Tyr Phe Asn Ala Lys Ile
            405                 410                 415

Asp Gly Leu Gly Ala Thr Ser Ala Thr Arg Tyr Gly Asp Asn Arg Thr
            420                 425                 430

Asn Tyr Arg Phe Asp Val Gly Gln Ala Val Tyr Ala Pro Gly Thr Leu
        435                 440                 445

Ile Tyr Val Phe Glu Ile Ile Asp Gly Trp Cys Arg Ile Tyr Trp Asn
    450                 455                 460

Asn His Asn Glu Trp Ile Trp His Glu Arg Leu Ile Val Lys Glu Val
465                 470                 475                 480

Phe

<210> SEQ ID NO 67
<211> LENGTH: 1278
<212> TYPE: DNA
<213> ORGANISM: artificial
<220> FEATURE:
<223> OTHER INFORMATION: artificial construct

<400> SEQUENCE: 67
atgagaggat cgcatcacca tcaccatcac ggatctggct ctggatctgg tatcgaggga      60
agggctgcaa cacatgaaca ttcagcacaa tggttgaata attacaaaaa aggatatggt     120
```

```
tacggtcctt atccattagg tataaatggc ggtatgcact acggagttga ttttttttatg    180 aatattggaa caccagtaaa agctatttca agcggaaaaa tagttgaagc tggttggagt    240
aattacggag gaggtaatca aataggtctt attgaaaatg atggagtgca tagacaatgg    300
tatatgcatc taagtaaata taatgttaaa gtaggagatt atgtcaaagc tggtcaaata    360
atcggttggt ctggaagcac tggttattct acagcaccac atttacactt ccaaagaatg    420
gttaattcat tttcaaattc aactgcccaa gatccaatgc ctttcttaaa gagcgcagga    480
tatggaaaag caggtggtac agtaactcca acgccgaata caggtgagct cgctgcaaca    540
catgaacatt cagcacaatg gttgaataat tacaaaaaag gatatggtta cggtccttat    600
ccattaggta taaatggcgg tatgcactac ggagttgatt tttttatgaa tattggaaca    660
ccagtaaaag ctatttcaag cggaaaaata gttgaagctg gttggagtaa ttacggagga    720
ggtaatcaaa taggtcttat tgaaaatgat ggagtgcata gacaatggta tatgcatcta    780
agtaaatata atgttaaagt aggagattat gtcaaagctg gtcaaataat cggttggtct    840
ggaagcactg gttattctac agcaccacat ttacacttcc aaagaatggt taattcattt    900
tcaaattcaa ctgcccaaga tccaatgcct ttcttaaaga gcgcaggata tggaaaagca    960
ggtggtacag taactccaac gccgaataca ggttggaaac agaataaaga tggcatttgg    1020
tataaagctg aacatgcttc gttcacagtg acagcaccag agggaattat cacaagatac    1080
aaaggtcctt ggactggtca cccacaagct ggtgtattac aaaaaggtca acgattaaa    1140 tatgatgagg ttcaaaaatt tgacggtcat gtttgggtat cgtgggaaac gtttgagggc    1200
gaaactgtat acatgccggt acgcacatgg gacgctaaaa ctggtaaagt tggtaagttg    1260
tggggcgaaa ttaaataa                                                  1278
```

<210> SEQ ID NO 68
<211> LENGTH: 425
<212> TYPE: PRT
<213> ORGANISM: artificial
<220> FEATURE:
<223> OTHER INFORMATION: artificial construct

<400> SEQUENCE: 68

```
Met Arg Gly Ser His His His His His His Gly Ser Gly Ser Gly Ser
1               5                   10                  15

Gly Ile Glu Gly Arg Ala Ala Thr His Glu His Ser Ala Gln Trp Leu
            20                  25                  30

Asn Asn Tyr Lys Lys Gly Tyr Gly Tyr Gly Pro Tyr Pro Leu Gly Ile
        35                  40                  45

Asn Gly Gly Met His Tyr Gly Val Asp Phe Phe Met Asn Ile Gly Thr
    50                  55                  60

Pro Val Lys Ala Ile Ser Ser Gly Lys Ile Val Glu Ala Gly Trp Ser
65                  70                  75                  80

Asn Tyr Gly Gly Gly Asn Gln Ile Gly Leu Ile Glu Asn Asp Gly Val
                85                  90                  95

His Arg Gln Trp Tyr Met His Leu Ser Lys Tyr Asn Val Lys Val Gly
            100                 105                 110

Asp Tyr Val Lys Ala Gly Gln Ile Ile Gly Trp Ser Gly Ser Thr Gly
        115                 120                 125

Tyr Ser Thr Ala Pro His Leu His Phe Gln Arg Met Val Asn Ser Phe
    130                 135                 140

Ser Asn Ser Thr Ala Gln Asp Pro Met Pro Phe Leu Lys Ser Ala Gly
145                 150                 155                 160
```

Tyr Gly Lys Ala Gly Gly Thr Val Thr Pro Thr Pro Asn Thr Gly Glu
                165                 170                 175

Leu Ala Ala Thr His Glu His Ser Ala Gln Trp Leu Asn Asn Tyr Lys
            180                 185                 190

Lys Gly Tyr Gly Tyr Gly Pro Tyr Pro Leu Gly Ile Asn Gly Gly Met
        195                 200                 205

His Tyr Gly Val Asp Phe Phe Met Asn Ile Gly Thr Pro Val Lys Ala
    210                 215                 220

Ile Ser Ser Gly Lys Ile Val Glu Ala Gly Trp Ser Asn Tyr Gly Gly
225                 230                 235                 240

Gly Asn Gln Ile Gly Leu Ile Glu Asn Asp Gly Val His Arg Gln Trp
                245                 250                 255

Tyr Met His Leu Ser Lys Tyr Asn Val Lys Val Gly Asp Tyr Val Lys
            260                 265                 270

Ala Gly Gln Ile Ile Gly Trp Ser Gly Ser Thr Gly Tyr Ser Thr Ala
        275                 280                 285

Pro His Leu His Phe Gln Arg Met Val Asn Ser Phe Ser Asn Ser Thr
    290                 295                 300

Ala Gln Asp Pro Met Pro Phe Leu Lys Ser Ala Gly Tyr Gly Lys Ala
305                 310                 315                 320

Gly Gly Thr Val Thr Pro Thr Pro Asn Thr Gly Trp Lys Gln Asn Lys
                325                 330                 335

Asp Gly Ile Trp Tyr Lys Ala Glu His Ala Ser Phe Thr Val Thr Ala
            340                 345                 350

Pro Glu Gly Ile Ile Thr Arg Tyr Lys Gly Pro Trp Thr Gly His Pro
        355                 360                 365

Gln Ala Gly Val Leu Gln Lys Gly Gln Thr Ile Lys Tyr Asp Glu Val
    370                 375                 380

Gln Lys Phe Asp Gly His Val Trp Val Ser Trp Glu Thr Phe Glu Gly
385                 390                 395                 400

Glu Thr Val Tyr Met Pro Val Arg Thr Trp Asp Ala Lys Thr Gly Lys
                405                 410                 415

Val Gly Lys Leu Trp Gly Glu Ile Lys
            420                 425

<210> SEQ ID NO 69
<211> LENGTH: 1272
<212> TYPE: DNA
<213> ORGANISM: artificial
<220> FEATURE:
<223> OTHER INFORMATION: artificial construct

<400> SEQUENCE: 69
atgagaggat cgcatcacca tcaccatcac ggatctggct ctggatctgg tatcgaggga      60
agggctgcaa cacatgaaca ttcagcacaa tggttgaata attacaaaaa aggatatggt     120
tacggtcctt atccattagg tataaatggc ggtatgcact acggagttga tttttttatg     180
aatattggaa caccagtaaa agctatttca agcggaaaaa tagttgaagc tggttggagt     240
aattacggag gaggtaatca ataggtcttt attgaaaatg atggagtgca tagacaatgg     300
tatatgcatc taagtaaata taatgttaaa gtaggagatt atgtcaaagc tggtcaaata     360
atcggttggt ctggaagcac tggttattct acagcaccac atttacactt ccaaagaatg     420
gttaattcat tttcaaattc aactgcccaa gatccaatgc ctttcttaaa gagcgcagga     480
tatggaaaag caggtggtac agtaactcca acgccgaata caggtgagct cgctgcaaca     540

```
catgaacatt cagcacaatg gttgaataat tacaaaaaag gatatggtta cggtccttat    600
ccattaggta taaatggcgg tatgcactac ggagttgatt tttttatgaa tattggaaca    660
ccagtaaaag ctatttcaag cggaaaaata gttgaagctg gttggagtaa ttacggagga    720
ggtaatcaaa taggtcttat tgaaaatgat ggagtgcata acaatggta tatgcatcta     780 agtaaatata atgttaaagt aggagattat gtcaaagctg gtcaaataat cggttggtct    840
ggaagcactg gttattctac agcaccacat ttacacttcc aaagaatggt taattcattt    900
tcaaattcaa ctgcccaaga tccaatgcct ttcttaaaga gcgcaggata tggaaaagca    960
ggtggtacag taactccaac gccgaataca ggttggaaaa caaacaaata tggcacacta   1020
tataaatcag agtcagctag cttcacacct aatacagata ataacaag aacgactggt     1080 ccatttagaa gcatgccgca gtcaggagtc ttaaaagcag gtcaaacaat tcattatgat   1140
gaagtgatga acaagacgg tcatgtttgg gtaggttata caggtaacag tggccaacgt    1200
atttacttgc ctgtaagaac atggaataaa tctactaata ctttaggtgt tctttgggga    1260
actataaagt aa                                                       1272
```

<210> SEQ ID NO 70
<211> LENGTH: 423
<212> TYPE: PRT
<213> ORGANISM: artificial
<220> FEATURE:
<223> OTHER INFORMATION: artificial construct

<400> SEQUENCE: 70

```
Met Arg Gly Ser His His His His His His Gly Ser Gly Ser
1               5                   10                  15

Gly Ile Glu Gly Arg Ala Ala Thr His Glu His Ser Ala Gln Trp Leu
            20                  25                  30

Asn Asn Tyr Lys Lys Gly Tyr Gly Tyr Gly Pro Tyr Pro Leu Gly Ile
        35                  40                  45

Asn Gly Gly Met His Tyr Gly Val Asp Phe Phe Met Asn Ile Gly Thr
    50                  55                  60

Pro Val Lys Ala Ile Ser Ser Gly Lys Ile Val Glu Ala Gly Trp Ser
65                  70                  75                  80

Asn Tyr Gly Gly Gly Asn Gln Ile Gly Leu Ile Glu Asn Asp Gly Val
                85                  90                  95

His Arg Gln Trp Tyr Met His Leu Ser Lys Tyr Asn Val Lys Val Gly
            100                 105                 110

Asp Tyr Val Lys Ala Gly Gln Ile Ile Gly Trp Ser Gly Ser Thr Gly
        115                 120                 125

Tyr Ser Thr Ala Pro His Leu His Phe Gln Arg Met Val Asn Ser Phe
    130                 135                 140

Ser Asn Ser Thr Ala Gln Asp Pro Met Pro Phe Leu Lys Ser Ala Gly
145                 150                 155                 160

Tyr Gly Lys Ala Gly Gly Thr Val Thr Pro Thr Pro Asn Thr Gly Glu
                165                 170                 175

Leu Ala Ala Thr His Glu His Ser Ala Gln Trp Leu Asn Asn Tyr Lys
            180                 185                 190

Lys Gly Tyr Gly Tyr Gly Pro Tyr Pro Leu Gly Ile Asn Gly Gly Met
        195                 200                 205

His Tyr Gly Val Asp Phe Phe Met Asn Ile Gly Thr Pro Val Lys Ala
    210                 215                 220
```

| | | | | | | | | | | | | | | |
|---|---|---|---|---|---|---|---|---|---|---|---|---|---|---|
|Ile|Ser|Ser|Gly|Lys|Ile|Val|Glu|Ala|Gly|Trp|Ser|Asn|Tyr|Gly|Gly|
|225| | | |230| | | |235| | | |240| | |

Gly Asn Gln Ile Gly Leu Ile Glu Asn Asp Gly Val His Arg Gln Trp
            245                 250                 255

Tyr Met His Leu Ser Lys Tyr Asn Val Lys Val Gly Asp Tyr Val Lys
        260                 265                 270

Ala Gly Gln Ile Ile Gly Trp Ser Gly Ser Thr Gly Tyr Ser Thr Ala
275                 280                 285

Pro His Leu His Phe Gln Arg Met Val Asn Ser Phe Ser Asn Ser Thr
        290                 295                 300

Ala Gln Asp Pro Met Pro Phe Leu Lys Ser Ala Gly Tyr Gly Lys Ala
305                 310                 315                 320

Gly Gly Thr Val Thr Pro Thr Pro Asn Thr Gly Trp Lys Thr Asn Lys
                325                 330                 335

Tyr Gly Thr Leu Tyr Lys Ser Glu Ser Ala Ser Phe Thr Pro Asn Thr
            340                 345                 350

Asp Ile Ile Thr Arg Thr Thr Gly Pro Phe Arg Ser Met Pro Gln Ser
        355                 360                 365

Gly Val Leu Lys Ala Gly Gln Thr Ile His Tyr Asp Glu Val Met Lys
370                 375                 380

Gln Asp Gly His Val Trp Val Gly Tyr Thr Gly Asn Ser Gly Gln Arg
385                 390                 395                 400

Ile Tyr Leu Pro Val Arg Thr Trp Asn Lys Ser Thr Asn Thr Leu Gly
                405                 410                 415

Val Leu Trp Gly Thr Ile Lys
            420

<210> SEQ ID NO 71
<211> LENGTH: 1278
<212> TYPE: DNA
<213> ORGANISM: artificial
<220> FEATURE:
<223> OTHER INFORMATION: artificial construct

<400> SEQUENCE: 71

| | | |
|---|---|---|
|atgagaggat cgcatcacca tcaccatcac ggatctggct ctggatctgg tatcgaggga|60|
|agggctgcaa cacatgaaca ttcagcacaa tggttgaata attacaaaaa aggatatggt|120|
|tacggtcctt atccattagg tataaatggc ggtatgcact acggagttga ttttttatg|180|
|aatattggaa caccagtaaa agctatttca agcggaaaaa tagttgaagc tggttggagt|240|
|aattacggag aggtaatca ataggtcttt attgaaaatg atggagtgca tagacaatgg|300|
|tatatgcatc taagtaaata taatgttaaa gtaggagatt atgtcaaagc tggtcaaata|360|
|atcggttggt ctggaagcac tggttattct acagcaccac atttacactt ccaagaatg|420|
|gttaattcat tttcaaattc aactgcccaa gatccaatgc ctttcttaaa gagcgcagga|480|
|tatgaaaag caggtggtac agtaactcca acgccgaata caggtgagct cgctgcaaca|540|
|catgaacatt cagcacaatg gttgaataat acaaaaaag gatatggtta cggtccttat|600|
|ccattaggta taaatggcgg tatgcactac ggagttgatt tttatgaa tattggaaca|660|
|ccagtaaaag ctatttcaag cggaaaaata gttgaagctg gttggagtaa ttacggagga|720|
|ggtaatcaaa taggtcttat tgaaaatgat ggagtgcata gacaatggta tatgcatcta|780|
|agtaaatata atgttaaagt aggagattat gtcaaagctg gtcaaataat cggttggtct|840|
|ggaagcactg gttattctac agcaccacat ttacacttcc aaagaatggt taattcattt|900|

-continued

```
tcaaattcaa ctgcccaaga tccaatgcct ttcttaaaga gcgcaggata tggaaaagca    960
ggtggtacag taactccaac gccgaataca ggtggtaaat ctgcaagtaa aataacagtt   1020
ggaagtaaag cgccttataa ccttaaatgg tcaaaggtg cttattttaa tgcgaaaatc   1080
gacggcttag gtgctacttc agccactaga tacggtgata atcgtactaa ctatagattc   1140
gatgttggac aggctgtata cgcgcctgga acattaatat atgtgtttga aattatagat   1200
ggttggtgtc gcatttattg gaacaatcat aatgagtgga tatggcatga gagattgatt   1260
gtgaaagaag tgttttaa                                                 1278
```

<210> SEQ ID NO 72
<211> LENGTH: 425
<212> TYPE: PRT
<213> ORGANISM: artificial
<220> FEATURE:
<223> OTHER INFORMATION: artificial construct

<400> SEQUENCE: 72

```
Met Arg Gly Ser His His His His His Gly Ser Gly Ser Gly Ser
1               5                   10                  15

Gly Ile Glu Gly Arg Ala Ala Thr His Glu His Ser Ala Gln Trp Leu
            20                  25                  30

Asn Asn Tyr Lys Lys Gly Tyr Gly Tyr Gly Pro Tyr Pro Leu Gly Ile
        35                  40                  45

Asn Gly Gly Met His Tyr Gly Val Asp Phe Phe Met Asn Ile Gly Thr
    50                  55                  60

Pro Val Lys Ala Ile Ser Ser Gly Lys Ile Val Glu Ala Gly Trp Ser
65                  70                  75                  80

Asn Tyr Gly Gly Gly Asn Gln Ile Gly Leu Ile Glu Asn Asp Gly Val
                85                  90                  95

His Arg Gln Trp Tyr Met His Leu Ser Lys Tyr Asn Val Lys Val Gly
            100                 105                 110

Asp Tyr Val Lys Ala Gly Gln Ile Ile Gly Trp Ser Gly Ser Thr Gly
        115                 120                 125

Tyr Ser Thr Ala Pro His Leu His Phe Gln Arg Met Val Asn Ser Phe
    130                 135                 140

Ser Asn Ser Thr Ala Gln Asp Pro Met Pro Phe Leu Lys Ser Ala Gly
145                 150                 155                 160

Tyr Gly Lys Ala Gly Gly Thr Val Thr Pro Thr Pro Asn Thr Gly Glu
                165                 170                 175

Leu Ala Thr His Glu His Ser Ala Gln Trp Leu Asn Asn Tyr Lys
            180                 185                 190

Lys Gly Tyr Gly Tyr Gly Pro Tyr Pro Leu Gly Ile Asn Gly Gly Met
        195                 200                 205

His Tyr Gly Val Asp Phe Phe Met Asn Ile Gly Thr Pro Val Lys Ala
    210                 215                 220

Ile Ser Ser Gly Lys Ile Val Glu Ala Gly Trp Ser Asn Tyr Gly Gly
225                 230                 235                 240

Gly Asn Gln Ile Gly Leu Ile Glu Asn Asp Gly Val His Arg Gln Trp
                245                 250                 255

Tyr Met His Leu Ser Lys Tyr Asn Val Lys Val Gly Asp Tyr Val Lys
            260                 265                 270

Ala Gly Gln Ile Ile Gly Trp Ser Gly Ser Thr Gly Tyr Ser Thr Ala
        275                 280                 285

Pro His Leu His Phe Gln Arg Met Val Asn Ser Phe Ser Asn Ser Thr
```

```
                   290                 295                 300
Ala Gln Asp Pro Met Pro Phe Leu Lys Ser Ala Gly Tyr Gly Lys Ala
305                 310                 315                 320

Gly Gly Thr Val Thr Pro Thr Pro Asn Thr Gly Lys Ser Ala Ser
                325                 330                 335

Lys Ile Thr Val Gly Ser Lys Ala Pro Tyr Asn Leu Lys Trp Ser Lys
                340                 345                 350

Gly Ala Tyr Phe Asn Ala Lys Ile Asp Gly Leu Gly Ala Thr Ser Ala
                355                 360                 365

Thr Arg Tyr Gly Asp Asn Arg Thr Asn Tyr Arg Phe Asp Val Gly Gln
                370                 375                 380

Ala Val Tyr Ala Pro Gly Thr Leu Ile Tyr Val Phe Glu Ile Ile Asp
385                 390                 395                 400

Gly Trp Cys Arg Ile Tyr Trp Asn Asn His Asn Glu Trp Ile Trp His
                405                 410                 415

Glu Arg Leu Ile Val Lys Glu Val Phe
                420                 425

<210> SEQ ID NO 73
<211> LENGTH: 63
<212> TYPE: DNA
<213> ORGANISM: artificial
<220> FEATURE:
<223> OTHER INFORMATION: artificial his-tag

<400> SEQUENCE: 73
atgagaggat cgcatcacca tcaccatcac ggatctggct ctggatctgg tatcgaggga    60
agg                                                                  63

<210> SEQ ID NO 74
<211> LENGTH: 21
<212> TYPE: PRT
<213> ORGANISM: artificial
<220> FEATURE:
<223> OTHER INFORMATION: artificial Hist-tag

<400> SEQUENCE: 74

Met Arg Gly Ser His His His His His His Gly Ser Gly Ser Gly Ser
1               5                   10                  15

Gly Ile Glu Gly Arg
            20
```

US 9,789,167 B2

POLYPEPTIDE MIXES WITH ANTIBACTERIAL ACTIVITY

CROSS REFERENCE TO RELATED APPLICATION

This application is a 35 U.S.C. §371 national phase application of PCT/NL2013/050344, which was filed May 7, 2013, and claims the benefit of U.S. provisional patent application No. 61/643,417 filed May 7, 2012, and European patent application No. 12166977.4 filed May 7, 2012, all of which are incorporated herein by reference as if fully set forth.

The sequence listing filed with this application, titled "Sequence Listing," having a file size of 167,269 bytes, and created Nov. 7, 2014 is incorporated herein by reference as if fully set forth.

FIELD OF THE INVENTION

The invention relates to the field of microbiology, specifically to a combination of a source of a first enzymatic active domain and a source of a second enzymatic active domain, a polypeptide, a polynucleotide and to a composition comprising said combination, polypeptide and/or polynucleotide. The invention further relates to a composition comprising said combination, polypeptide and/or polynucleotide for use as a medicament, to the use of said composition, polypeptide and/or polynucleotide as an antimicrobial agent and to a method for controlling microbial contamination in a food- or feed product, on and/or in food- or feed processing equipment, on and/or in food- or feed containers.

BACKGROUND OF THE INVENTION

*Staphylococcus aureus* is a major human pathogen frequently causing serious infectious diseases and food poisoning. Its treatment becomes more and more difficult because of emerging antibiotic resistant strains. Endolysins from phages infecting *Staphylococcus aureus* have been shown to potentially control these pathogens to a certain extent and can be used for their specific detection. In most cases, major obstacles in the application of endolysins targeting *Staphylococcus* species are low enzyme activity, difficult production in large quantities and/or protein stability.

Accordingly, there is still a need for new antimicrobials with improved characteristics on for example antimicrobial activity and/or stability.

DESCRIPTION OF THE INVENTION

In a first aspect, the present invention provides a combination of a source of a first enzymatic active domain and a source of a second enzymatic active domain, wherein said first and second enzymatic active domains exhibit distinct target bond specificities and are comprised on a distinct first and second polypeptide, i.e. said first enzymatic active domain is comprised on a first polypeptide and said second enzymatic domain is comprised on a second polypeptide, wherein said first and second polypeptide each have a distinct amino acid sequence. In addition, the present invention provides a combination of a source of a first enzymatic active domain, a source of a second enzymatic active domain and a source of a third enzymatic active domain, wherein said first, second and third enzymatic active domain exhibit distinct target bond specificities and are comprised on a distinct first, second and third polypeptide, i.e. said first enzymatic active domain is comprised on a first polypeptide, said second enzymatic domain is comprised on a second polypeptide, and said third enzymatic domain is comprised on a third polypeptide, wherein said first, second and third polypeptide each have a distinct amino acid sequence. Furthermore, the present invention provides a combination of a source of a first enzymatic active domain, a source of a second enzymatic active domain, a source of a third enzymatic active domain, and a source of a further enzymatic active domain, wherein said first, second, third and further enzymatic active domain exhibit distinct target bond specificities and are comprised on a distinct first, second, third and further polypeptide, i.e. said first enzymatic active domain is comprised on a first polypeptide, said second enzymatic domain is comprised on a second polypeptide, said third enzymatic domain is comprised on a third polypeptide, and said further enzymatic active domain is comprised on a further polypeptide, wherein said first, second, third and further polypeptide each have a distinct amino acid sequence. A further enzymatic active domain is meant herein as a fourth, fifth, sixth, seventh, eighth, ninth, tenth or more enzymatic active domain, preferably a fourth enzymatic active domain. A further polypeptide is meant herein as a fourth, fifth, sixth, seventh, eighth, ninth, tenth or more polypeptide, preferably a fourth polypeptide.

Most native *Staphylococcus* bacteriophage endolysins exhibiting peptidoglycan hydrolase activity consist of a C-terminal cell wall-binding domain (CBD), a central N-acetylmuramoyl-L-Alanine amidase domain, and an N-terminal Alanyl-glycyl endopeptidase domain with cysteine, histidine-dependent amidohydrolases/peptidase (CHAP) homology, or in case of Ply2638, of an N-terminal glycyl-glycine endopeptidase domain with Peptidase_M23 homology, the latter three domains exhibiting peptidoglycan hydrolase activity each with distinct target bond specificity and generally named herein as enzymatically active domains. Within the present invention, a first enzymatic domain according to the present invention has catalytic activity to hydrolyse a specific target bond, which is different from the target bond hydrolysed by a second and optionally a third and/or further enzymatic active domain according to the present invention. Furthermore, within the present invention, a second enzymatic domain according to the present invention has catalytic activity to hydrolyse a specific target bond, which is different from the target bond hydrolysed by a first and optionally a third and/or further enzymatic active domain according to the present invention.

The inventors surprisingly found that simultaneous application of two or more enzymatically active domains with distinct target bond specificities confer synergistic effects. Surprisingly, this works not only when enzymatically active domains with different specificities are located on the same molecule as in native *Staphylococcus* endolysins, but works also when the enzymatically active domains with different specificities are separated on distinct polypeptides.

The benefit of having distinct enzymatic active domains located on separate individual polypeptides is that the resulting polypeptides are smaller which can be more easily produced. Furthermore, these smaller polypeptides have better diffusion properties in specific environments and can be more resistant to degradation and feature higher thermostability. Another advantage is that independent distinct enzymatic active domains located on separate distinct polypeptide molecules can be mixed and pooled in variable compositions, at a ratio that is best suited to hydrolyse the specific bacterial target cells. The combination according to the invention can be supplemented and/or complemented by the use of virtually any functional enzymatic active domain with virtually any target bond specificity from many different origins including phage lysins, bacteriocins, autolysins, or any other cell wall lytic enzymes.

Within the context of the present invention 'a combination' means that a source of a first enzymatic active domain and a source of a second enzymatic active domain are contemplated and encompassed. In addition, within the context of the present invention 'a combination' means that a source of a first enzymatic active domain, a source of a second enzymatic active domain and optionally a source of a third and/or further enzymatic active domain are contemplated and encompassed. Each source may be together or present together or combined together or physically in contact with the other source forming one single composition. Each source may alternatively be comprised within a distinct composition. However the invention provides the insight that both sources of a first and a second enzymatic active domain are needed or are used in order to get an effect of the present invention as defined herein. If each source is not present in a same single composition, each source and/or each distinct composition comprising a source of a combination according to the present invention may be used sequentially or simultaneously.

'A source of a first enzymatic active domain', 'a source of a second enzymatic active domain', 'a source of a third enzymatic active domain' and 'a source of a further enzymatic active domain' preferably comprises a protein-based source, i.e. a polypeptide, a protein, digest of a protein and/or fragment of a protein or digest, or a source not being protein based, i.e. a nucleic acid encoding a protein or derived peptide or protein fragment. Below we defined preferred sources of a first enzymatic active domain, a source of a second enzymatic active domain, a source of a third enzymatic active domain and a source of a further enzymatic active domain that are encompassed by the invention. Since the invention relates to a combination of a source of a first enzymatic active domain, a source of a second enzymatic active domain and optionally a source of a third and/or further enzymatic active domain, each of the sources of a first enzymatic active domain defined herein may be combined with each of the sources of a second and optionally third and/or further enzymatic active domain defined herein. It is also encompassed by the present invention to use a combination of a source of a first enzymatic active domain being protein-based with a source of a second and optionally a third and/or further enzymatic active domain being not protein-based, and vice versa.

'An enzymatic active domain' is defined herein is a domain having lytic activity, preferably exhibiting peptidoglycan hydrolase activity. Lytic activity of a first, second, third and/or further enzymatic active domain according to the present invention comprised on a distinct first, second, third and/or further polypeptide according to the present invention can be assessed by methods well known by the person skilled in the art. In an embodiment, lytic activity is assessed spectrophotometrically by measuring the drop in turbidity of substrate cell suspensions. Turbidity is assessed by measuring optical density at a wavelength of 595 nm, typically a culture as turbid when it exhibits an optical density of at least 0.3 OD at a wavelength of 595 nm. Preferably, lytic activity is assessed spectrophotometrically measuring the drop in turbidity of a S. aureus suspension, wherein turbidity is quantified by measuring $OD_{595}$ spectrophotometrically (Libra S22, Biochrom). More preferably, 200 nM of a first, second and/or third polypeptide as identified herein is incubated together with an S. aureus suspension having an initial $OD_{595}$ of 1±0.05, as assessed spectrophotometrically (Libra S22, Biochrom), in PBS buffer pH 7.4, 120 mM sodium chloride for 30 min at 37° C. The drop in turbidity is calculated by subtracting the $OD_{595}$ after 30 min of incubation from the $OD_{595}$ before 30 min of incubation. Within the context of the invention a first, second and/or third polypeptide will be said to have lytic activity if, when using this assay, a drop in turbidity of at least 10, 20, 30, 40, 50 or 60% is detected. Preferably, a drop in turbidity of at least 70% is detected. Preferably, the invention relates to a first, second, third and/or further polypeptide which exhibits a lytic activity of at least 30, 40, 50, 60, 70, 80, 90, 100, 150 or 200% or more of a lytic activity of S. aureus bacteriophage Φ2638a endolysin (Ply2638 endolysin identified by SEQ ID NO: 2) encoded by SEQ ID NO: 1.

'Exhibit distinct target bond specificities' is meant herein as exhibiting enzymatic activity against a target bond by any of a first, second, third or further enzymatic active domain according to the present invention which is distinct from the target bond to which any of the other of said first, second, third or further enzymatic active domain exhibits enzymatic activity.

'Comprised on distinct polypeptides' is meant herein as any of said first, second and optionally third and/or further enzymatic active domain is comprised on a polypeptide which is distinct from the polypeptide that any of the other of said first, second and optionally third and/or further enzymatic active domain is comprised on.

A polypeptide according to the present invention preferably is an isolated polypeptide. A nucleic acid according to the present invention preferably is an isolated nucleic acid. A nucleic acid construct according to the present invention preferably is an isolated nucleic acid construct.

In a preferred embodiment, a polypeptide according to present invention comprises a sequence encoding a tag for ease of purification. Preferably, said tag is selected from, but is not limited to, the group consisting of a FLAG-tag, poly(His)-tag, HA-tag and Myc-tag. More preferably said tag is a 6xHis-tag. Even more preferably, said tag is an N-terminal 6xHis-tag (indicated herein as HXa) identical to SEQ ID NO: 74 and encoded by SEQ ID NO: 73).

Preferably, a distinct target bond according to the present invention is an essential bond in a peptidoglycan layer of a bacterial cell, preferably said bacterial cell is a *Staphylococcus*. An essential bond in a peptidoglycan layer of a gram-positive bacterial cell is defined herein as a linkage within said peptidoglycan that is essential for said peptidoglycan to provide said bacterial cell shape and a rigid structure resistance to osmotic shock. Preferably, said essential bond in a peptidoglycan layer of a gram-positive bacterial cell is a bond between a D-alanine of the stem peptide and a glycine of the cross-bridge peptide (defined herein also as a bond between an N-terminal alanine and a glycine), a bond in a pentaglycin cross-bridge (defined herein also as a pentaglycin bridge glycyl-glycyl bond, a bond between an N-acetylmuramoyl and an L-alanine or a bond between an N-acetylmuramine and a N-acetylglucosamine or between a N-acetylglucosamine and an N-acetylmuramine (FIG. 1). Other preferred essential bonds in a peptidoglycan layer of a gram-positive bacterial cell are a bond in a gamma-glutamyl stem peptide, a bond between a L-Alanyl-iso-D-glutamic acid in a stem peptide and a bond between an iso-D-glutamic acid-L-Lysine in a stem peptide.

Preferably, a first, a second and optionally a third and/or further enzymatic active domain according to the present invention is a domain selected from the group consisting of a cysteine, histidine-dependent amidohydrolases/peptidase (CHAP) domain, an endopeptidase domain, and an amidase domain. Moreover, preferably, said first, second, third and/or further enzymatic active domain is a domain selected from the group consisting of a cysteine, histidine-dependent amidohydrolases/peptidase (CHAP) domain, an endopeptidase domain, an amidase domain, and a glycosylhydrolase domain. Said glycosylhydrolase domain can be a muramidase domain or a glycosaminidase domain.

Preferably, said CHAP domain cleaves a bond between an N-terminal Alanyl and a glycyl within a peptidoglycan layer. More preferably, said CHAP domain specifically cleaves a bond between an N-terminal Alanyl and a glycyl within a peptidoglycan layer. Preferably, said endopeptidase domain cleaves pentaglycin bridge glycyl-glycyl bond within a peptidoglycan layer. More preferably, said endopeptidase domain specifically cleaves pentaglycin bridge glycyl-glycyl bond within a peptidoglycan layer. Preferably, said amidase domain cleaves a bond between a central N-acetylmuramoyl and an L-Alanine within a peptidoglycan layer. More preferably, said amidase domain specifically cleaves a bond between a central N-acetylmuramoyl and an L-Alanine within a peptidoglycan layer. Preferably, said muramidase domain cleaves a bond between an N-acetylmuramine and a N-acetylglucosamine within a peptidoglycan layer. More preferably, said muramidase domain specifically cleaves a bond between an N-acetylmuramine and a N-acetylglucosamine within a peptidoglycan layer. Preferably, said glucosaminidase domain cleaves a bond between a N-acetylglucosamine and an N-acetylmuramine within a peptidoglycan layer. More preferably, said glucosaminidase domain specifically cleaves a bond between a N-acetylglucosamine and an N-acetylmuramine within a peptidoglycan layer. Preferably said peptidoglycan layer is of a gram positive bacterial cell, preferably of a *Staphylococcus*, most preferably of a *Staphylococcus aureus*. Preferably, the cleavage of a bond by an enzymatic active domain as defined herein is specific if such a bond is hydrolysed at least 2, 10, 50 or a 100 times more efficient with said enzymatic active domain as compared to the hydrolyses of any other bond as defined herein above with said enzymatic active domain.

Preferably, a CHAP domain encompassed within the present invention originates from *Staphylococcus* phage K and/or *Staphylococcus* phage Twort. Preferably, a CHAP domain encompassed within the present invention, is a domain that has at least 80, 81, 82, 83, 84, 85, 86, 87, 88, 89, 90, 91, 92, 93, 94, 95, 96, 97, 98, 99 or 100% identity with SEQ ID NO: 10 or 12. Preferably, an endopeptidase domain encompassed within the present invention originates from *S. aureus* bacteriophage Φ2638a and/or *S. simulans*. Preferably, an endopeptidase domain encompassed by the present invention has at least 80, 81, 82, 83, 84, 85, 86, 87, 88, 89, 90, 91, 92, 93, 94, 95, 96, 97, 98, 99 or 100% identity with SEQ ID NO: 14 or 16. Preferably, an amidase domain encompassed within the present invention originates from *S. aureus* bacteriophage Φ2638a. Preferably an amidase domain of the present invention has at least 80, 81, 82, 83, 84, 85, 86, 87, 88, 89, 90, 91, 92, 93, 94, 95, 96, 97, 98, 99 or 100% identity with SEQ ID NO: 18.

Preferably, a first, second, third and/or further polypeptide according to the present invention comprises a different multiplicity of a first, second, third and/or further enzymatic active domain according to the present invention. A "multiplicity" is herein defined as a number of copies. A "different multiplicity" is defined herein as a multiplicity or number of copies of a specific enzymatic active domain of the invention, i.e. a first, second, third or further enzymatic active domain as identified herein, comprised within a specific polypeptide of the invention, i.e. a first, second, third or further polypeptide as identified herein, to be different form a multiplicity or number of copies of that same enzymatic active domain within another polypeptide of the combination of the invention. For example, a combination of the present invention comprises a first polypeptide comprising a specific number of copies of a first enzymatic active domain, and a second polypeptide comprising a different number of copies of said first enzymatic active domain. Furthermore, said first polypeptide of said exemplified combination of the present invention may further comprise a specific number of copies of second enzymatic active domain, which is different from the number of copies of said second enzymatic active domain as comprised on said second polypeptide of said combination. Furthermore, any further polypeptide of said exemplified combination of the present invention may comprise a number of copies of further enzymatic active domain, which is different from the number of copies of said further enzymatic active domain as comprised on said first and second polypeptide of said combination. Although a combination of distinct polypeptides each comprising a single distinct enzymatic active domain showed synergistic lytic activity as compared to the lytic activity of each separate polypeptide, it was surprisingly found by the present inventors that polypeptides comprising a multiplicity of enzymatic active domains show superior lytic activity as compared to polypeptides comprising a single enzymatic active domain.

Moreover, a combination of distinct enzymatic domains on distinct polypeptides wherein at least one of said distinct polypeptides comprises a multiplicity of enzymatic active domains was found superior over a combination wherein all said distinct polypeptides comprise a single distinct enzymatic active domain. Moreover, a combination according to the present invention, wherein a first, second, third and/or further polypeptide according to the present invention comprise a multiplicity of a first, second, third and/or further enzymatic active domain according to the present invention, respectively, was found superior over a combination according to the present invention, wherein said first, second, third and/or further polypeptide comprise a single copy of said first, second, third and/or further enzymatic active domain, respectively, and preferably wherein said multiplicity, as defined herein, is 2, i.e. a duplicate. In a preferred embodiment, the synergistic effect of a combination according to the present invention, wherein a first, second, third and/or further polypeptide according to the present invention comprise a multiplicity of a first, second, third and/or further enzymatic active domain according to the present invention, respectively, was found superior over a combination according to the present invention, wherein said first, second, third and further polypeptide comprise a single copy of said first, second, third and further enzymatic active domain, respectively, and preferably wherein said multiplicity, as defined herein below, is 2, i.e. a duplicate.

Preferably, a first and/or second polypeptide according to the present invention comprises a different multiplicity of a first and/or second enzymatic active domain according to the present invention. Multiplicity of said first and second domain is defined as previously herein as a number of copies, preferably indicated by k, l, n and p, of said first and second domain indicated as follows:

k indicates the number of copies of said first enzymatic active domain on said first polypeptide;

l indicates the number of copies of said second enzymatic active domain on said first polypeptide;
n indicates the number of copies of said first enzymatic active domain on said second polypeptide;
p indicates the number of copies of said second enzymatic active domain on said second polypeptide;
and wherein k and p are independent integers from 1-10, 1-9, 1-8, 1-7, 1-6, 1-5, 1-4, 1-3, or preferably 1-2, and l and n are independent integers from 0-10, 0-9, 0-8, 0-7, 0-6, 0-5, 0-4, 0-3, or preferably 0-2, and wherein k is a different integer than n and/or l is a different integer than p, most preferably k and p are 2 and l and n are 0.

Preferably, a first, second and third polypeptide of the present invention comprise a different multiplicity of a first, second and third enzymatic active domain according to the present invention.

Multiplicity of said first, second and third domain is defined as previously herein as a number of copies, preferably indicated by k, l, m, n, p, q, r, s and t, of said first, second and third domain indicated as follows:
k indicates the number of copies of said first enzymatic active domain on said first polypeptide;
l indicates the number of copies of said second enzymatic active domain on said first polypeptide;
m indicates the number of copies of said third enzymatic active domain on said first polypeptide;
n indicates the number of copies of said first enzymatic active domain on said second polypeptide;
p indicates the number of copies of said second enzymatic active domain on said second polypeptide;
q indicates the number of copies of said third enzymatic active domain on said second polypeptide;
r indicates the number of copies of said first enzymatic active domain on said third polypeptide;
s indicates the number of copies of said second enzymatic active domain on said third polypeptide;
t indicates the number of copies of said third enzymatic active domain on said third polypeptide;
and wherein k, p and t are independent integers from 1-10, 1-9, 1-8, 1-7, 1-6, 1-5, 1-4, 1-3, or preferably 1-2, and l, m, n, q, r, and s are independent integers from 0-10, 0-9, 0-8, 0-7, 0-6, 0-5, 0-4, 0-3, or preferably 0-2, and wherein k is a different integer than n and/or r, and/or l is a different integer than p and/or s, and/or t is a different integer than m or q, most preferably k, p and t are 2 and l, m, n, q, r, and s are 0.

Preferably, a first, second, third and further polypeptide of the present invention comprise a different multiplicity of a first, second, third and further enzymatic active domain according to the present invention. Multiplicity of said further enzymatic active domain in view of said first, second and third enzymatic active domain is to be construed herein in an analogous manner as defined herein above for a first, second and third enzymatic active domain.

Preferably a first, second, third or further polypeptide according to the present invention has a length of at least 140, 150, 160, 170, 180, 190, 200, 210, 220, 230, 240, 250, 260, 270, 280, 290, 300, 310, 320 or 330 amino acids and/or a length of at most 850, 800, 750, 700, 650, 600, 550, 500, 490, 480, 470, 460, 450, 440, 430, 420, 410, 400, 390, 380 or 370 amino acids. More preferably, a first, second or third polypeptide according to the present invention has a length of 140-850, 140-800, 140-750, 140-700, 140-650, 140-600, 140-550 140-500, 140-490, 140-480, 140-470, 140-460, 140-450, 140-440, 140-430, 140-420, 140-410, 140-400, 140-390, 140-380, 140-370, 150-850, 160-850, 170-850, 180-850, 190-850, 200-850, 210-850, 220-850, 230-850, 240-850, 250-850, 260-850, 270-850, 280-850, 290-850, 300-850, 310-850, 320-850 or 330-850 amino acids.

Preferably a first and second polypeptide according to the present invention each have a length of at least 140, 150, 160, 170, 180, 190, 200, 210, 220, 230, 240, 250, 260, 270, 280, 290, 300, 310, 320 or 330 amino acids and/or a length of at most 800, 850, 700, 650, 600, 550, 500, 490, 480, 470, 460, 450, 440, 430, 420, 410, 400, 390, 380 or 370 amino acids. More preferably, a first and second polypeptide according to the present invention each have a length of 140-850, 140-800, 140-750, 140-700, 140-650, 140-600, 140-550 140-500, 140-490, 140-480, 140-470, 140-460, 140-450, 140-440, 140-430, 140-420, 140-410, 140-400, 140-390, 140-380, 140-370, 150-850, 160-850, 170-850, 180-850, 190-850, 200-850, 210-850, 220-850, 230-850, 240-850, 250-850, 260-850, 270-850, 280-850, 290-850, 300-850, 310-850, 320-850 or 330-850 amino acids.

Preferably a first, second and third polypeptide according to the present invention each have a length of at least 140, 150, 160, 170, 180, 190, 200, 210, 220, 230, 240, 250, 260, 270, 280, 290, 300, 310, 320 or 330 amino acids and/or a length of at most 800, 850, 700, 650, 600, 550, 500, 490, 480, 470, 460, 450, 440, 430, 420, 410, 400, 390, 380 or 370 amino acids. More preferably, a first, second and third polypeptides according to the present invention each have a length of 140-850, 140-800, 140-750, 140-700, 140-650, 140-600, 140-550 140-500, 140-490, 140-480, 140-470, 140-460, 140-450, 140-440, 140-430, 140-420, 140-410, 140-400, 140-390, 140-380, 140-370, 150-850, 160-850, 170-850, 180-850, 190-850, 200-850, 210-850, 220-850, 230-850, 240-850, 250-850, 260-850, 270-850, 280-850, 290-850, 300-850, 310-850, 320-850 or 330-850 amino acids.

Preferably a first, second, third and further polypeptide according to the present invention each have a length of at least 140, 150, 160, 170, 180, 190, 200, 210, 220, 230, 240, 250, 260, 270, 280, 290, 300, 310, 320 or 330 amino acids and/or a length of at most 800, 850, 700, 650, 600, 550, 500, 490, 480, 470, 460, 450, 440, 430, 420, 410, 400, 390, 380 or 370 amino acids. More preferably, a first, second, third and further polypeptides according to the present invention each have a length of 140-850, 140-800, 140-750, 140-700, 140-650, 140-600, 140-550 140-500, 140-490, 140-480, 140-470, 140-460, 140-450, 140-440, 140-430, 140-420, 140-410, 140-400, 140-390, 140-380, 140-370, 150-850, 160-850, 170-850, 180-850, 190-850, 200-850, 210-850, 220-850, 230-850, 240-850, 250-850, 260-850, 270-850, 280-850, 290-850, 300-850, 310-850, 320-850 or 330-850 amino acids.

An embodiment provides a combination of a source of a first and a second enzymatic active domain according to the present invention, wherein said first and second enzymatic active domains are comprised on distinct, first and second polypeptides of the present invention, wherein said first polypeptide is free of said second enzymatic active domain and said second polypeptide is free of said first enzymatic active domain. Moreover, provided is a combination according to the present invention, wherein 1 and n are 0.

Another embodiment provides a combination of a source of a first, second and third enzymatic active domain according to the present invention, wherein said first, second and third enzymatic active domains are comprised on distinct, first, second and third polypeptides, wherein said first polypeptide is free of said second and third enzymatic active domain, said second polypeptide is free of said first and third enzymatic active domain, and said third polypeptide is free of said first and second enzymatic active domain. Moreover, provided is a combination according to the present invention, wherein l, m, n, q, r and s are 0. Even more preferably, the present invention provides a combination according to the present invention, wherein l, m, n, q, r and s are 0 and k, p and t are 2.

Another embodiment provides a combination of a source of a first, second, third and further enzymatic active domain according to the present invention, wherein said first, second, third and further enzymatic active domains are comprised on a distinct, first, second, third and further polypeptide, respectively, wherein preferably said first polypeptide is free of said second, third and further enzymatic active domain;

preferably said second polypeptide is free of said first, third and further enzymatic active domain;

preferably said third polypeptide is free of said first, second and further enzymatic active domain; and, preferably said further polypeptide is free of said first, second and third enzymatic active domain.

Preferably said first, second, third and further enzymatic active domain are comprised within said first, second, third and further polypeptide, respectively, in duplicate, i.e. wherein the multiplicity as identified herein is 2. Also encompassed is a combination according to the present invention, wherein a first, second and/or third polypeptide according to the present invention are not free of a first, second and/or third enzymatic active domain according to the present invention, but said first, second and/or third polypeptide differ in multiplicity of said first, second and/or third enzymatic active domain. Moreover, encompassed is a combination according to the present invention, wherein at least one of k, l, m, n p, q, r, s or t is 2 and wherein any of the other k, l, m, n p, q, r, s and/or t is 1 or 0.

Preferred is a combination according to the present invention, wherein a polypeptide according to the present invention further comprises a cell wall-binding domain. Moreover, a first, second, third and/or further polypeptide according to the present invention each comprising at least one enzymatic active domain as defined herein, further comprise a cell wall-binding domain. A cell wall-binding domain of the present invention is defined as an element, preferably a polypeptide within said distinct polypeptide, that directs said distinct polypeptide to the bacterial wall of the cell. Preferably, a cell wall-binding domain of the present invention is an element, preferably a polypeptide within said distinct polypeptide, that directs said distinct polypeptide to the peptidoglycan cell wall of a gram-positive bacterial cell, preferably the peptidoglycan cell wall of a *Staphylococcus* bacterial cell.

Binding of a domain to the peptidoglycan cell wall of *Staphylococcus* genera may be assessed using assays well known to the person skilled in the art. In a preferred embodiment, an immunohistochemical technique and/or a gene fusion technique resulting in labelled constructs are used for assessing specific binding of peptides, polypeptides or proteins to the peptidoglycan cell wall of *Staphylococcus* genera. Quantification methods of signals used in the above mentioned immunohistochemical or fusion techniques are well known in the art.

In one embodiment, *Staphylococcus* peptidoglycan cell wall-binding is quantified using a fluorescent fusion construct comprising a cell wall-domain of interest. Such a cell wall-binding assay is described in detail by Loessner et al (Molecular Microbiology 2002, 44(2): 335-349). In this assay a solution comprising said fluorescent fusion construct or a negative control, preferably Green Fluorescent Protein (GFP), is subjected to *Staphylococcus* cells, preferably *S.* *aureus* cells, more preferably *S.* *aureus* BB255 for an indicated time period where after the cells are sedimented by centrifugation together with the bound fluorescent fusion constructs. The fluorescent signal of the *Staphylococcus* cells exposed to a fluorescent fusion construct subtracted by the fluorescence signal of the *Staphylococcus* cells exposed to a negative control, preferably GFP, is a measure for cell binding as meant in this disclosure. Preferably, within the context of the invention, a domain is said to bind the peptidoglycan cell wall of *Staphylococcus* genera when using this assay an increase in fluorescent signal of the sedimented cells above the negative control as defined herein is detected. Preferably, the invention relates to a cell wall-binding domain which exhibits binding as defined herein of at least 50, 60, 70, 80, 90 or 100%, 150 or 200% of peptidoglycan cell wall-binding of *S. aureus* bacteriophage Φ2638a endolysin (Ply2638 endolysin defined by SEQ ID NO: 2) encoded by SEQ ID NO: 1.

A cell wall-binding domain encompassed within the present invention may be any cell wall-binding domain known by the person skilled in the art. A preferred cell wall-binding domain of the present invention is a cell wall-binding domain having at least 80, 81, 82, 83, 84, 85, 86, 87, 88, 89, 90, 91, 92, 93, 94, 95, 96, 97, 98, 99 or 100% identity with the cell wall binding domain of S. *Simulans* lysostaphin defined herein by SEQ ID NO: 4 and encoded by SEQ ID NO: 3. Also preferred is a cell wall-binding domain isolated from a native *Staphylococcus* bacteriophage endolysin. Preferably, a cell wall-binding domain of the present invention has at least 80, 81, 82, 83, 84, 85, 86, 87, 88, 89, 90, 91, 92, 93, 94, 95, 96, 97, 98, 99 or 100% identity with the cell wall-binding domain of *S. aureus* bacteriophage Φ2638a endolysin defined herein by SEQ ID NO: 6 and encoded by SEQ ID NO: 5. Also preferred is a cell wall-binding domain isolated from a native *Staphylococcus aureus* phage phiNM3 endolysin. Preferably, a cell wall-binding domain of the present invention has at least 80, 81, 82, 83, 84, 85, 86, 87, 88, 89, 90, 91, 92, 93, 94, 95, 96, 97, 98, 99 or 100% identity with the cell wall-binding domain of *S. aureus* phage phiNM3 endolysin defined herein by SEQ ID NO: 8 and encoded by SEQ ID NO: 7.

Preferably, a cell wall-binding domain according to the present invention is located on the C-terminal side of the enzymatic active domain with said distinct first, second, third and/or further polypeptide. It is to be understood further that encompassed is a combination according to the present invention, wherein a distinct first, second and optionally third and/or further polypeptide according to the present invention do not only differ in their specific enzymatic active domains, but also in their specific cell wall-binding domain. Even a combination according to the present invention, wherein a distinct first, second and optionally third polypeptide according to the present invention is free of a cell wall-binding domain according to the present invention is within the scope of the present invention. Furthermore, a combination according to the present invention, wherein one or two of a first, second and optionally third and/or further polypeptides according to the present invention are free of a cell wall binding domain is within the scope of the present invention.

Preferred is a combination according to the present invention, wherein a first, second, third and/or further polypeptide according to the present invention is a polypeptide that has at least 80, 81, 82, 83, 84, 85, 86, 87, 88, 89, 90, 91, 92, 93, 94, 95, 96, 97, 98, 99 or 100% identity with a polypeptide selected from the group consisting of SEQ ID NO: 26, 28, 30, 32, 34, 36, 38, 40, 42, 44, 46, 48, 50, 52, 54, 56, 58, 60, 62, 64, 66, 68, 70 or 72.

In a preferred embodiment, the present invention provides a combination of a source of first enzymatic active domain and a second enzymatic active domain, wherein said first and second enzymatic active domains are comprised on distinct first and second polypeptides, and wherein said first enzymatic active domain is a cysteine, histidine-dependent amidohydrolases/peptidase domain and said second enzymatic active domain is an endopeptidase domain or wherein said first enzymatic active domain is a cysteine, histidine-dependent amidohydrolases/peptidase domain and said second enzymatic active domain is amidase domain or wherein said first enzymatic active domain is an endopeptidase domain and said second enzymatic active domain is amidase domain, wherein said distinct first and second each further comprises a cell wall-binding domain, and wherein each of said distinct first and second polypeptides comprises a multiplicity of said first or second enzymatic active domain, preferably said multiplicity being 2, i.e. a duplicate. Moreover, in a preferred embodiment, the present invention provides a combination of a source of first and second enzymatic active domain, wherein said first and second enzymatic active domains are comprised on distinct first and second polypeptides, and wherein said first enzymatic domain is histidine-dependent amidohydrolases/peptidase domain and said second enzymatic active domain is an endopeptidase domain or said first enzymatic active domain is a cysteine, histidine-dependent amidohydrolases/peptidase domain and said second enzymatic active domain is amidase domain or said first enzymatic active domain is an endopeptidase domain and said second enzymatic active domain is amidase domain, and wherein said first and second polypeptide each further comprise a cell wall binding domain.

In a preferred embodiment, the present invention provides a combination of a source of first enzymatic active domain and a second enzymatic active domain, wherein said first and second enzymatic active domains are comprised on distinct first and second polypeptides, and wherein said first enzymatic active domain is a cysteine, histidine-dependent amidohydrolases/peptidase domain and said second enzymatic active domain is an endopeptidase domain, and wherein said combination further comprises a source of a third enzymatic active domain comprised on a distinct third polypeptide, wherein said third enzymatic active domain is an amidase domain and said distinct first, second and third polypeptide each further comprises a cell wall-binding domain, and wherein each of said distinct first, second and third polypeptides comprises a multiplicity of said first, second or third enzymatic active domain, preferably said multiplicity being 2, i.e. a duplicate. Moreover, in a preferred embodiment, the present invention provides a combination of a source of first, second and third enzymatic active domain, wherein said first, second and third enzymatic active domains are comprised on distinct first, second and third polypeptides, and wherein said first enzymatic domain is histidine-dependent amidohydrolases/peptidase domain, said second enzymatic active domain is an endopeptidase domain and said third enzymatic active domain is an amidase domain, and wherein said first, second and third polypeptide each further comprise a cell wall binding domain.

Preferred is a combination according to the present invention, wherein, a first enzymatic active domain according to the present invention has at least 80, 81, 82, 83, 84, 85, 86, 87, 88, 89, 90, 91, 92, 93, 94, 95, 96, 97, 98, 99 or 100% identity with SEQ ID NO: 10 and a second enzymatic active domain according to the present invention as at least 80, 81, 82, 83, 84, 85, 86, 87, 88, 89, 90, 91, 92, 93, 94, 95, 96, 97, 98, 99 or 100% identity with SEQ ID NO: 16.

Preferred is a combination according to the present invention, wherein, a first enzymatic active domain according to the present invention has at least 80, 81, 82, 83, 84, 85, 86, 87, 88, 89, 90, 91, 92, 93, 94, 95, 96, 97, 98, 99 or 100% identity with SEQ ID NO: 10 and a second enzymatic active domain according to the present invention as at least 80, 81, 82, 83, 84, 85, 86, 87, 88, 89, 90, 91, 92, 93, 94, 95, 96, 97, 98, 99 or 100% identity with SEQ ID NO: 18.

Preferred is a combination according to the present invention, wherein, a first enzymatic active domain according to the present invention has at least 80, 81, 82, 83, 84, 85, 86, 87, 88, 89, 90, 91, 92, 93, 94, 95, 96, 97, 98, 99 or 100% identity with SEQ ID NO: 16 and a second enzymatic active domain according to the present invention as at least 80, 81, 82, 83, 84, 85, 86, 87, 88, 89, 90, 91, 92, 93, 94, 95, 96, 97, 98, 99 or 100% identity with SEQ ID NO: 18.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 28.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 46 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 28.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 70.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 52.

More preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 70 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 52.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 28.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 70 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 34.

More preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 70 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 28.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 34.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52 and a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46.

Preferred is a combination according to the present invention, wherein a first enzymatic active domain according to the present invention has at least 80, 81, 82, 83, 84, 85, 86, 87, 88, 89, 90, 91, 92, 93, 94, 95, 96, 97, 98, 99 or 100% identity with SEQ ID NO: 10, a second enzymatic active domain according to the present invention as at least 80, 81, 82, 83, 84, 85, 86, 87, 88, 89, 90, 91, 92, 93, 94, 95, 96, 97, 98, 99 or 100% identity with SEQ ID NO: 16 and a third enzymatic active domain according to the present invention has at least 80, 81, 82, 83, 84, 85, 86, 87, 88, 89, 90, 91, 92, 93, 94, 95, 96, 97, 98, 99 or 100% identity with SEQ ID NO: 18.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 28.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 32, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 44 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 26.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 26.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 36, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 48 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 30.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 32, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 26.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 44 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 26.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 32, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 44 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 28.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 32, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 28.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 44 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 28.

Preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 50.

Further preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 56, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 68 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 50.

Also preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 60, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 72 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 54.

Also preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 56, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 50.

Also preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 68 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 50.

Also preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 56, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 68 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 65, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 68 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination according to the present invention, wherein a first polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the present invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the present invention has at least 80, 81, 82, 83, 84, 85, 86, 87, 88, 89, 90, 91, 92, 93, 94, 95, 96, 97, 98, 99 or 100% identity with SEQ ID NO: 28. It is to be understood that a combination according to the present invention encompasses mixtures of a source of a first, a source of a second and optionally a source of a third and/or further enzymatic active domain according to in varying ratios. Preferably, a combination according to the present invention comprises a source a first and a source a second enzymatic active domain according to the present invention, wherein said first and second enzymatic active domain are present in equimolar amounts. Also preferred is a combination according to the present invention comprising a source a first, a source a second and a source a third enzymatic active domain according to the present invention, wherein said first, second and third enzymatic active domain are present in equimolar amounts. Also preferred is a combination according to the present invention comprising a source a first, a source a second, a source a third and a source a further enzymatic active domain according to the present invention, wherein said first, second, third and further enzymatic active domain are present in equimolar amounts.

In a second aspect, the present invention provides a combination according to the first aspect, wherein a source of a first, second and optionally third and/or further enzymatic active domain according to the first aspect of the invention comprises a polypeptide. Said polypeptide may be a protein, a digest of a protein and/or a fragment of a protein or digest, which may be in a purified form or may be comprised within a crude composition, preferably of biological origin, such as a bacterial lysate, yeast lysate, fungal lysate, sonicate or fixate. Alternatively, said polypeptide may be a chemically synthesized polypeptide or a recombinant polypeptide produced in vitro.

Preferably, a source of said first enzymatic active domain according to the present invention comprises a first polypeptide according to the first aspect of the invention, a second enzymatic active domain according to the present invention comprises a second polypeptide according to the first aspect of the invention and optionally a third enzymatic active domain according to the present invention comprises a third polypeptide according to the first aspect of the invention and optionally a further enzymatic active domain according to the present invention comprises a further polypeptide according to the first aspect of the invention. More preferably, said source of said first enzymatic active domain consists of a first polypeptide according to the first aspect of the invention, said second enzymatic active domain consists of a second polypeptide according to the first aspect of the invention, said third enzymatic active domain consists of a third polypeptide according to the first aspect of the invention, and said further enzymatic active domain consists of a third polypeptide according to the further aspect of the invention.

An embodiment encompasses a combination according to the present invention, wherein a first, second and/or optionally third and/or further polypeptide of the present invention is a variant first, second and/or third and/or further polypeptide. A variant polypeptide may be a non-naturally occurring form of the polypeptide. A polypeptide variant may differ in some engineered way from the polypeptide isolated from its native source. A variant may be made by site-directed mutagenesis starting from the nucleotide sequence encoding a polypeptide as defined herein and indicated by SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71 or 73. Preferably, a polypeptide variant according to the present invention has at least 80, 81, 82, 83, 84, 85, 86, 87, 88, 89, 90, 91, 92, 93, 94, 95, 96, 97, 98, 99 or 100% identity to any of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72 or 74. Preferably, in a combination according to the present invention a polypeptide variant contains mutations that do not alter the biological function of the encoded polypeptide.

A polynucleotide according to the present invention can have at least 80, 81, 82, 83, 84, 85, 86, 87, 88, 89, 90, 91, 92, 93, 94, 95, 96, 97, 98, 99 or 100% identity to any of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71 or 73, or alternatively hybridise under stringent conditions with these given sequences. Stringent hybridisation conditions are those as understood in the art, e.g. hybridisation in 6×SSC (20×SSC per 1000 ml: 175.3 g NaCl, 107.1 g sodium citrate.5H 20, pH 7.0), 0.1% SDS, 0.05% sodium pyrophosphate, 5*Denhardt's solution and 20 µg/ml denatured herring sperm DNA at 56° C. for 18-24 hrs followed by two 30 min. washes in 5×SSC, 0.1% SDS at 56° C. and two 30 min. washes in 2×SSC, 0.1% SSC at 56° C.

According to a preferred embodiment, a polypeptide variant exhibits lytic or cell wall-binding activity which is the same or enhanced as compared to the lytic and/or cell wall-binding activity of SEQ ID NO: 2, as measured in an assay as earlier identified herein.

It is to be understood that a combination according to the present invention encompasses mixtures of a first, second and optionally third and/or further polypeptide according to the present invention in varying ratios. Preferably, a combination according to the present invention comprises a first, second and optionally third and/or further polypeptide according to the present invention, wherein a first and second enzymatic active domain are present in equimolar amounts. Also preferred is a combination according to the present invention comprising equimolar amounts of a first, second and optionally third and/or further polypeptide according to the present invention, wherein a first, second and third and/or further enzymatic active domain are present in equimolar amounts.

In a third aspect, the present invention provides a combination according to the first aspect of the present invention, wherein a source of a first enzymatic active domain according to the first aspect of the present invention comprises a polynucleotide encoding said first enzymatic active domain, a source of a second enzymatic active domain according to the first aspect of the present invention comprises a polynucleotide encoding said second enzymatic active domain, and optionally a source of a third enzymatic active domain according to the first aspect of the present invention comprises a polynucleotide encoding said third enzymatic active domain and optionally a source of a further enzymatic active domain according to the first aspect of the present invention comprises a polynucleotide encoding said further enzymatic active domain. Said polynucleotide may be an RNA or DNA molecule.

Preferably, the present invention provides a combination according to the present invention, wherein a first polynucleotide encodes a first enzymatic active domain according to the present invention and a second polynucleotide encodes a second enzymatic active domain according to the present invention. Preferably, in a combination according to the present invention a first and/or second polynucleotide according to the present invention further encode a cell wall-binding domain as defined herein. Preferably, the present invention provides a combination according to the present invention, wherein a first polynucleotide encodes a first enzymatic active domain according to the present invention, a second polynucleotide encodes a second enzymatic active domain according to the present invention, a third polynucleotide encodes a third enzymatic active domain according to the present invention and a further polynucleotide encodes a further enzymatic active domain according to the present invention. Preferably, in a combination according to the present invention a first, second, third and/or further polynucleotide according to the present invention further encode a cell wall-binding domain as defined herein.

The present invention further provides a combination according to the present invention, wherein a first, second and/or optionally third and/or further polypeptide of the present invention is a chimeric first, second, third and/or further polypeptide encoded by naturally occurring or retrofitted polynucleotide constructs. A retrofitted construct is defined herein as a polynucleotide comprising heterologous nucleotide sequences. As used herein the term heterologous sequence or heterologous polynucleotide is one that is not naturally found operably linked as neighboring sequence of said first nucleotide sequence. As used herein, the term heterologous may mean recombinant. Recombinant refers to a genetic entity distinct from that generally found in nature. As applied to a nucleotide sequence or nucleic acid molecule, this means that said nucleotide sequence or nucleic acid molecule is the product of various combinations of cloning, restriction and/or ligation steps, and other procedures that result in the production of a construct that is distinct from a sequence or molecule found in nature. Preferably, in a combination according to the present invention said chimeric polypeptide comprises at least a first, second or third polypeptide as defined earlier herein and further comprises at least one cell binding-domain as defined earlier herein.

An alternative embodiment provides for a combination of the present invention, wherein a chimeric polypeptide comprises an endolysin as defined herein, covalently linked to a hydrophobic pentapeptide on its C-terminus, preferably said hydrophobic pentapeptide is Phe-Phe-Val-Ala-Pro, resulting in increased bactericidal action of the endolysin especially towards gram negative bacteria as reported by Ibrahim et al., 1994 (JBC 1994 Vol. 269, p. 5053-5063).

Preferably, in a combination according to the present invention a first, second, third and/or further polynucleotide according to the present invention has a length of at least 420, 450, 480, 510, 540, 570, 600, 630, 660, 690, 720, 750, 780, 810, 840, 870, 900, 930, 960 or 990 nucleotides and/or a length of at most 2550, 2400, 2250, 2100, 1950, 1800, 1650, 1500, 1470, 1440, 1410, 1380, 1350, 1320, 1290, 1260, 1230, 1200, 1070, 1040, or 1100 nucleotides. More preferably, a first, second, third and/or further polynucleotide according to the present invention has a length of 420-2550, 420-2400, 420-2250, 420-2100, 420-1950, 420-1800, 420-1650, 420-1500, 420-1470, 420-1440, 420-1410, 420-1380, 420-1350, 420-1320, 420-1290, 420-1260, 420-1230, 420-1200, 420-1070, 420-1040, or 420-1100, 450-2550, 480-2550, 510-2550, 540-2550, 570-2550, 600-2550, 630-2550, 660-2550, 690-2550, 720-2550, 750-2550, 780-2550, 810-2550, 840-2550, 870-2550, 900-2550, 930-2550, 960-2550 or 990-2550 nucleotides Preferably, a first and second polynucleotide according to the present invention each have a length of at least 420, 450, 480, 510, 540, 570, 600, 630, 660, 690, 720, 750, 780, 810, 840, 870, 900, 930, 960 or 990 nucleotides and/or a length of at most 2550, 2400, 2250, 2100, 1950, 1800, 1650, 1500, 1470, 1440, 1410, 1380, 1350, 1320, 1290, 1260, 1230, 1200, 1070, 1040, or 1100 nucleotides. More preferably, a first and second polynucleotide according to the present invention each have a length of 420-2550, 420-2400, 420-2250, 420-2100, 420-1950, 420-1800, 420-1650, 420-1500, 420-1470, 420-1440, 420-1410, 420-1380, 420-1350, 420-1320, 420-1290, 420-1260, 420-1230, 420-1200, 420-1070, 420-1040, or 420-1100, 450-2550, 480-2550, 510-2550, 540-2550, 570-2550, 600-2550, 630-2550, 660-2550, 690-2550, 720-2550, 750-2550, 780-2550, 810-2550, 840-2550, 870-2550, 900-2550, 930-2550, 960-2550 or 990-2550 nucleotides.

Preferably, a first, second and third polynucleotide according to the present invention each have a length of at least 420, 450, 480, 510, 540, 570, 600, 630, 660, 690, 720, 750, 780, 810, 840, 870, 900, 930, 960 or 990 nucleotides and/or a length of at most 2550, 2400, 2250, 2100, 1950, 1800, 1650, 1500, 1470, 1440, 1410, 1380, 1350, 1320, 1290, 1260, 1230, 1200, 1070, 1040, or 1100 nucleotides. More preferably, a first, second and third polynucleotide according to the present invention each have a length of 420-2550, 420-2400, 420-2250, 420-2100, 420-1950, 420-1800, 420-1650, 420-1500, 420-1470, 420-1440, 420-1410, 420-1380, 420-1350, 420-1320, 420-1290, 420-1260, 420-1230, 420-1200, 420-1070, 420-1040, or 420-1100, 450-2550, 480-2550, 510-2550, 540-2550, 570-2550, 600-2550, 630-2550, 660-2550, 690-2550, 720-2550, 750-2550, 780-2550, 810-2550, 840-2550, 870-2550, 900-2550, 930-2550, 960-2550 or 990-2550 nucleotides.

Preferably, a first, second, third and further polynucleotide according to the present invention each have a length of at least 420, 450, 480, 510, 540, 570, 600, 630, 660, 690, 720, 750, 780, 810, 840, 870, 900, 930, 960 or 990 nucleotides and/or a length of at most 2550, 2400, 2250, 2100, 1950, 1800, 1650, 1500, 1470, 1440, 1410, 1380, 1350, 1320, 1290, 1260, 1230, 1200, 1070, 1040, or 1100 nucleotides. More preferably, a first, second, third and further polynucleotide according to the present invention each have a length of 420-2550, 420-2400, 420-2250, 420-2100, 420-1950, 420-1800, 420-1650, 420-1500, 420-1470, 420-1440, 420-1410, 420-1380, 420-1350, 420-1320, 420-1290, 420-1260, 420-1230, 420-1200, 420-1070, 420-1040, or 420-1100, 450-2550, 480-2550, 510-2550, 540-2550, 570-2550, 600-2550, 630-2550, 660-2550, 690-2550, 720-2550, 750-2550, 780-2550, 810-2550, 840-2550, 870-2550, 900-2550, 930-2550, 960-2550 or 990-2550 nucleotides.

In a fourth aspect, the present invention provides for a polypeptide and/or a polynucleotide as defined herein above. Preferably, said polypeptide is any of the first, second, third and/or further polypeptide as defined in the second aspect of the invention. Preferably, said polynucleotide is encoding any of said first, second, third and/or further polypeptide. Preferably said polynucleotide is any of the first, second, third and/or further polynucleotide as defined in the third aspect of the invention. Preferably, said polypeptide comprises and/or consists of an enzymatic active domain, a cell wall binding domain and optionally a tag for ease of purification as defined herein, preferably said enzymatic active domain being a cysteine, histidine-dependent amidohydrolases/peptidase domain, an endopeptidase domain or an amidase domain, and preferably said polypeptide comprises a multiplicity of said enzymatic active domain, preferably said multiplicity being 2, i.e. a duplicate. Preferably, said polypeptide has at least 80, 81, 82, 83, 84, 85, 86, 87, 88, 89, 90, 91, 92, 93, 94, 95, 96, 97, 98, 99 or 100% identity to any of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70 or 72. Preferably, said polynucleotide has at least 80, 81, 82, 83, 84, 85, 86, 87, 88, 89, 90, 91, 92, 93, 94, 95, 96, 97, 98, 99 or 100% identity to any of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69 or 71, or alternatively is able to hybridise under stringent conditions with these given sequences. More preferably, said polypeptide comprises and/or consists of a duplicated amidase domain and a cell wall binding domain and optionally a tag for ease of purification as defined herein, preferably said amidase domain is of S. aureus bacteriophage Φ2638a endolysin and said cell wall binding domain is of S. Simulans lysostaphin. Most preferably, said polypeptide comprises and/or consists of a duplicated endopeptidase domain and a cell wall binding domain and optionally a tag for ease of purification as defined herein, preferably said endopeptidase domain is a Peptidase M23 domain of S. Simulans lysostaphin and said cell wall binding domain is of S. Simulans lysostaphin.

Preferably, said polypeptide has at least 80, 81, 82, 83, 84, 85, 86, 87, 88, 89, 90, 91, 92, 93, 94, 95, 96, 97, 98, 99 or 100% identity with SEQ ID NO: 28, 34, 46, 52, 58 or 70, more preferably, said polypeptide has at least 80, 81, 82, 83, 84, 85, 86, 87, 88, 89, 90, 91, 92, 93, 94, 95, 96, 97, 98, 99 or 100% identity with SEQ ID NO: 28, 46, 52, or 70, even more preferably, said polypeptide has at least 80, 81, 82, 83, 84, 85, 86, 87, 88, 89, 90, 91, 92, 93, 94, 95, 96, 97, 98, 99 or 100% identity with SEQ ID NO: 46, or 70, most preferably said polypeptide has at least 80, 81, 82, 83, 84, 85, 86, 87, 88, 89, 90, 91, 92, 93, 94, 95, 96, 97, 98, 99 or 100% identity with SEQ ID NO: 70. Preferably said polynucleotide is encoding for any of the indicated preferred polypeptides.

Preferably, said polynucleotide has at least 80, 81, 82, 83, 84, 85, 86, 87, 88, 89, 90, 91, 92, 93, 94, 95, 96, 97, 98, 99 or 100% identity with SEQ ID NO: 27, 33, 45, 51, 57 or 69, or alternatively is able to hybridise under stringent conditions with these given sequences. Preferably, said polypeptide has at least 80, 81, 82, 83, 84, 85, 86, 87, 88, 89, 90, 91, 92, 93, 94, 95, 96, 97, 98, 99 or 100% identity with SEQ ID NO: 27, 45, 51, or 69, or alternatively is able to hybridise under stringent conditions with these given sequences. Even more preferably, said polypeptide has at least 80, 81, 82, 83, 84, 85, 86, 87, 88, 89, 90, 91, 92, 93, 94, 95, 96, 97, 98, 99 or 100% identity with SEQ ID NO: 45, or 69, or alternatively is able to hybridise under stringent conditions with these given sequences. Most preferably said polypeptide has at least 80, 81, 82, 83, 84, 85, 86, 87, 88, 89, 90, 91, 92, 93, 94, 95, 96, 97, 98, 99 or 100% identity with SEQ ID NO: 69, or alternatively is able to hybridise under stringent conditions with these given sequences.

In another embodiment, said polypeptide is not SEQ ID NO: 70 and/or said polynucleotide is not SEQ ID NO: 69.

In a fifth aspect the present invention relates to a combination according to the third aspect of the present invention and/or a polynucleotide of the fourth aspect, wherein a polynucleotide according to the third aspect and/or fourth aspect of the present invention is present in an expression construct. Moreover, said first, second and/or third and/or further polynucleotide can be present in an expression construct. Said expression construct may be 'naked' DNA or RNA preferably comprised in vesicles or liposomes, or may be comprised in an expression vector. Preferably said expression construct is an expression vector, more preferably a plasmid, a cosmid, a bacteriophage or a virus is transformed by introducing a polynucleotide encoding a first, second or third polypeptide as defined earlier herein and wherein said polynucleotide is operably linked to one or more control which direct the production or expression of the encoded polypeptide in a cell, a subject, or a cell-free system. Such transformation vectors according to the host organism to be transformed are well known to those skilled in the art and widely described in the literature. The expression construct may also be any DNA or RNA virus, such as, but not limited to, Adenovirus, Adeno-Associated Virus, Retrovirus, Lentivirus, Modified Vaccinia Nakara virus or Fowl Pox Virus or any other viral vector applicable of conferring expression of polypeptides into a chosen subject. DNA vectors may be non-integrating, such as episomally replicating vectors, or may be vectors integrating in the host genome by random integration or by homologous recombination. An expression vector may be seen as a recombinant expression vector.

Within the present invention, a first, second, third and/or fourth polynucleotide according to the present invention can be present on distinct expression constructs, or may be present combined on a single expression construct. Moreover, in a combination of the present invention said first polynucleotide can be present on a first expression construct while the second polynucleotide is present on a second expression construct. Furthermore, in a combination of the present invention, said first polynucleotide can be present on a first expression construct, the second on a second expression construct, the third present on a third expression construct, and the further present on a further expression construct. It is also encompassed within the present invention that the first, second, third and/or further are comprised on a single expression construct. Combinations are also possible, where two polypeptides of the present invention are present on a single expression construct, while one of them is present on a distinct expression construct.

In a sixth aspect, provided is a combination according to the third aspect of the invention and/or a polynucleotide of the fourth aspect—wherein an expression construct according to the fifth aspect of the invention is present in an expression system. Within the present invention, said expression system may be a cell, preferably a microbial, prokaryotic or eukaryotic cell, which is suitable for expression of the polypeptide of the invention. In a preferred embodiment, said cell is an *E. coli*. In an even more preferred embodiment, said cell is *E. coli* XL1blue MRF.

In a seventh aspect, provided is a process for the transformation of a host organism or a cell, by introducing at least one polynucleotide according to the present invention, which transformation may be carried out by any suitable known means which have been widely described in the specialist literature and in particular in the references cited in the present application, more particularly by the vector according to the present invention. Within the present invention, said first, second, third and/or further polypeptide as defined herein can be present in a single transformed host organism or cell or present in distinct transformed host organisms or cells. A cell may be any microbial, prokaryotic or eukaryotic cell, which is suitable for expression of the polypeptide of the present invention. In a preferred embodiment, said cell is an *E. coli*. In an even more preferred embodiment, said cell is *E. coli* XL1blue MRF'. A preferred method for producing, optionally purifying and optionally freeze-drying a first, second, third and/or further polypeptide as defined herein, comprises the steps of:

i) producing said first, second, third and/or further polypeptide in a cell comprising a expression construct as defined herein, optionally ii) purifying said first, second, third and/or further polypeptide, and optionally iii) freeze-drying said purified first, second, third and/or further polypeptide.

In a preferred embodiment, an *E. coli* is used in step i) for producing said first, second, third and/or further polypeptide using recombinant technologies. More preferably an *E. coli* XL1blueMRF is used in step i) for producing said first, second, third and/or further polypeptide using recombinant technologies. Preferably, in step ii), IMAC and Econo-Pac Chromatography columns (Biorad) packed with 5 mL low density Nickel chelating agarose beads (ABT beads) in combination with gravity flow is used to purify said first, second, third and/or further polypeptide. The eluted first, second, third and/or further polypeptide can be dialyzed for 2, 4, and 12 hours against 3×11 lyophilization buffer, said buffer preferably comprising 50 mM phosphate, 500 mM sucrose, 200 mM mannitol, 0.005% polysorbate20, pH 7.4.

Even more preferred, said method for producing, optionally purifying and freeze-drying a first, second, third and/or further polypeptide as defined herein, further comprises a method of treating said first, second, third and/or further polypeptide obtainable by the method described above. Said treatment comprises substituting a divalent metal ion for increasing a lytic activity as compared to an untreated first, second, third and/or further polypeptide, preferably said method comprising the steps of:

iv) dialyzing said polypeptide against a buffer comprising a chelating compound;

v) dialyzing said polypeptide against a divalent metal ion-containing buffer, preferably said divalent metal ion being selected from the group consisting of $Mn^{2+}$, $Co^{2+}$, $Cu^{2+}$, and $Zn^{2+}$.

A "chelating compound" being defined herein as a compound that binds a metal ion. Well known chelating compounds are ethylene diamine tetraacetic acid (EDTA) and ethylene glycol tetraacetic acid (EGTA). Preferably EDTA is used in step v) of the method described herein. Preferably, the divalent metal ion of step v) of said method is selected from the group consisting $Mn^{2+}$, $Co^{2+}$, $Cu^{2+}$, more preferably, said divalent metal ion is selected from the group consisting of $Mn^{2+}$ and $Co^{2+}$, even more preferably said divalent metal ion is $Mn^{2+}$.

In an eighth aspect of the present invention, a combination according to the first aspect of the present invention is present in at least two distinct compositions. Moreover, the invention provides a combination of the present invention, wherein a first composition comprises a source of first enzymatic active domain according to the present invention and a second composition comprises a source of second enzymatic active domain according to the present invention, wherein said first and second enzymatic active domains are comprised on distinct first and second polypeptides according to the first aspect, preferably wherein said first composition is free of a source of said second enzymatic domain and said second composition is free of a source of said first enzymatic active domain. In addition, the present invention provides a combination according to the present invention, wherein a first composition comprises a source of first enzymatic active domain according to the present invention, a second composition comprising a source of second enzymatic active domain according to the present invention, a third composition comprising a source of a third enzymatic active domain according to the present invention, and further composition comprising a source of a further enzymatic active domain according to the present invention, wherein said first, second, third and further enzymatic active domains are comprised on distinct first, second, third and further polypeptides according to the first aspect of the present invention, preferably wherein said first composition is free of said source of said second, third and further enzymatic domain, said second composition is free of said source of said first, third and further enzymatic active domain, said third composition is free of said source of said first, second and further enzymatic active domain and said further composition is free of said source of said first, second and third enzymatic active domain.

Moreover, the present invention provides a combination according to the present invention, wherein a first composition comprises a source of a first polypeptide according to the present invention, a second composition comprises a source of a second polypeptide according to the present invention, and optionally third and/or further composition comprises a source of a third and/or further respective polypeptide according to the present invention. Preferably said first composition is free of said source of a second polypeptide, free of said source of a third polypeptide and said free of source of a further respective polypeptide. Preferably, said second composition is free of said source of a first polypeptide, free of said source of a third polypeptide and free of said source of a further respective polypeptide. Preferably said third composition is free of said source of a first polypeptide, free of said source of a second polypeptide and free of said source of a further respective polypeptide. Preferably said further composition is free of said source of a first polypeptide, free of said source of a second polypeptide and free of said source of a third polypeptide.

In a ninth aspect, the present invention provides a composition comprising any of the first, second, third and/or further polypeptide and/or nucleotide of the fourth aspect of the invention. Preferably, the present invention provides for a composition comprising any of the first, second, third and/or further polypeptide as defined the second aspect of the invention and/or nucleotide as defined in the third aspect of the invention.

In a tenth aspect, the present invention provides a composition comprising a combination according to the first aspect of the present invention. Moreover, the invention provides a single composition comprising a source of a first enzymatic active domain according to the present invention and source of a second enzymatic active domain according to the present invention, wherein said first and second enzymatic active domains are comprised on distinct first and second polypeptides. Moreover, the present invention provides a composition according to the present invention comprising source of a first enzymatic active domain according to the present invention and a source of a second enzymatic active domain according to the present invention, wherein said first enzymatic active domain is comprised on a first polypeptide according to the first aspect of the present invention and said second enzymatic active domain is comprised on a second polypeptide according to the first aspect of the present invention, wherein said first polypeptide is free of said second enzymatic active domain and said second polypeptide is free of said first enzymatic active domain.

In addition, the invention provides a single composition comprising a source of a first enzymatic active domain according to the present invention, a source of a second enzymatic active domain according to the present invention, and a source of a third and/or further enzymatic active domain according to the present invention, wherein said first, second and third and/or further enzymatic active domains are comprised on distinct first, second and third and/or further polypeptides according to the first aspect of the present invention. Moreover, the present invention provides a composition comprising a source of a first enzymatic active domain according to the present invention, a source of a second enzymatic active domain according to the present invention, and a source of a third and/or further enzymatic active domain according to the present invention wherein said first enzymatic active domain is comprised on a first polypeptide according to the first aspect of the present invention, said second enzymatic active domain is comprised on a second polypeptide according to the first aspect of the present invention, and said third and/or further enzymatic active domain is comprised on a third and/or further polypeptide according to the first aspect of the present invention, wherein said first polypeptide is free of said second enzymatic active domain and third and/or further enzymatic active domain, said second polypeptide is free of said first and third and/or further enzymatic active domain and said third and/or further polypeptide is free of said first and second enzymatic active domain.

The first, second and optionally third and/or further composition according to the eighth aspect of the present invention and/or a single composition according to the ninth and/or tenth aspect of the present invention may be in the liquid, solid or semi-liquid or semi-solid form. Preferably, a first, second and optionally third and/or further composition according to the eight aspect of the present invention and/or the single composition according to the ninth and/or tenth aspect of the present invention is an antimicrobial, preferably a food preservative or a disinfectant. Preferably said antimicrobial is for killing a bacterium, preferably a bacterium of the genus *Staphylococcus*, more preferably a bacterium of the species *Staphylococcus aureus*. Preferably, a first, second and optionally third and/or further composition according to the eight aspect of the present invention and/or a single composition according to the ninth and/or tenth aspect of the invention further comprises an pharmaceutical acceptable carrier and/or an additional active ingredient selected from the group consisting of a bacteriophage, a bacteriostatic agent, a bactericide agent, an antibiotic, a surfactant and/or an enzyme. An antibiotic of the present invention can be any antibiotic known in the art including antibiotics and chemotherapeutic agents, and including but not limited to vancomycin, nisin, danofloxacin and neomycin. An enzyme useful in a composition of the present invention includes but is not limited to enzymes that aid in breaking up biofims (e.g. biofilms found in food processing equipment) such as but not limited to polysaccharide depolymerise enzymes and protease. A surfactant useful in a composition of the present invention helps to wet the surface so that the active ingredient of the present invention, including the combination of the present invention, is properly distributed over the various surfaces, and to solubilise and remove dirt so that the *Staphylococcus* are accessible to the active ingredients of the invention. Suitable surfactants include but are not limited to polysorbate (tween) 80, 20 and 81 and Dobanols (Shell Chemical Co. RTM).

An antimicrobial disinfectant composition of the present invention may further comprise surface disinfectants known in the art such as but not limited to benzoic acid and PBT, preferably disinfectants with which a combination of the first aspect of the present invention, preferably an expression system, even more preferably a (recombinant) bacteriophage of the present invention, is compatible.

The first, second and optionally third and/or further composition of the eight aspect of the present invention and/or the single composition of the ninth and/or tenth aspect of the present invention may further comprise a pharmaceutically acceptable carrier. Such composition is preferably for use as a medicine or as a medicament.

In a eleventh aspect, the present invention provides a combination of a first, second and optionally third and/or further composition according to the eight aspect of the present invention and/or a single composition according to the ninth and/or tenth aspect of the present invention for use as a medicament. Preferably said medicament is for the prevention or delay of a *Staphylococcus* related condition in a subject such as an infectious disease. More preferably, the invention relates to a pharmaceutical or medical composition for the treatment of a condition related to *Staphylococcus*. Preferably, the invention relates to a pharmaceutical or medical composition for the treatment of an infectious disease caused by a bacterium, preferably a bacterium of the genus *Staphylococcus*, more preferably a bacterium of the species *S. aureus*. Preferably, said infectious disease is a skin infection, mastitis, pneumonia, meningitis, endocarditis, Toxic Shock Syndrome (TSS), sepsis, septicemia, bacteremia, or osteomyelitis. Preferably, said skin infection is selected from the group of pimples, impetigo, boils, furuncles, cellulitis folliculitis, carbuncles, scaled skin syndrome and abscesses.

The combination of said first, second and optionally third and/or further composition according to the eight aspect of the present invention and/or the single composition according to the ninth and/or tenth aspect of the present invention is preferably said to be active, functional or therapeutically active or able to treat, prevent and/or delay an infectious disease when it decreases the amount of a *Staphylococcus* genera present in a patient or in a cell of said patient or in a cell line or in a cell free in vitro system and preferably means that 99%, 90%, 80%, 70%, 60%, 50%, 40%, 30%, 20%, 10%, 5% or less of the initial amount of a *Staphylococcus* genera, is still detectable. More preferably, no *Staphylococcus* genera is detectable. In this paragraph, the expression "amount of *Staphylococcus* genera" preferably means viable Staphylococci. Staphylococci of all genera may be detected using standard techniques known by the artisan such as immunohistochemical techniques using *Staphylococcus* specific antibodies, tube coagulase tests that detect staphylocoagulase or "free coagulase", detection of surface proteins such as clumping factor (slide coagulase test) and/or protein A (commercial latex tests). Viable Staphylococci may be detected using standard techniques known by the artisan such as microbiological bacterial culture techniques and/or real-time quantitative reverse transcription polymerase chain reaction to assay for bacterial mRNA.

A decrease according to the present invention is preferably assessed in a tissue or in a cell of an individual or a patient by comparison to the amount present in said individual or patient before treatment with said composition or polypeptide of the invention. Alternatively, the comparison can be made with a tissue or cell of said individual or patient which has not yet been treated with said composition or polypeptide in case the treatment is local.

Encompassed within the present invention is a method for treatment, prevention or delay of a microbial related condition in an individual, comprising administering to said individual a combination of a first, second and optionally third and/or further composition according to the eighth aspect of the present invention. Moreover, the present invention provides the use of a combination according to the eight aspect of the present invention, wherein said first, second and optionally third and/or further enzymatic active domains are comprised on distinct first, second and optionally third and/or further polypeptides, wherein said first, second and optionally third and/or further polypeptides are comprised in separate compositions, for the manufacture of a medicament, preferably a medicament for the treatment, prevention or delay of a microbial related condition.

The combination of the first, second and optionally third and/or further composition according to the eighth aspect of the present invention and/or the single composition according to the ninth and/or tenth aspect of the present invention can be used to treat animals, including humans, infected with *S. aureus*. Any suitable route of administration can be used to administer said combination of compositions or said single composition including but not limited to: oral, aerosol or other device for delivery to the lungs, nasal spray, intravenous, intramuscular, intraperitoneal, intrathecal, vaginal, rectal, topical, lumbar puncture, intrathecal, and direct application to the brain and/or meninges. A combination of composition or a single composition of the invention may be administered to a patient or of a cell, tissue or organ or said patient at least one week, one month, six month, one year or more. In an embodiment, said combination of compositions according to the seventh aspect of the present invention is administered separately. In an alternative embodiment, said combination is stored separately, and admixed just before administration. Preferably, said combination is admixed to comprise equimolar amounts of said first, second and optionally third and/or further polypeptide. Even more preferably, said combination is admixed to comprise equimolar amounts of said first, second and optionally third and/or further enzymatic active domain.

In a twelfth aspect, the present invention provides a use of a combination of compositions according to the eighth aspect or a single composition according to the ninth and/or tenth aspect of the present invention as an antimicrobial agent, preferably a food preservative or a disinfectant. An antimicrobial agent is for controlling a bacterium, preferably said bacterium is a *Staphylococcus*, more preferably said bacterium is *Staphylococcus aureus*. Preferably, an antimicrobial agent is for killing a bacterium, preferably said bacterium is a *Staphylococcus*, more preferably said bacterium is *Staphylococcus aureus*. A disinfectant is an antimicrobial agent specific for use on inanimate objects.

In a thirteenth aspect, the present invention provides a method for controlling microbial contamination in a food- or feed product, on and/or in food- or feed processing equipment or medical equipment on and/or in food- or feed containers comprising contacting a combination of compositions according to the eighth aspect of the present invention or a composition according the ninth and/or tenth aspect of the present invention with the food- or feed product, the food- or feed processing equipment or medical equipment and/or the food- or feed containers.

Preferably a method according to the present invention is for controlling bacterium of the genus *Staphylococcus*, more preferably a bacterium of the species *Staphylococcus aureus*. Preferably, said method of controlling includes the reduction of counts of *Staphylococcus* bacteria and/or the prevention of their growth in the first place, in food products (including but not limited to the dairy industry) as well as in food processing plants in which the food products are being processed such as on processing equipment and other sites in food industry facilities, e.g. food storage container. Furthermore, said method of controlling includes the reduction of counts of *Staphylococcus* bacteria and/or the prevention of their growth in the first place, in medical equipment. Preferably, said method is of controlling for cleaning and sterilizing medical equipment, such as fiberscopes, like gastrocameras, peritoneoscopes, thoracoscopes and arthoroscopes, and medical supplies, like catheters and tubes that have long ducts or hollow portions and tend to be repetitively employed by being introduced into human bodies.

A method of the present invention encompasses the application of a combination of compositions according to the eight aspect of the present invention and/or a composition according to the ninth and/or tenth aspect of the present invention on or into food products, and/or into various physical sites within the food processing plants on or in food processing equipment, by a number of means including, but not limited to, admixing, spraying or directly applying said combination of compositions of the eight aspect or composition of the ninth and/or tenth aspect of the present invention.

In a further embodiment, a combination of a source of said first aspect of the present invention can be isolated from said source, wherein said source is an expression system, such as a recombinant cell or a recombinant bacteriophage can be directly applied or administered without isolation of said polypeptide. For example, a cell which produces a first and second and optionally a third and/or further polypeptide of the present invention could be administered to a subject (human or animal) or applied to a surface where said first and second and optionally said third and/or further polypeptide of the present invention would be secreted into food, onto a surface or into the subject's gut. The combination of the present invention can then bind and optionally lyse bacterial cells, preferably a bacterium of the genus *Staphylococcus*, more preferably a bacterium of the species *Staphylococcus aureus*, present in this environment. The applications as defined herein significantly reduce the numbers of *Staphylococcus* bacteria that would otherwise be present.

Optionally, the method of the present invention can be combined with any sterilization method or disinfectant known in the art such as ultrasonic cleaning, irradiation or thermal sterilization, by immersing the equipment in a disinfectant solution such as ethanol, ammonium, iodine and/or aldehyde disinfectant, or by using gas sterilization by retaining the device in a closed atmosphere such as formaline gas or ethylene oxide gas.

DEFINITIONS

"Sequence identity" or "identity" in the context of amino acid- or nucleic acid-sequence is herein defined as a relationship between two or more amino acid (peptide, polypeptide, or protein) sequences or two or more nucleic acid (nucleotide, polynucleotide) sequences, as determined by comparing the sequences. In the art, "identity" also means the degree of sequence relatedness between amino acid or nucleotide sequences, as the case may be, as determined by the match between strings of such sequences. Within the present invention, sequence identity with a particular sequence preferably means sequence identity over the entire length of said particular polypeptide or polynucleotide sequence. The sequence information as provided herein should not be so narrowly construed as to require inclusion of erroneously identified bases. The skilled person is capable of identifying such erroneously identified bases and knows how to correct for such errors.

"Similarity" between two amino acid sequences is determined by comparing the amino acid sequence and its conserved amino acid substitutes of one peptide or polypeptide to the sequence of a second peptide or polypeptide. In a preferred embodiment, identity or similarity is calculated over the whole SEQ ID NO as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A polynucleotide is represented by a nucleotide sequence. A polypeptide is represented by an amino acid sequence. A nucleic acid construct is defined as a polynucleotide which is isolated from a naturally occurring gene or which has been modified to contain segments of polynucleotides which are combined or juxtaposed in a manner which would not otherwise exist in nature. Optionally, a polynucleotide present in a nucleic acid construct is operably linked to one or more control sequences, which direct the production or expression of said peptide or polypeptide in a cell or in a subject.

As used herein the term "heterologous sequence" or "heterologous nucleic acid" is one that is not naturally found operably linked as neighboring sequence of said first nucleotide sequence. As used herein, the term "heterologous" may mean "recombinant". "Recombinant" refers to a genetic entity distinct from that generally found in nature. As applied to a nucleotide sequence or nucleic acid molecule, this means that said nucleotide sequence or nucleic acid molecule is the product of various combinations of cloning, restriction and/or ligation steps, and other procedures that result in the production of a construct that is distinct from a sequence or molecule found in nature.

"Operably linked" is defined herein as a configuration in which a control sequence is appropriately placed at a position relative to the nucleotide sequence coding for the polypeptide of the invention such that the control sequence directs the production/expression of the peptide or polypeptide of the invention in a cell and/or in a subject.

"Operably linked" may also be used for defining a configuration in which a sequence is appropriately placed at a position relative to another sequence coding for a functional domain such that a chimeric polypeptide is encoded in a cell and/or in a subject.

Expression will be understood to include any step involved in the production of the peptide or polypeptide including, but not limited to, transcription, post-transcriptional modification, translation, post-translational modification and secretion.

Optionally, a promoter represented by a nucleotide sequence present in a nucleic acid construct is operably linked to another nucleotide sequence encoding a peptide or polypeptide as identified herein.

The term "transformation" refers to a permanent or transient genetic change induced in a cell following the incorporation of new DNA (i.e. DNA exogenous to the cell). When the cell is a bacterial cell, as is intended in the current invention, the term usually refers to an extrachromosomal, self-replicating vector which harbors a selectable antibiotic resistance.

An expression vector may be any vector which can be conveniently subjected to recombinant DNA procedures and can bring about the expression of a nucleotide sequence encoding a polypeptide of the invention in a cell and/or in a subject. As used herein, the term "promoter" refers to a nucleic acid fragment that functions to control the transcription of one or more genes or nucleic acids, located upstream with respect to the direction of transcription of the transcription initiation site of the gene. It is related to the binding site identified by the presence of a binding site for DNA-dependent RNA polymerase, transcription initiation sites, and any other DNA sequences, including, but not limited to, transcription factor binding sites, repressor and activator protein binding sites, and any other sequences of nucleotides known to one skilled in the art to act directly or indirectly to regulate the amount of transcription from the promoter. Within the context of the invention, a promoter preferably ends at nucleotide −1 of the transcription start site (TSS).

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

The term "control sequences" is defined herein to include all components, which are necessary or advantageous for the expression of a polypeptide. Each control sequence may be native or foreign to the nucleic acid sequence encoding the polypeptide. Such control sequences include, but are not limited to, a leader, optimal translation initiation sequences (as described in Kozak, 1991, J. Biol. Chem. 266:19867-19870), a polyadenylation sequence, a pro-peptide sequence, a pre-pro-peptide sequence, a promoter, a signal sequence, and a transcription terminator. At a minimum, the control sequences include a promoter, and transcriptional and translational stop signals.

The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence, which is recognized by a host cell for expression of the nucleic acid sequence. The promoter sequence contains transcriptional control sequences, which mediate the expression of the polypeptide. The promoter may be any nucleic acid sequence, which shows transcriptional activity in the cell including mutant, truncated, and hybrid promoters, and may be obtained from genes encoding extracellular or intracellular polypeptides either homologous or heterologous to the cell.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator, which is functional in the cell, may be used in the present invention.

The control sequence may also be a suitable leader sequence, a non-translated region of an mRNA which is important for translation by the host cell. The leader sequence is operably linked to the 5' terminus of the nucleic acid sequence encoding the polypeptide. Any leader sequence, which is functional in the cell, may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence, which is functional in the cell, may be used in the present invention.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product or a composition or a nucleic acid molecule or a peptide or polypeptide of a nucleic acid construct or vector or cell as defined herein may comprise additional component(s) than the ones specifically identified; said additional component(s) not altering the unique characteristic of the invention. In addition, reference to an element by the indefinite article "a" or "an" does not exclude the possibility that more than one of the elements is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Example 1

Figure 1:
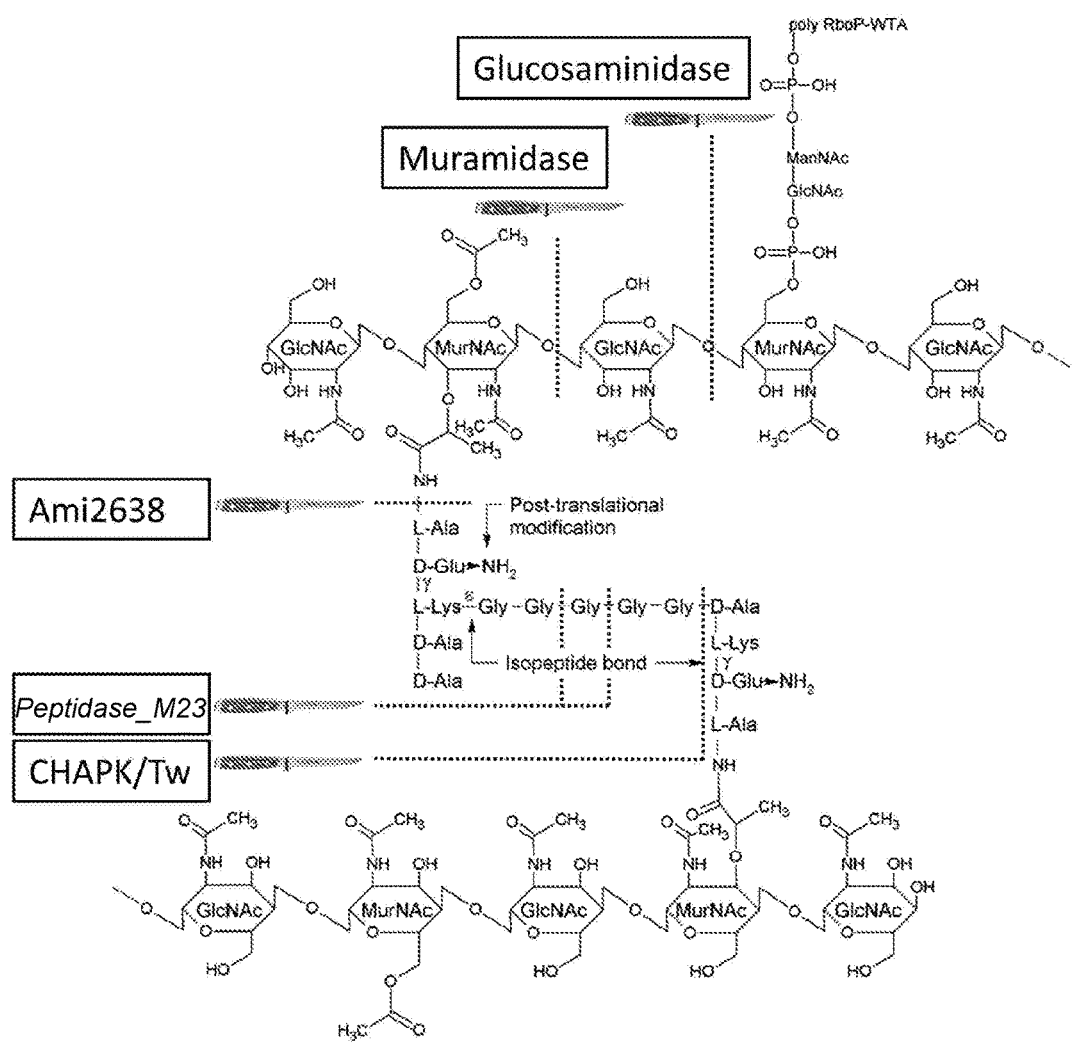
FIG. 1: target bond sites of cysteine, histidine-dependent amidohydrolases/peptidase (CHAP) domain, an endopeptidase domain (Peptidase_M23), an amidase domain (Ami2638), a muramidase domain and a glycosaminidase domain

Materials and Methods
Bacteria, Phages, and Plasmids

Bacterial strains for cloning and protein production, phages, and plasmids used in this study are listed in Table 1. *E. coli* XL1-Blue MRF' (Stratagene, La Jolla, Calif., U.S.) and *E. coli* Sure (Stratagene) served for cloning and overexpression of N-terminal 6xHis-tagged recombinant fusion proteins. Constructs containing repetitive sequences were processed in *E. coli* Sure strain. *E. coli* was cultured in Luria-Bertani (LB) medium at 37° C. supplemented with 100 µg/ml ampicillin and 30 µg/ml tetracycline for cloning, and at 30° C. with 100 µg/ml ampicillin for plasmid selection during protein expression. *Staphylococcus aureus*, BB270 NCTC8325mec used as substrate in lysis assays, was grown in, half concentrated Brain Heart Infusion medium (BHI, Biolife, Milano, Italy) at 37° C. Log phase cells from two liter cultures were harvested, PBST (50 mM $NaH_2PO_4$, 120 mM NaCl, 0.1% Tween 20, pH 7.4) washed, 100 fold concentrated and aliquots thereof were stored at −80° C.

DNA Techniques and Cloning Procedures

Cloning and construction of fusion proteins were performed using standard techniques (Loessner et al. Mol Microbiol 2002, 44: 335-349; Sambrook et al. 1989 Molecular Cloning: A Laboratory Manual. Cold Spring Harbor Laboratory Press, New York). Enzymes were purchased from New England Biolabs (Ipswitch, Mass., U.S.), Fermentas (Burlington, Canada, Roche Basel, Switzerland) and Qiagen. Endolysins and separated enzymatically active domains (EAD) coding regions from phages Φ2638a, Φ187, ΦK, and ΦTwort were in frame amplified from purified phage DNA or phage lysate. Plasmid DNA served as template for amplification of EAD encoding gene fragments of lysostaphin with High Fidelity PCR Enzyme Mix (Fermentas). Restriction sites for insert ligation into pQE-30 protein expression plasmid (Qiagen) and its derivatives were introduced by the primers. Plasmids constructed or used in this study are listed in Table 1. Protein expression plasmids were transformed into electro-competent *E. coli* XL1BlueMRF and Plasmids containing repetitive sequences into electro-competent *E. coli* Sure. DNA concentrations were determined with a spectrophotometer (NanoDrop ND-1000 Spectrophotometer, Thermo scientific, Waltham, Mass., U.S.). Sequence integrities were confirmed by nucleotide sequencing (GATC, Konstanz, Germany). Constructs bearing a single N-terminal enzymatically active domain (EAD) and a C-terminal cell wall binding domain (CBD), or a cell wall targeting domain (CWT) respectively were constructed by creating in-frame fusions of the respective coding regions with splicing overlap extension PCR (SOE). These fragments were inserted into SacI-SalI restriction sites of pQE-30Xa vector DNA. On the basis of these vectors, constructs with repetitive duplicated EADs were obtained by introducing the respective EAD coding sequences into StuI-SacI sites. For full construction principles please refer to Table 1.

Expression and Purification of Recombinant Fusion-Proteins

Protein overexpression and immobilized metal affinity chromatography (IMAC) purification of N-terminal 6xHis tagged proteins was done with minor modifications as previously described by others (Loessner et al. Appl Environ Microbiol 1996, 62: 3057-3060; Schmelcher et al. Appl Environ Microbiol 2010, 76: 5745-5756; Eichenseher et al., unpublished). Briefly, heterologous proteins expression was induced by the addition of 0.2-0.5 mM IPTG to log phase *E. coli* cultures, grown in LB medium at 30° C. Cells were further incubated at the same temperature before harvesting by centrifugation. *E. coli* were lysed in immobilization buffer (50 mM $NaH_2PO_4$, 500 mM NaCl, 5 mM imidazole, 0.1% Tween 20, pH 7.4) by a double passage through a French Pressure Cell Press (1200 psi, SLM Aminco, Urbana, Ill., U.S.) operated at 1200 psi. Insoluble cell debris was removed by centrifugation and filter sterilization (0.2 µm PES membrane, Millipore) prior to gravity flow IMAC purification in MicroBiospin (Bio-Rad, Hercules, Calif., U.S.) columns packed with low density Ni-NTA Superflow resin (Chemie Brunschwig AG, Basel, Switzerland). After column washing, 6xHis tagged proteins were eluted using elution buffer (50 mM $NaH_2PO_4$, 500 mM NaCl, 125 mM imidazole, 0.1% Tween 20, pH 7.4) and dialyzed against dialysis buffer (50 mM $NaH_2PO_4$, 100 mM NaCl, 0.1% Tween 20, pH 7.4). CHAP homologues domain containing proteins were subjected to buffer exchange using EconoPak 10DG columns (Biorad) using CHAP buffer (50 mM Tris, 5 mM $CaCl_2$, 10% glycerol, pH 7.4). Protein purities were estimated by SDS-PAGE and concentrations were determined spectrophotometrically (NanoDrop ND-1000 spectrophotmeter) or with a Pierce BCA Protein Assay Kit (Thermo Fischer Scientific, Waltham, Mass., U.S.) according to the manufacturer s manual. Proteins were stored in 50% glycerol at −20° C.

Photometric Determination of Lysis Kinetics

Lytic activities were measured in turbidity reduction assays using a Wallac VICTOR[3] TM14200 (Perkin Elmer, Waltham, Mass., U.S.) multilable counter device. Substrate cells from frozen stock were washed with buffer and adjusted to an optical density at 595 nm ($OD_{595\ nm}$) of 1+/−0.05 using Macro Cuvettes (Greiner Bio-one, Kremsmünster, Austria) and a spectrometer (BioChrom, Cambridge, UK). *Staphylococcus* lytic enzymes were diluted with buffer to equimolar quantities and if desired, subsequently pooled to obtain enzyme mixtures. 10 µl protein solutions were distributed in crystal grade multi-well polystyrene tissue culture test plates (SPL Lifesciences, Poncheon-Si, Korea) and mixed with 190 µl substrate cell suspension using a multichannel pipette. Reduction in turbidity over the time was monitored at $OD_{595\ nm}$ with vigorous plate shaking in between the reads. As a control to monitor autolytic activity under the given conditions served 10 µl buffer or water. Assays were performed in triplicates. Calculation of relative activity values were obtained as described elsewhere (Korndorfer et al. J Mol Biol 2006, 364: 678-689; Schmelcher et al., Microb Biotechnol. 2011, 4(5): 651-662). Sigmoidal lysis- and control curves were normalized to a common starting value of 1.

Results

Figure 2:
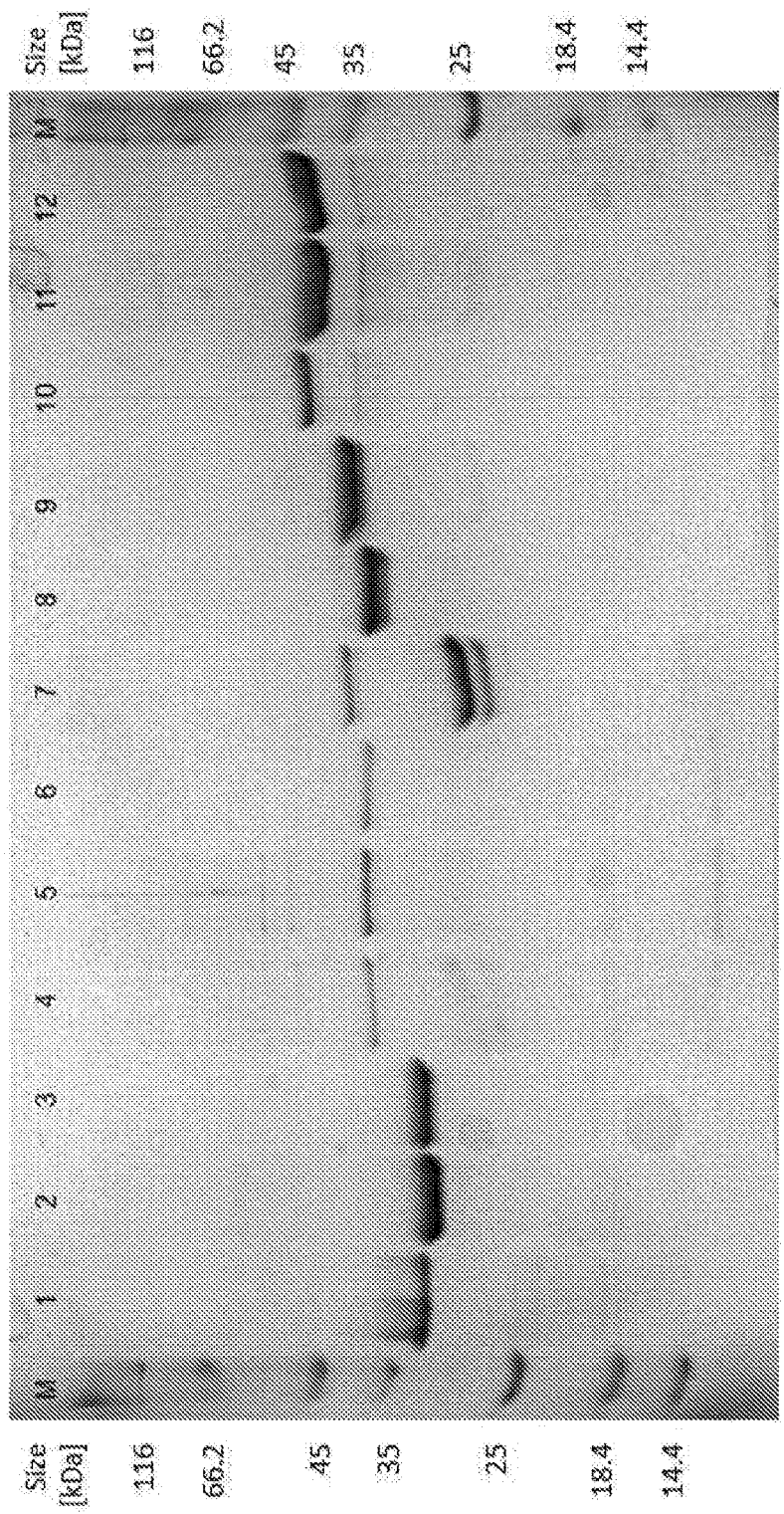
FIG. 2: SDS PAGE of partially purified proteins. 1: HXaM23-LST_CWT-LST (SEQ ID NO: 46), 2: HXaM23-LST_CWT-NM3 (SEQ ID NO: 48), 3: HXaM23-LST_CBD2638 (SEQ ID NO: 44), 4: HXaCHAPTw_CWT-NM3 (SEQ ID NO: 42), 5: HXaCHAPTw_CWT-LST (SEQ ID NO: 40), 6: HXaCHAPTw_CBD2638 (SEQ ID NO: 38), 7: HXaCHAPK_CWT-NM3 (SEQ ID NO: 36), 8: HXaCHAPK_CWT-LST (SEQ ID NO: 34), 9: HXaCHAPK_CBD2638 (SEQ ID NO: 32), 10: HXaAmi2638_CWT-NM3 (SEQ ID NO: 30), 11: HXaAmi2638_CWT-LST (SEQ ID NO: 28), 12: HXaAmi2638_CBD2638 (SEQ ID NO: 26).
Figure 3:
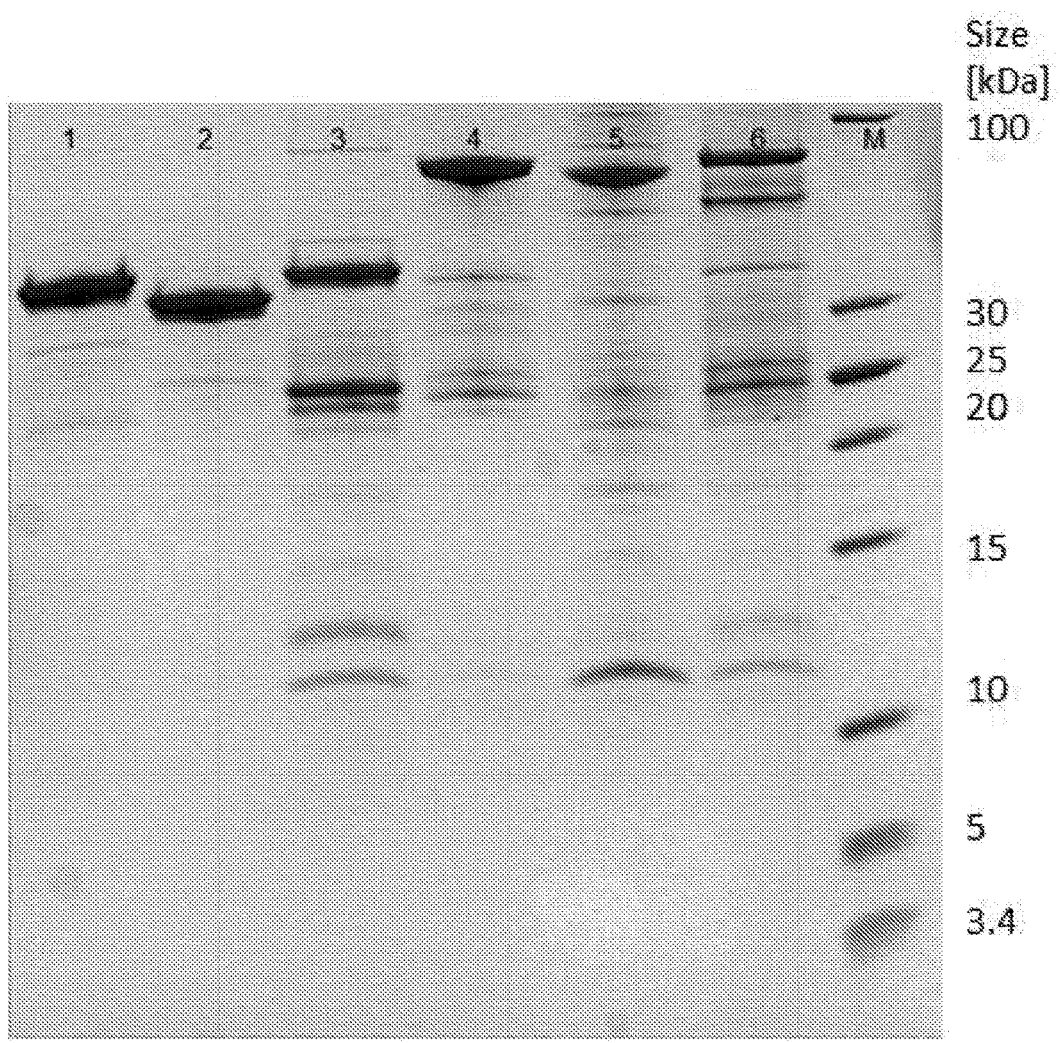
FIG. 3: SDS PAGE of partially purified proteins. 1: HXaCHAPK_CBD2638 (SEQ ID NO: 32), 2: HXaCHAPK_CWT-LST (SEQ ID NO: 34), 3: HXaCHAPK_CWT-NM3 (SEQ ID NO: 36), 4: HXaCHAPK_CHAPK_CBD2638 (SEQ ID NO: 56), 5: HXaCHAPK_CHAPK_CWT-LST (SEQ ID NO: 58), 6: HXaCHAPK_CHAPK_CWT-NM3 (SEQ ID NO: 60).
Figure 4:
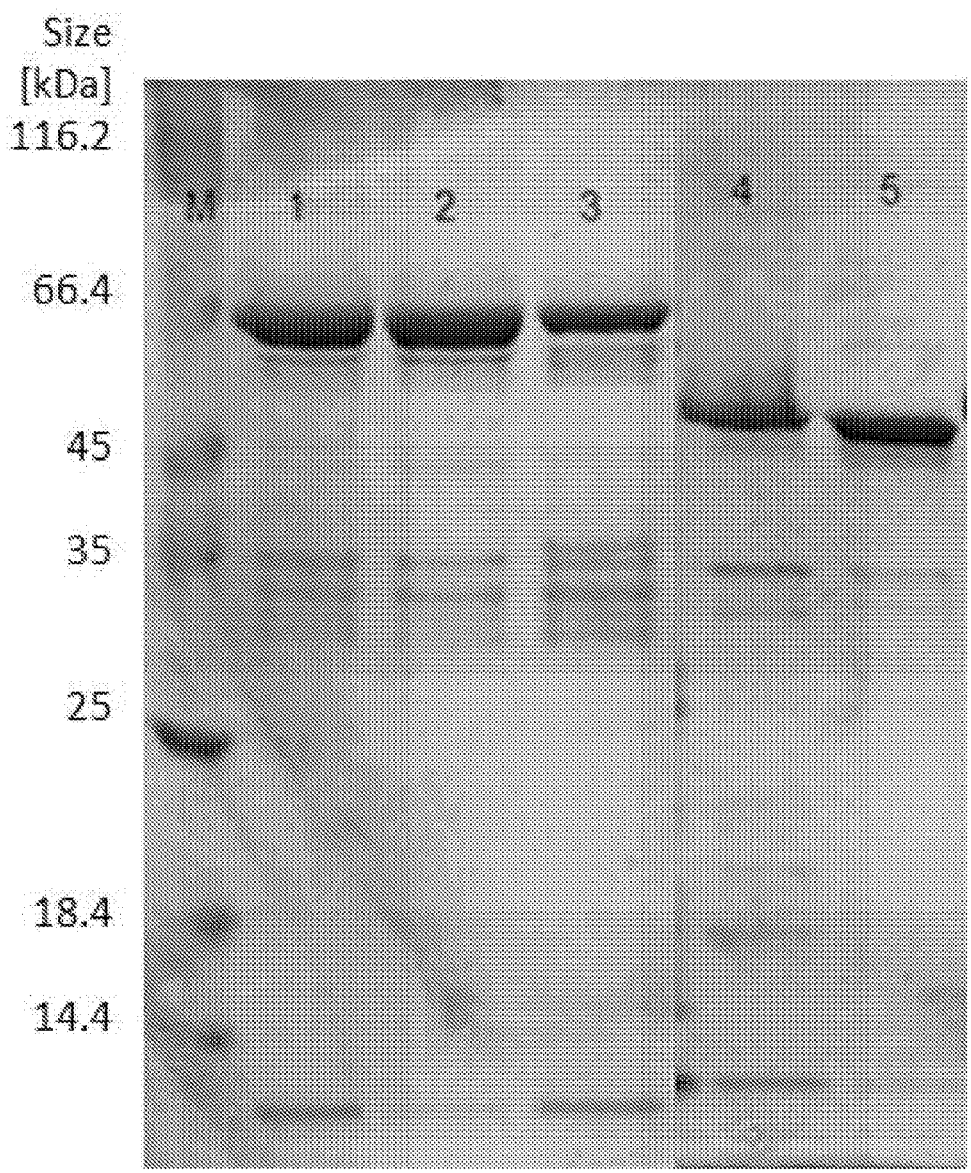
FIG. 4: SDS PAGE of partially purified proteins. 1: HXaAmi23638Ami2638_CBD2638 (SEQ ID NO: 50), 2: HXaAmi23638Ami2638_CWT-LST (SEQ ID NO: 52), 3: HXaAmi23638Ami2638_CWT-NM3 (SEQ ID NO: 54), 4: HXaM23-LST_M23-LST_CBD2638 (SEQ ID NO: 68), 5: HXaM23-LST_M23-LST_CWT-LST (SEQ ID NO: 70).

Downstream processing of cytosolic expressed *Staphylococcus* lytic proteins resulted in soluble proteins with purities depending on the protein structure and origin. The majority of the constructs had by SDS-PAGE estimated purities of up to >90% (FIGS. 2-4).

Figure 5:
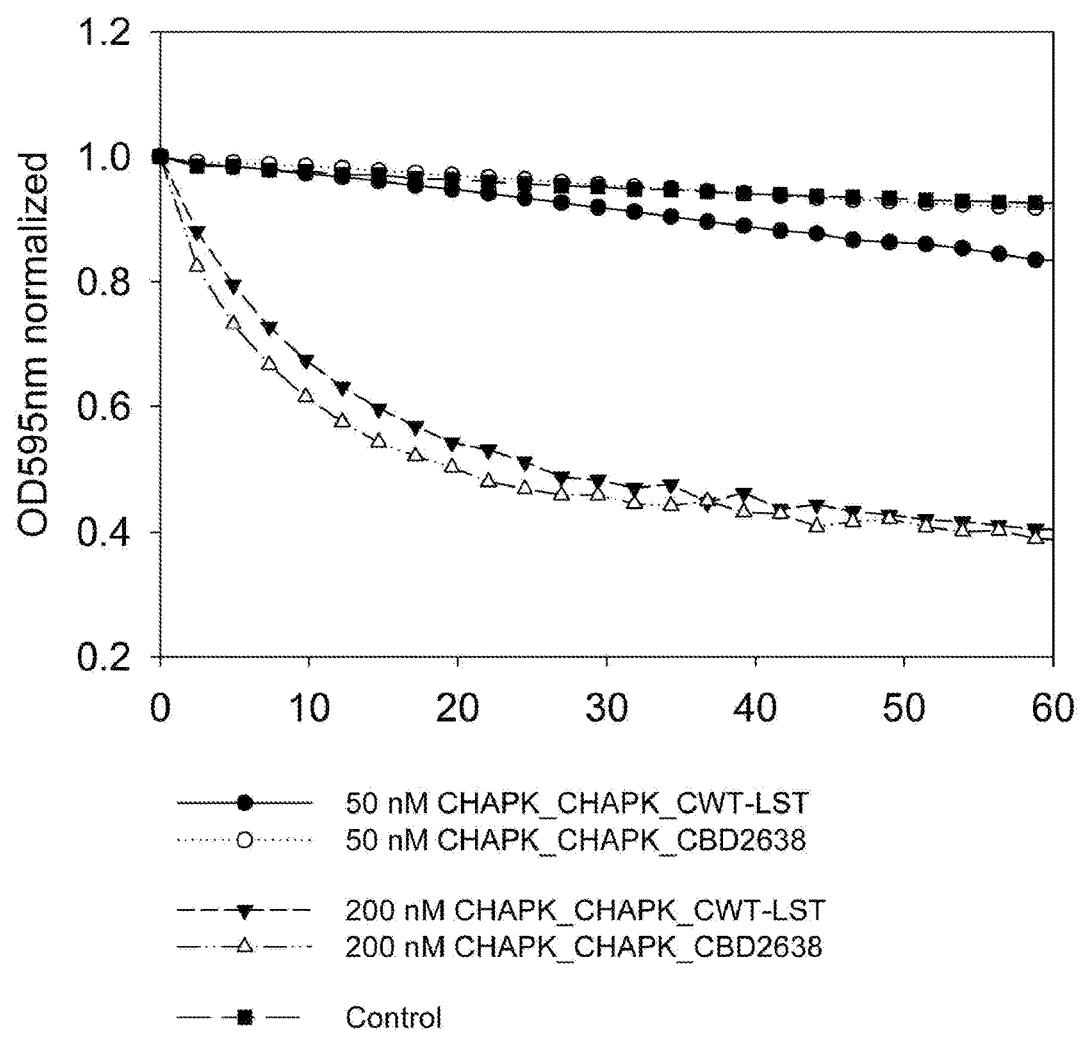
FIG. 5: Effect of CHAPK containing lysins at 50 nM and 200 nM protein assay concentration against S. aureus BB270 cells. Tested constructs: HXaCHAPK_CHAPK_CWT-LST (SEQ ID NO: 58) and HXaCHAPK_CHAPK_CBD2638 (SEQ ID NO: 56)

We tested a selection of the partially purified proteins in turbidity reduction assays (lysis assays). Individual lysins and combinations thereof were tested against *S. aureus* BB270 cells from frozen stock in PBST buffer at pH 7.4 and at different protein concentrations. CHAPK_CHAPK_CWT-LST (SEQ ID NO: 58, encoded by SEQ ID NO: 47) and CHAPK_CHAPK_CBD2638 (SEQ ID NO: 56 encoded by SEQ ID NO: 55) proteins were virtually inactive at 50 nM assay concentrations against a cell suspension set to an optical density at 595 nm (OD595 nm) of ~1, but displayed significant activities at 200 nM assay concentrations (FIG. 5).

Figure 6:
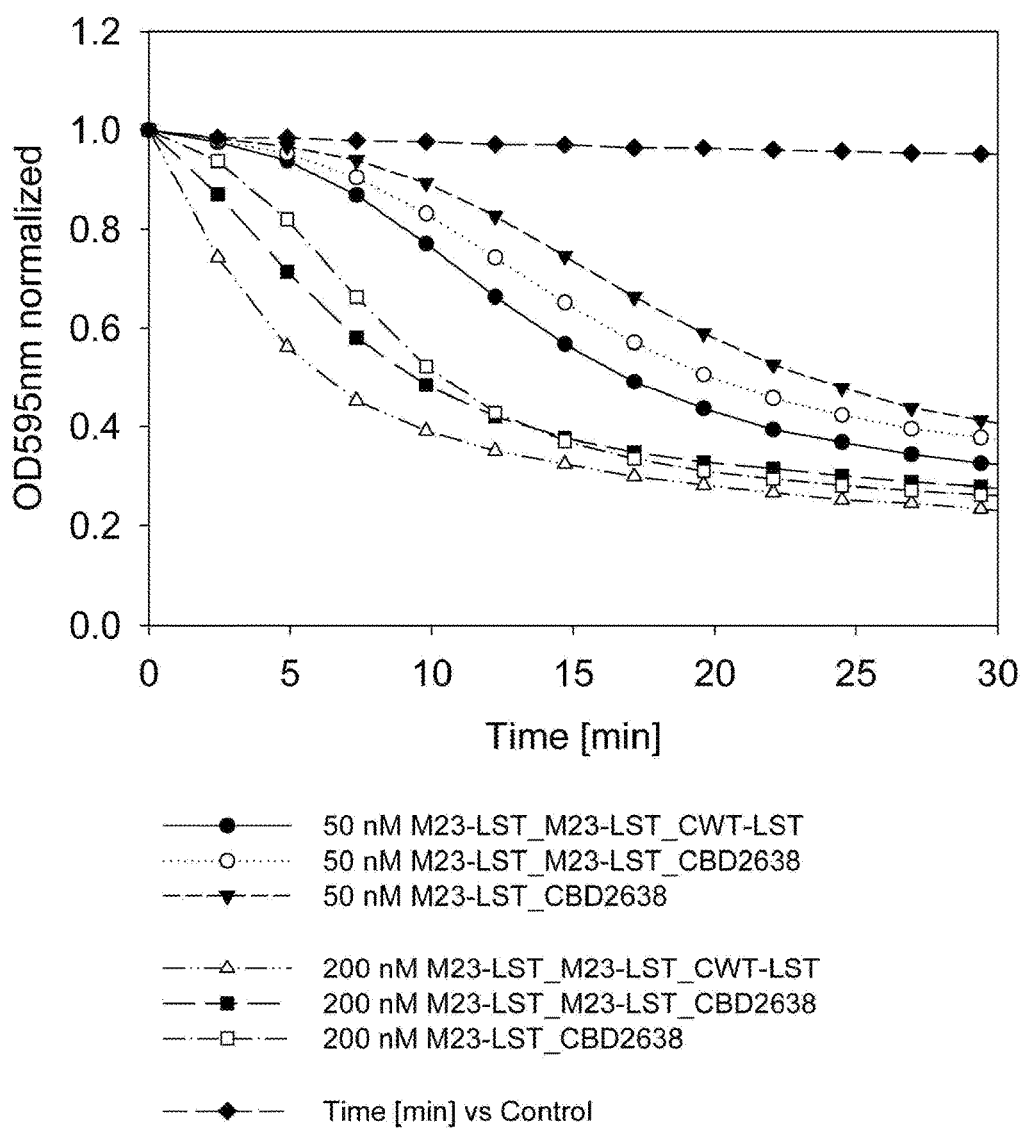
FIG. 6: Effect of M23-LST containing lysins at 50 nM and 200 nM protein assay concentration against S. aureus BB270 cells. Tested constructs: HXaM23-LST_M23-LST_CWT-LST (SEQ ID NO: 70), HXaM23-LST_M23-LST_CBD2638 (SEQ ID NO: 68) and HXaM23-LST_CWT-LST (SEQ ID NO: 46)

Using M23-LST (SEQ ID NO: 16, encoded by SEQ ID NO: 15) containing proteins in an identical assay setup, best results were achieved using M23-LST_M23-LST_CWT-LST (SEQ ID NO: 70, encoded by SEQ ID NO: 69) at 200 nM assay concentration. The CWT-LST (SEQ ID NO: 4, encoded by SEQ ID NO: 3) appears to be superior to CBD2638 (SEQ ID NO: 6, encoded by SEQ ID NO: 5). Furthermore, repetitive double M23-LST variants (SEQ ID NO: 68 and 70 encoded by SEQ ID NO: 67 and 69, respectively) were found superior to single M23-LST (SEQ ID NO: 44 and 46, encoded by SEQ ID NO: 43 and 45, respectively). This effect was found more pronounced at 50 nM protein concentrations. For full results please refer to FIG. 6.

Figure 7:
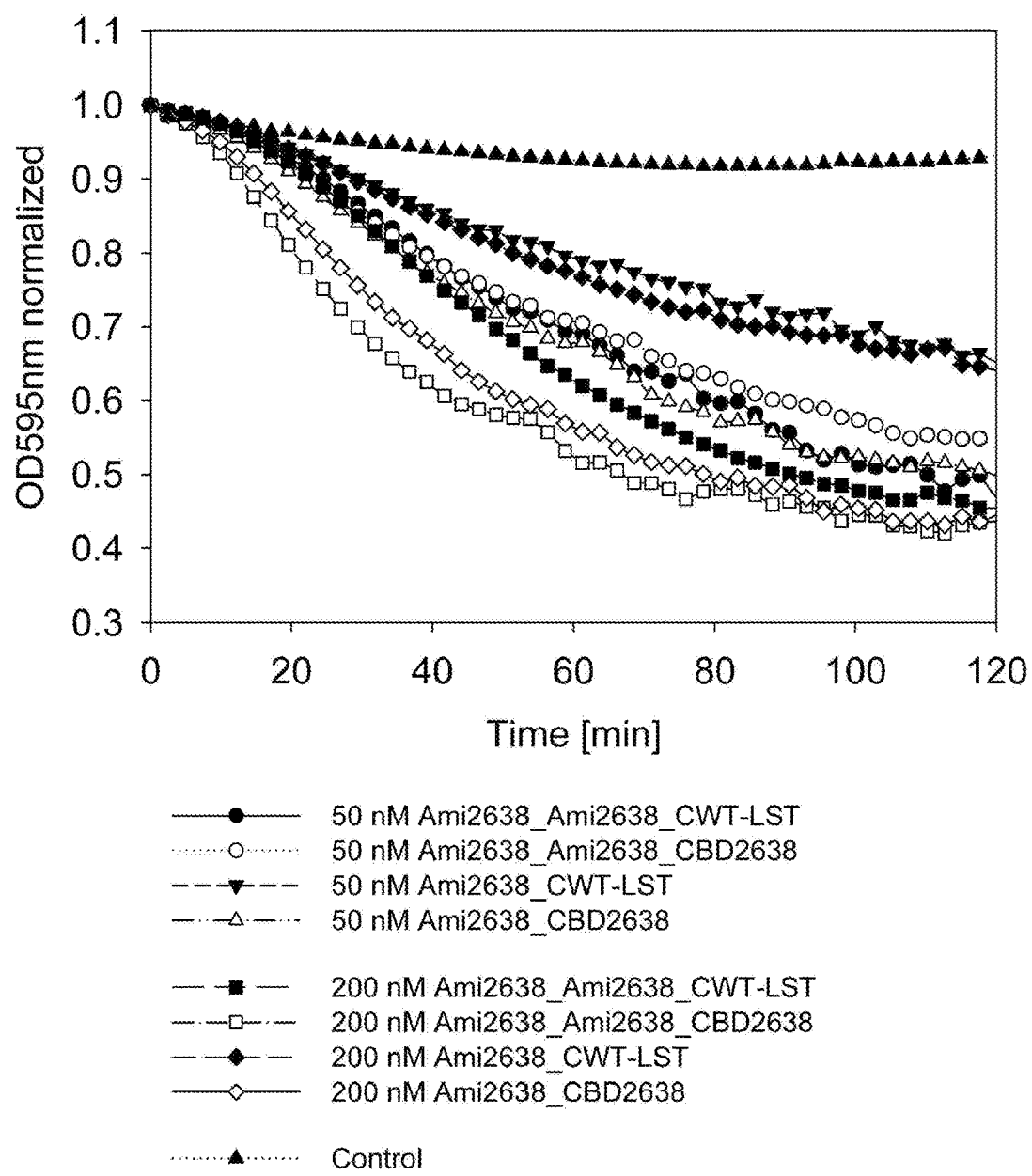
FIG. 7: Effect of Ami2638 containing lysins at 50 nM and 200 nM protein assay concentration against S. aureus BB270 cells. Tested constructs: HXaAmi2638_Ami2638_CWT-LST (SEQ ID NO: 52), HXaAmi2638_Ami2638_CBD2638 (SEQ ID NO: 50), HXaAmi2638_CWT-LST (SEQ ID NO: 28), HXaAmi2638_CBD2638 (SEQ ID NO: 26)

All lysins built with Ami2638 (SEQ ID NO: 18, encoded by SEQ ID NO: 17) were significantly less active compared to CHAPK (SEQ ID NO: 10, encoded by SEQ ID NO: 9) and M23-LST (SEQ ID NO: 16, encoded by SEQ ID NO: 15) proteins. Here, CBD2638 (SEQ ID NO: 6 encoded by SEQ ID NO: 5) was superior to CWT-LST (SEQ ID NO: 4, encoded by SEQ ID NO: 3). Duplication of the catalytic domain had little effect when combined with CBD2638 (SEQ ID NO: 6, encoded by SEQ ID NO: 5), but duplication added a positive effect on lysis kinetics when combined with CWT-LST (SEQ ID NO: 4, encoded by SEQ ID NO: 3) (FIG. 7).

Figure 8:
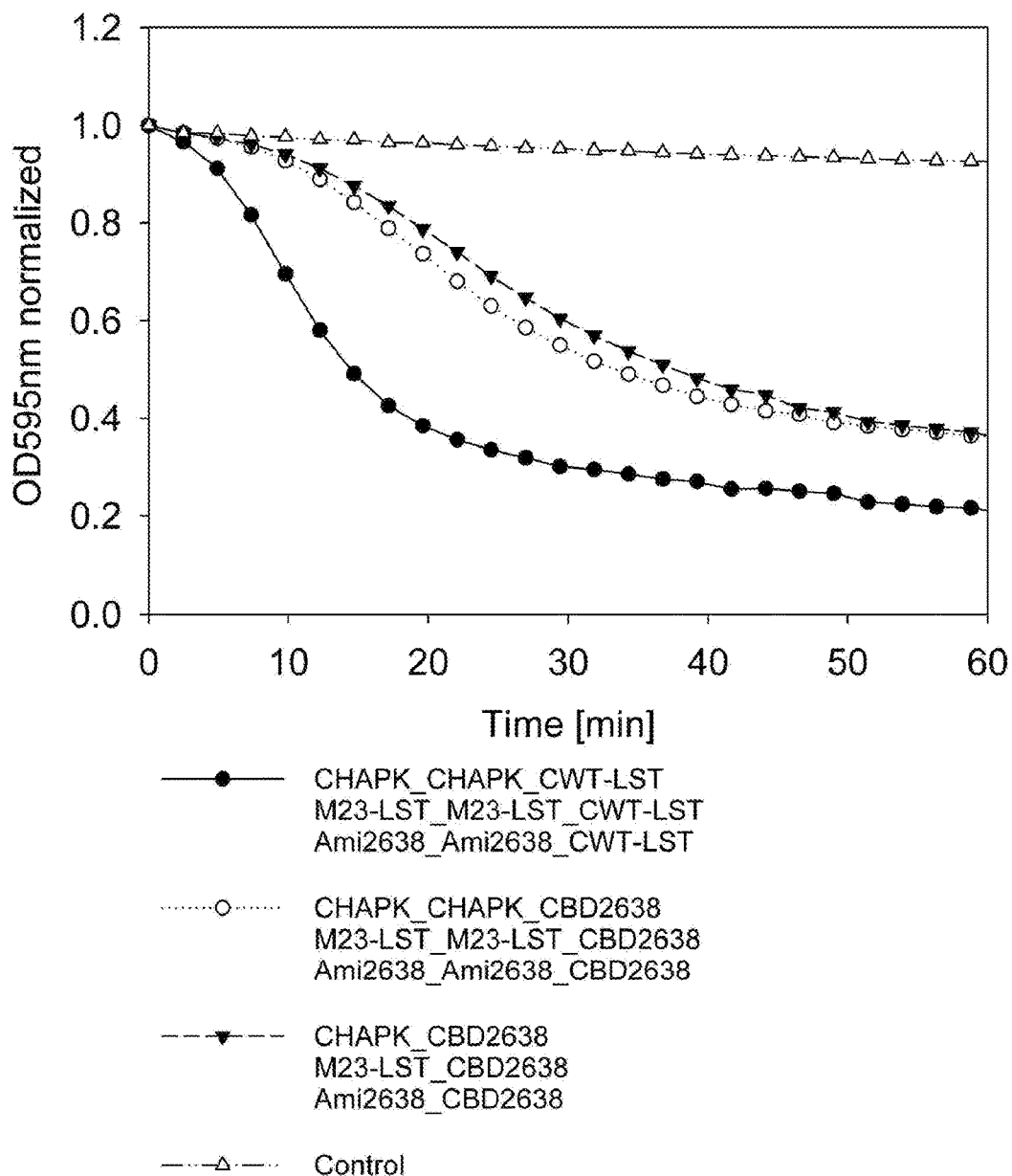
FIG. 8: Comparison of 50 nM protein mixtures (16.67 nM each protein) with equal CBDs. Tested constructs: HXaCHAPK_CHAPK_CWT-LST (SEQ ID NO: 58), HXaM23-LST_M23-LST_CWT-LST (SEQ ID NO: 70), HXaAmi2638_Ami2638_CWT-LST (SEQ ID NO: 52), HXaCHAPK_CHAPK_CBD2638 (SEQ ID NO: 56), HXaM23-LST_M23-LST_CBD2638 (SEQ ID NO: 68), HXaAmi2638_Ami2638_CBD2638 (SEQ ID NO: 50), HXaCHAPK_CBD2638 (SEQ ID NO: 32), HXaM23-LST_CBD2638 (SEQ ID NO: 44) and HXaAmi2638_CBD2638 (SEQ ID NO: 26).
Figure 9:
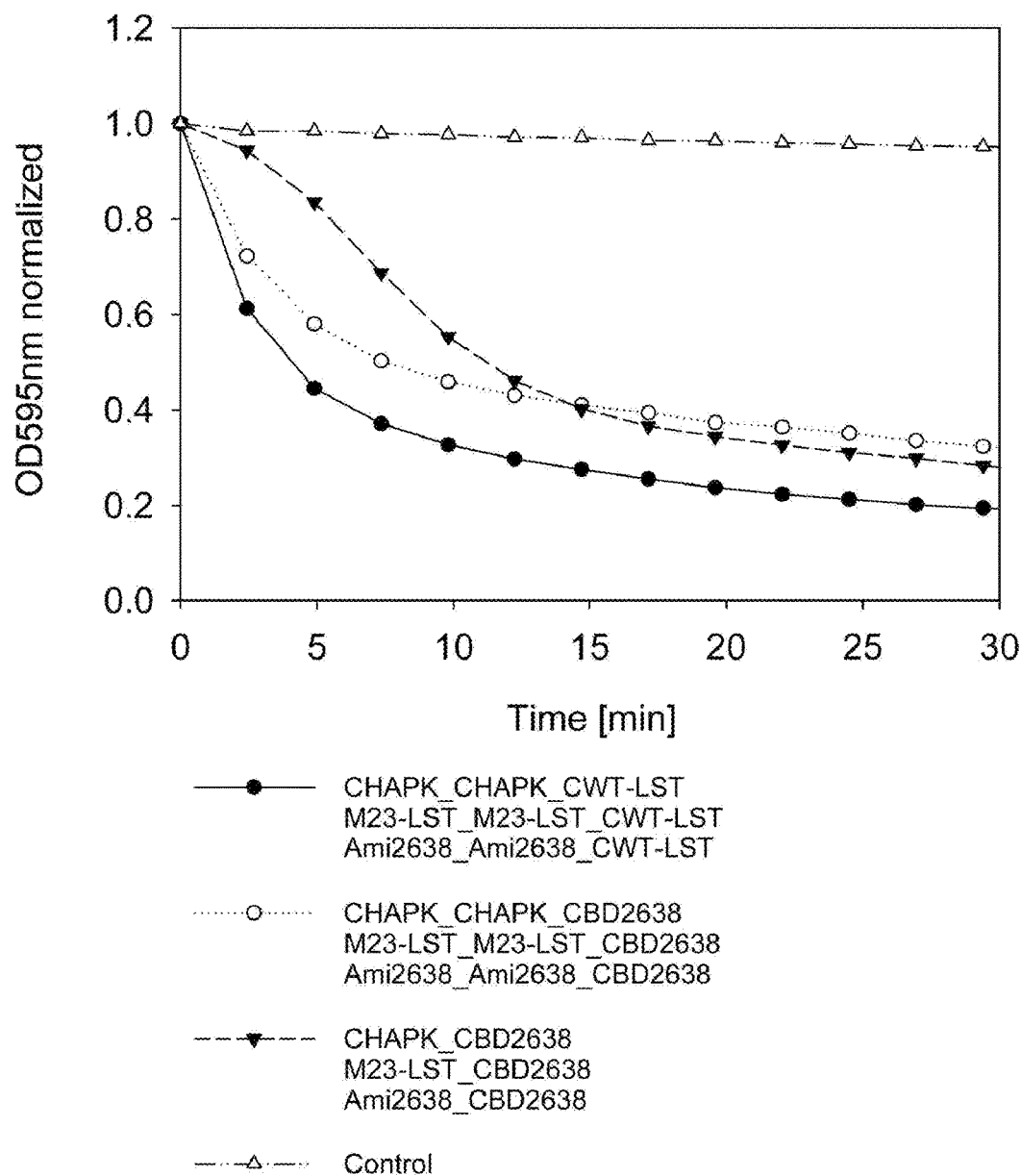
FIG. 9: Comparison of 200 nM protein mixtures (66.67 nM each protein) with equal CBDs. Tested constructs: HXaCHAPK_CHAPK_CWT-LST (SEQ ID NO: 58), HXaM23-LST_M23-LST_CWT-LST (SEQ ID NO: 70), HXaAmi2638_Ami2638 CWT-LST (SEQ ID NO: 52), HXaCHAPK_CHAPK_CBD2638 (SEQ ID NO: 56), HXaM23-LST_M23-LST CBD2638 (SEQ ID NO: 68), HXaAmi2638_Ami2638_CBD2638 (SEQ ID NO: 50), HXaCHAPK_CBD2638 (SEQ ID NO: 32), HXaM23-LST_CBD2638 (SEQ ID NO: 44) and HXaAmi2638_CBD2638 (SEQ ID NO: 26).

We also compared activities of mixtures of proteins built with CWT-LST (SEQ ID NO: 4, encoded by SEQ ID NO: 3) or CBD2638 (SEQ ID NO: 6, encoded by SEQ ID NO: 5). At low protein concentrations (16.67 nM each, or 50 nM total protein concentration respectively), mixtures of CWT-LST (SEQ ID NO: 58, 70 and 52) proteins were found significantly more active than mixtures of CBD2638 (SEQ ID NO: 56, 68 and 50) proteins. Furthermore, duplication of the EADs had little effect on lysis kinetics in CBD2638 constructs mixtures (SEQ ID NO: 56, 68 and 50 as compared to SEQ ID NO: 32, 44 and 26) (FIG. 8). Increasing the assay concentration of proteins to 200 nM (66.67 nM each) resulted in virtually equal activities of CWT-LST and CBD2638 constructs with repetitive doubled EADs. Although it appears that the lysis curve of CBD2638 constructs (FIG. 9) runs "above" the curve of CWT-LST constructs, we estimate lysis kinetics being equal. This is simply because assays were performed in 96 well plates and OD595 nm measurements started not at the same time points after lysine addition. The first measurement of the curve was already at a stage were lysis commenced, so normalization of the curve to an initial OD595 nm of 1 shifted the curve to higher values. Unlike at 50 nM protein concentrations, mixtures of CBD2638 constructs with only single EAD were not found equally active as repetitive doubled EAD-CBD2638 constructs, but showed slower lysis kinetics.

Figure 10:
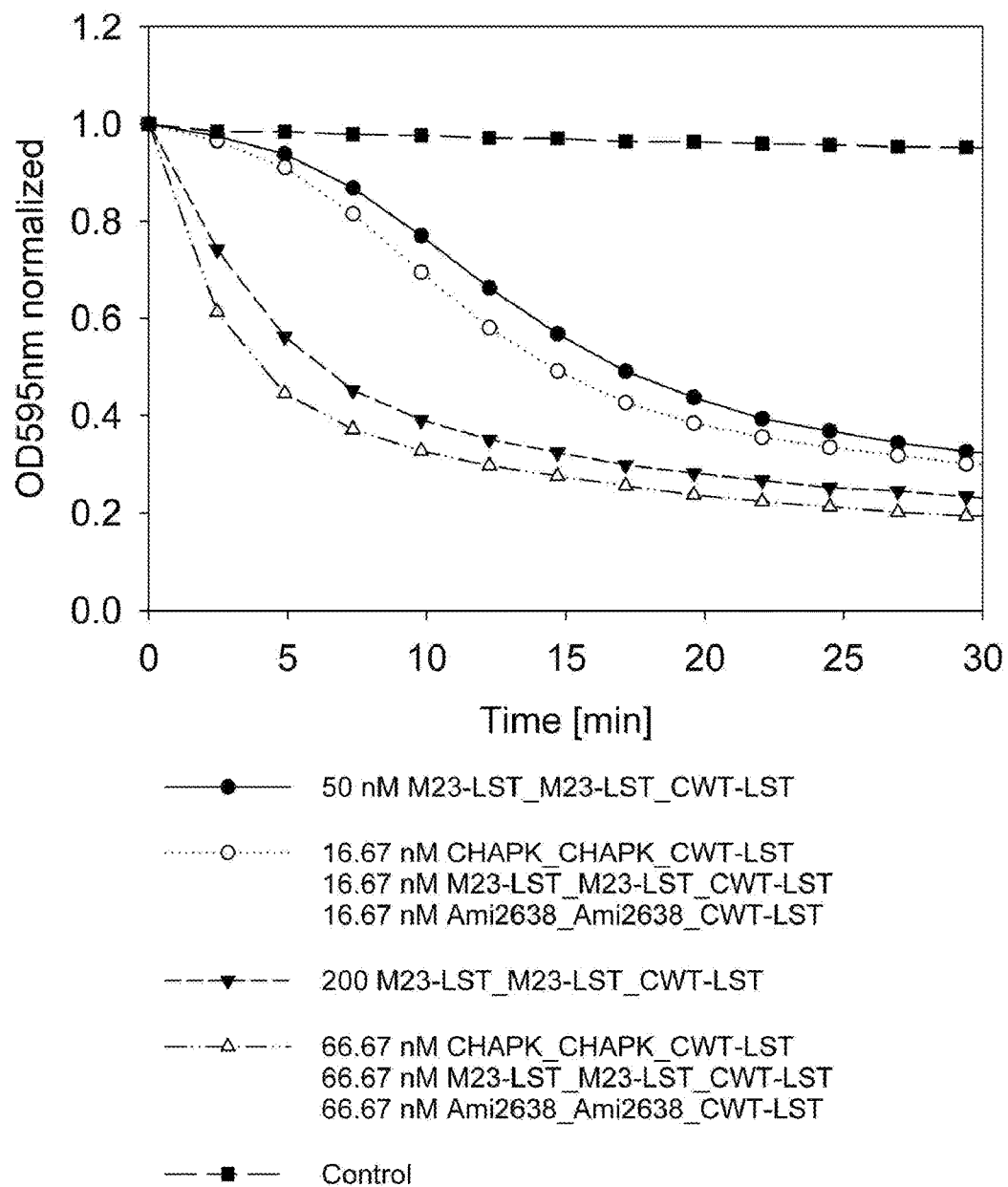
FIG. 10: Comparison of protein mixtures of HXaCHAPK_CHAPK_CWT-LST (SEQ ID NO: 58), HXaM23-LST_M23-LST_CWT-LST (SEQ ID NO: 70) and HXaAmi2638_Ami2638_CWT-LST (SEQ ID NO: 52) at (16.67 nM and 66.67 nM of each protein) with 50 nM and 200 nM of the reference protein M23-LST_M23-LST_CWT-LST (SEQ ID NO: 70).
Figure 11:
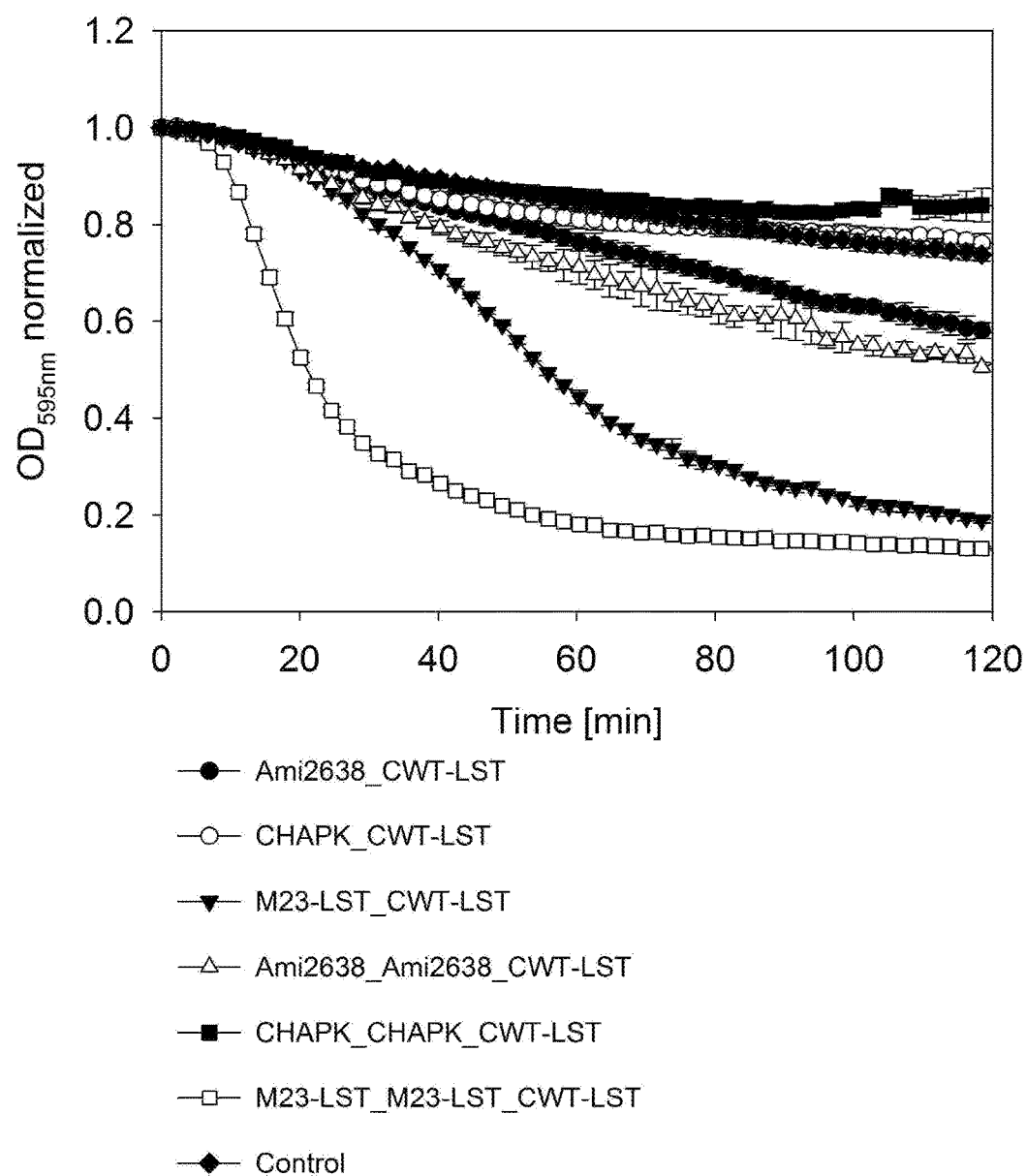
FIG. 11: Effect of CHAPK, M23 and Ami containing lysins at 30 nM protein assay concentration against S. aureus BB270 cells. Tested constructs: HXaAmi2638_CWT-LST (SEQ ID NO: 28), HXaCHAPK_CWT-LST (SEQ ID NO: 34), HXaM23-LST_CWT-LST (SEQ ID NO: 46), HXaAmi2638_Ami2638_CWT-LST (SEQ ID NO: 52), HXaCHAPK_CHAPK_CWT-LST (SEQ ID NO: 58) and HXaM23-LST_M23-LST_CWT-LST (SEQ ID NO: 70).
Figure 12:
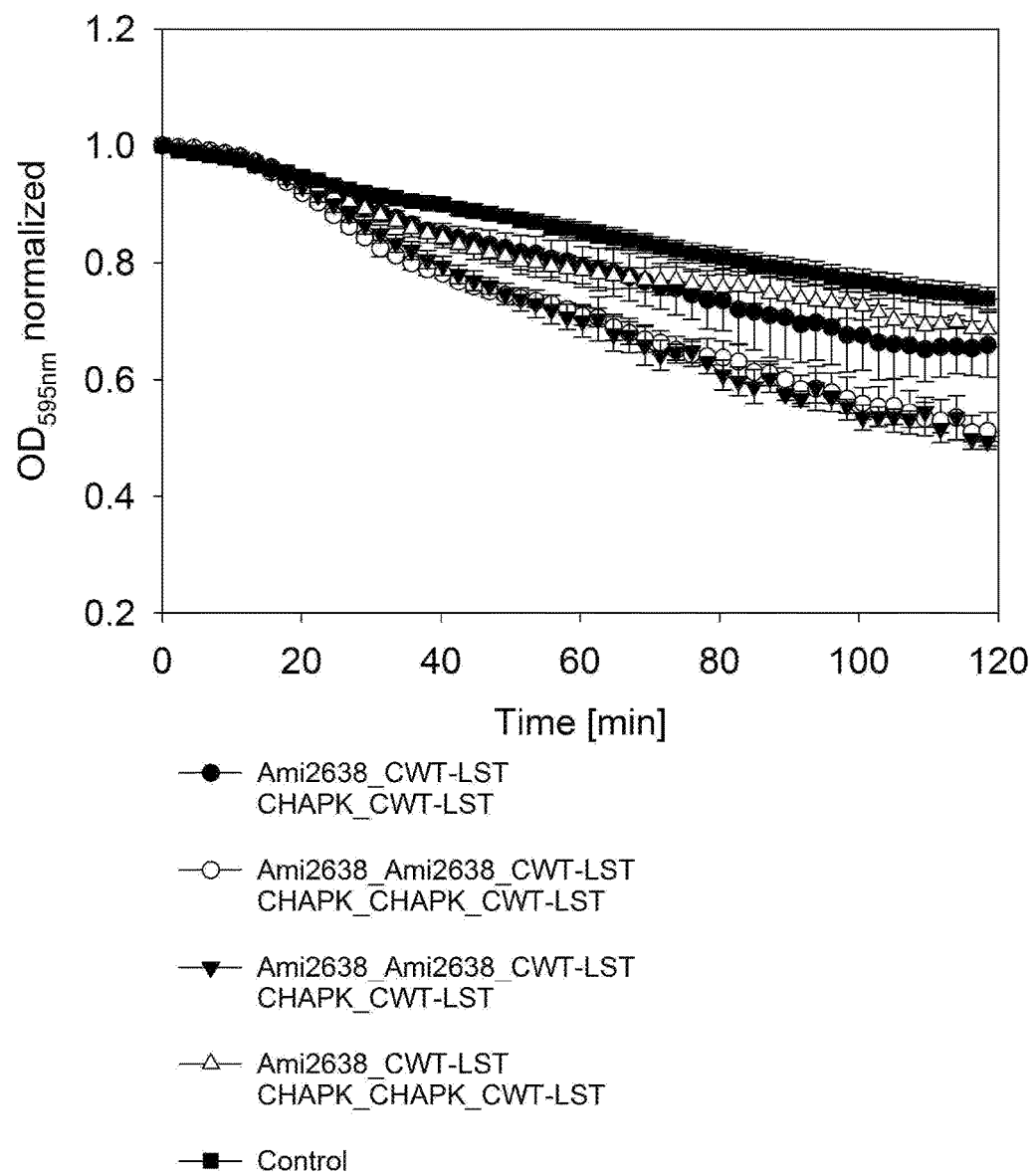
FIG. 12: Effect of 30 nM protein mixtures (15 nM each protein). Tested constructs: HXaAmi2638_CWT-LST (SEQ ID NO: 28), HXaCHAPK_CWT-LST (SEQ ID NO: 34), HXaAmi2638_Ami2638_CWT-LST (SEQ ID NO: 52) and HXaCHAPK_CHAPK_CWT-LST (SEQ ID NO: 58).
Figure 13:
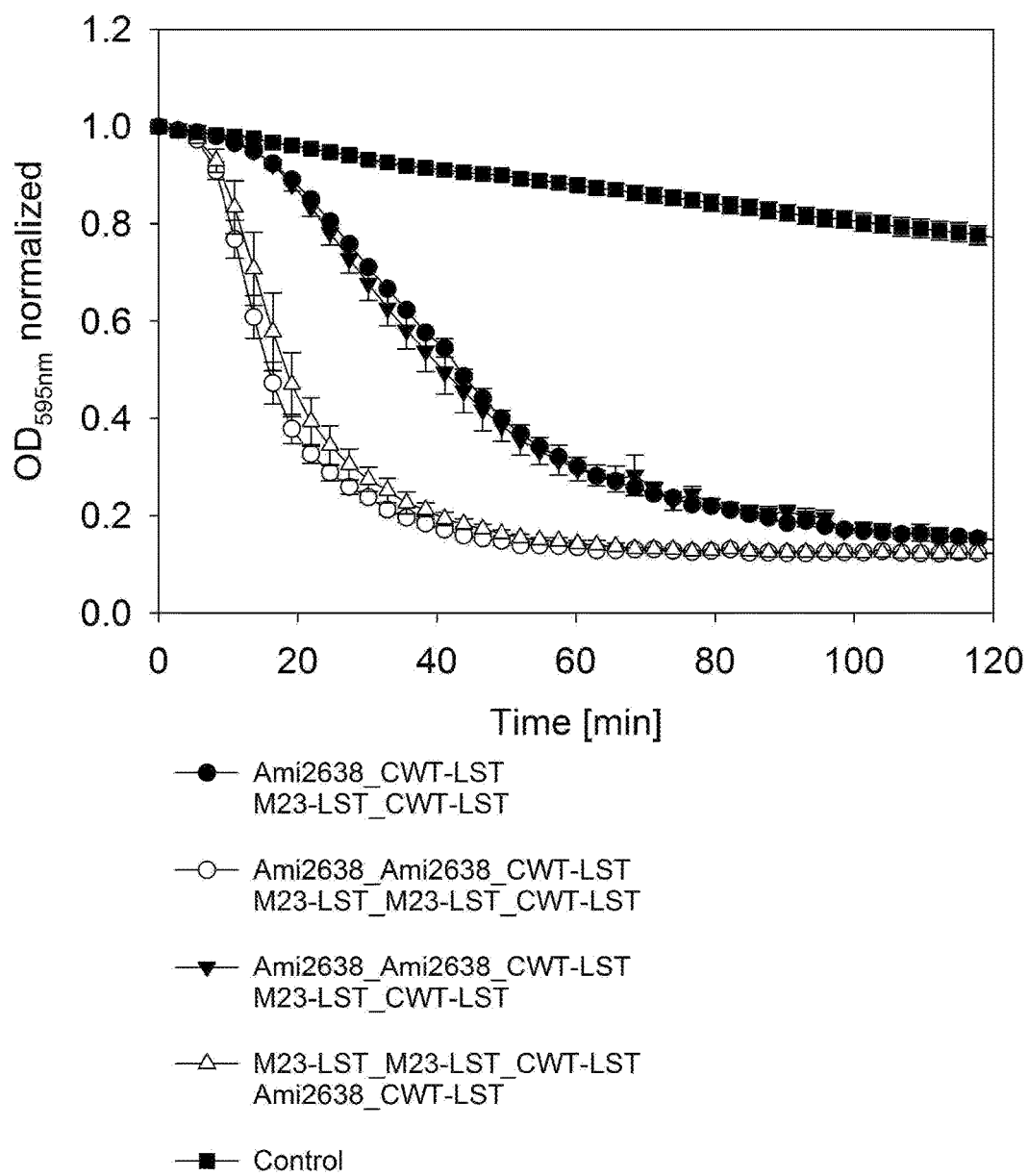
FIG. 13: Effect of 30 nM protein mixtures (15 nM each protein). Tested constructs: HXaAmi2638_CWT-LST (SEQ ID NO: 28), HXaM23-LST_CWT-LST (SEQ ID NO: 46), HXaAmi2638_Ami2638_CWT-LST (SEQ ID NO: 52) and HXaM23-LST_M23-LST_CWT-LST (SEQ ID NO: 70).
Figure 14:
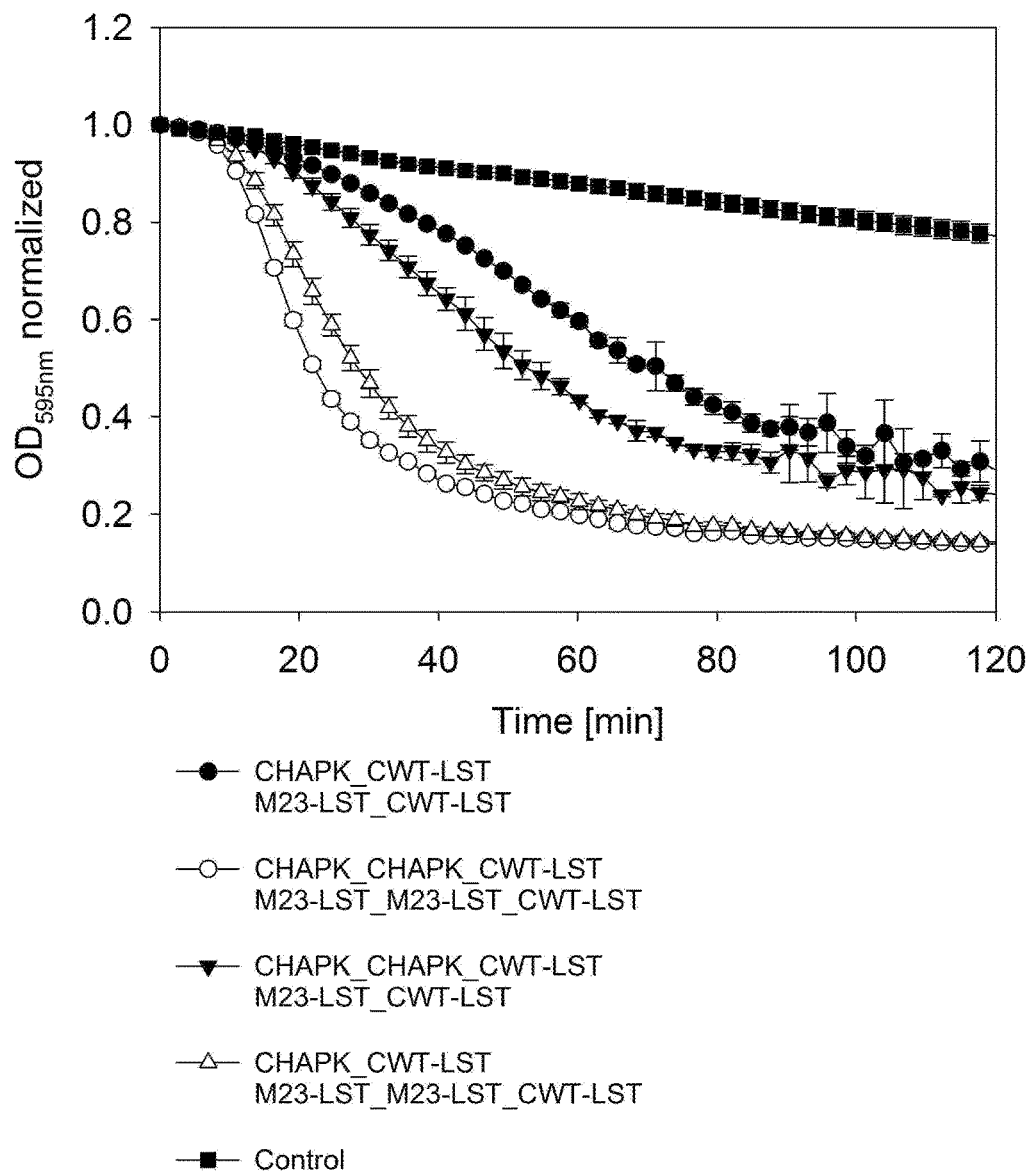
FIG. 14: Effect of 30 nM protein mixtures (15 nM each protein). Tested constructs: HXaCHAPK_CWT-LST (SEQ ID NO: 34), HXaM23-LST_CWT-LST (SEQ ID NO: 46), HXaCHAPK_CHAPK_CWT-LST (SEQ ID NO: 58) and HXaM23-LST_M23-LST_CWT-LST (SEQ ID NO: 70).
Figure 15:
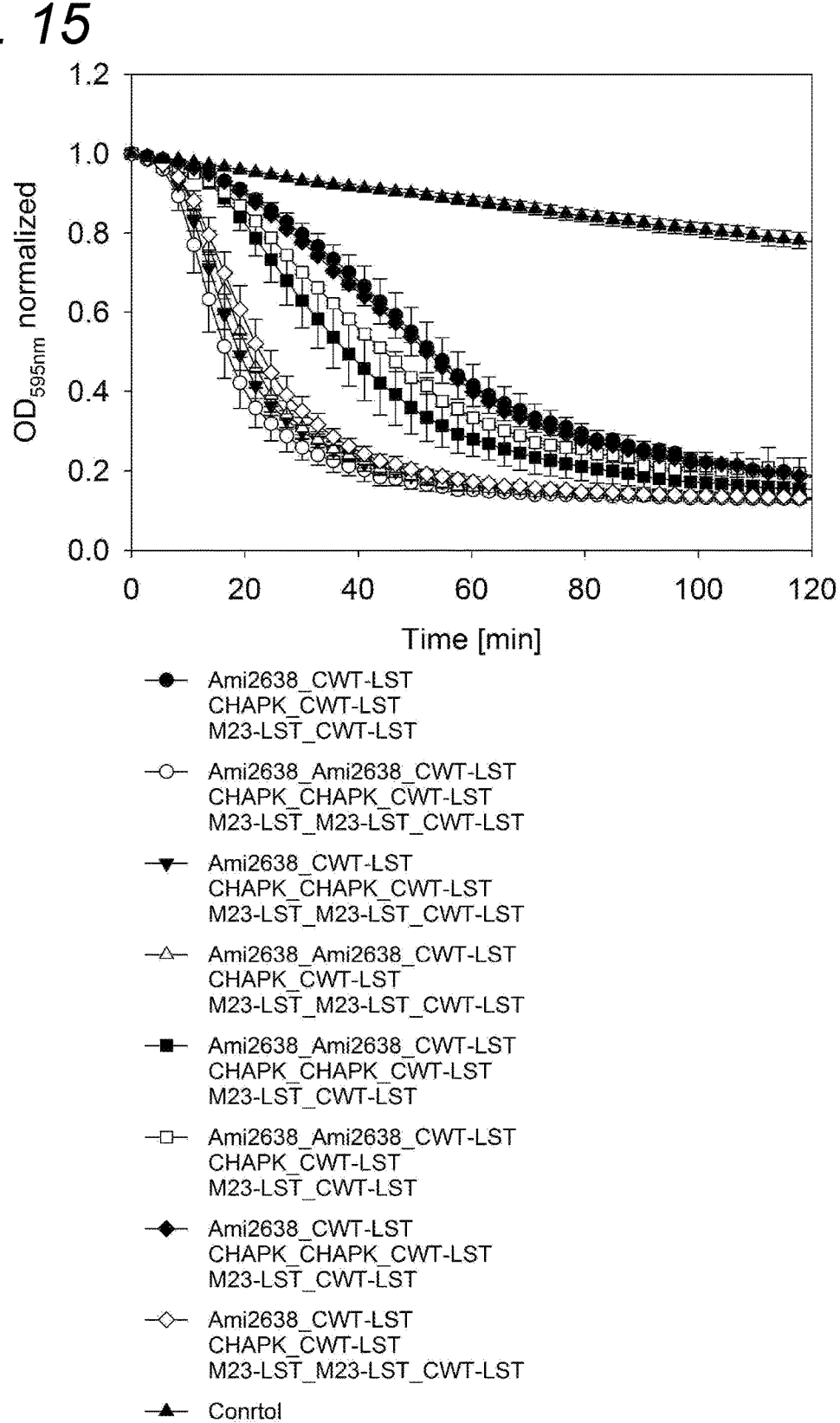
FIG. 15: Effect of 30 nM protein mixtures (10 nM each protein). Tested constructs: HXaAmi2638_CWT-LST (SEQ ID NO: 28), HXaCHAPK_CWT-LST (SEQ ID NO: 34), HXaM23-LST_CWT-LST (SEQ ID NO: 46), HXaAmi2638_Ami2638_CWT-LST (SEQ ID NO: 52), HXaCHAPK_CHAPK_CWT-LST (SEQ ID NO: 58) and HXaM23-LST_M23-LST_CWT-LST (SEQ ID NO: 70).
Figure 16:
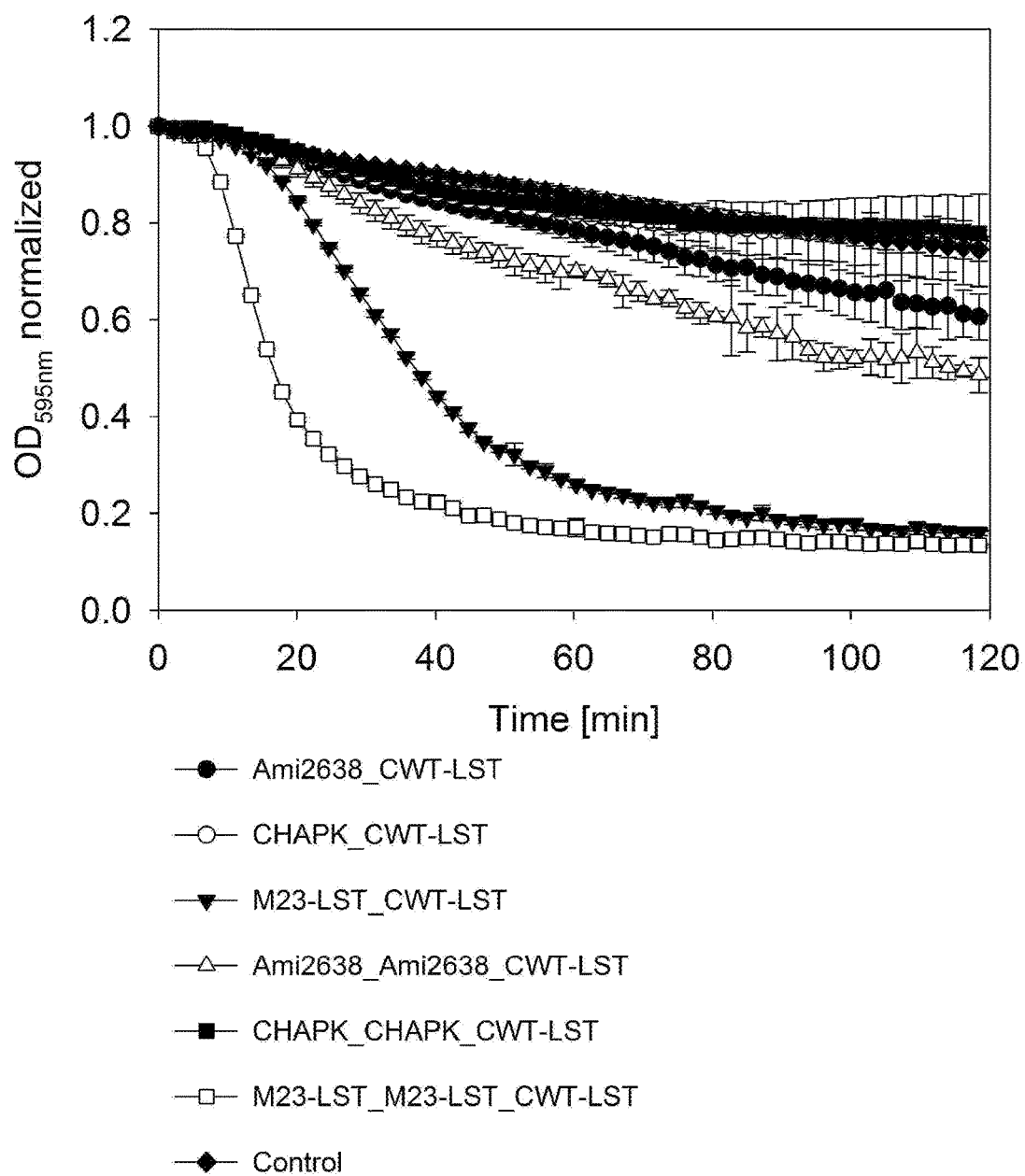
FIG. 16: Effect of CHAPK, M23 and Ami containing lysins at 50 nM protein assay concentration against S. aureus BB270 cells. Tested constructs: HXaAmi2638_CWT-LST (SEQ ID NO: 28), HXaCHAPK_CWT-LST (SEQ ID NO: 34), HXaM23-LST_CWT-LST (SEQ ID NO: 46), HXaAmi2638_Ami2638_CWT-LST (SEQ ID NO: 52), HXaCHAPK_CHAPK_CWT-LST (SEQ ID NO: 58) and HXaM23-LST_M23-LST_CWT-LST (SEQ ID NO: 70).
Figure 17:
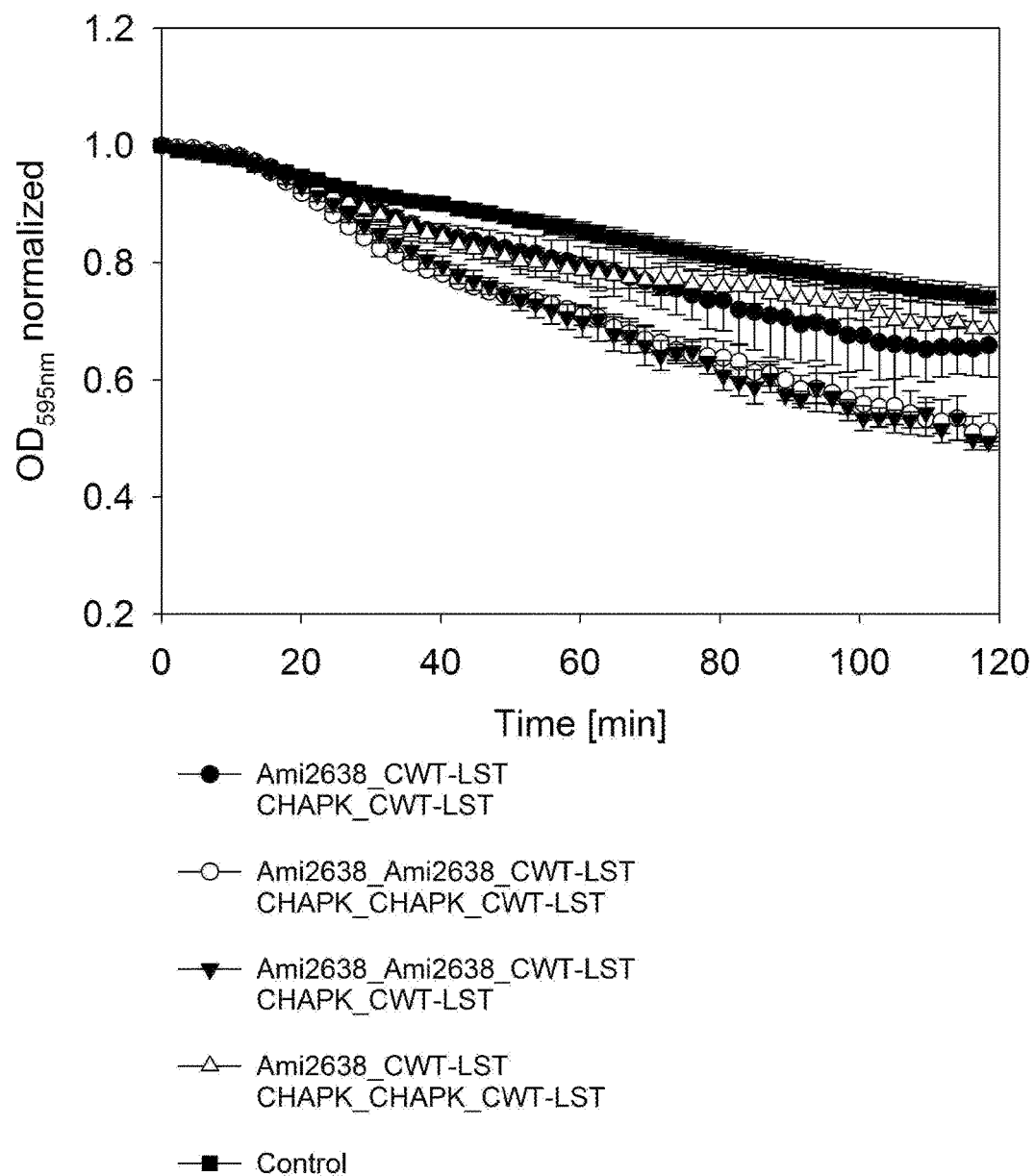
FIG. 17: Effect of 50 nM protein mixtures (25 nM each protein). Tested constructs: HXaAmi2638_CWT-LST (SEQ ID NO: 28), HXaCHAPK_CWT-LST (SEQ ID NO: 34), HXaAmi2638_Ami2638_CWT-LST (SEQ ID NO: 52) and HXaCHAPK_CHAPK_CWT-LST (SEQ ID NO: 58).
Figure 18:
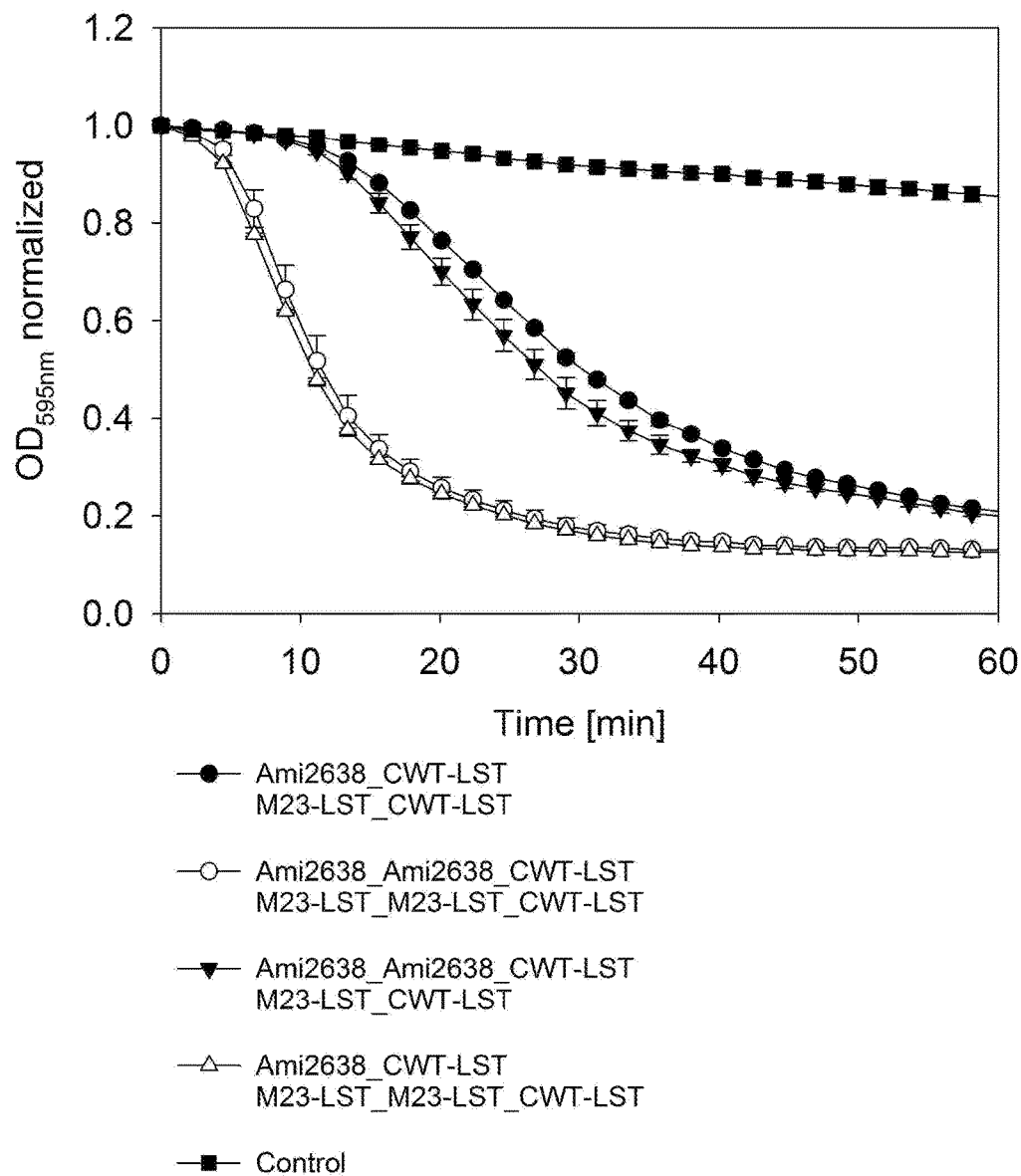
FIG. 18: Effect of 50 nM protein mixtures (25 nM each protein). Tested constructs: HXaAmi2638_CWT-LST (SEQ ID NO: 28), HXaM23-LST_CWT-LST (SEQ ID NO: 46), HXaAmi2638_Ami2638_CWT-LST (SEQ ID NO: 52) and HXaM23-LST_M23-LST_CWT-LST (SEQ ID NO: 70).
Figure 19:
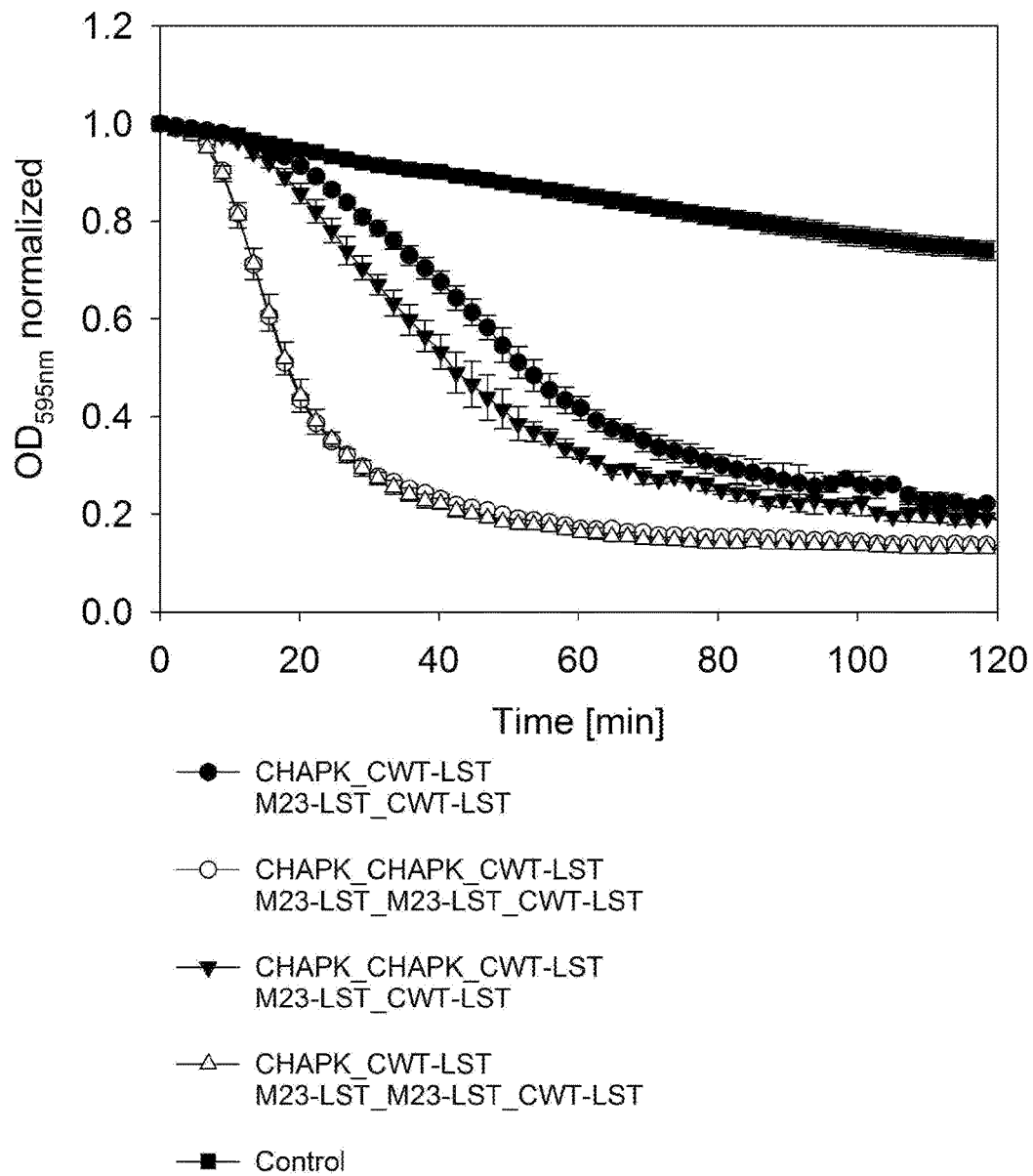
FIG. 19: Effect of 50 nM protein mixtures (25 nM each protein). Tested constructs: HXaCHAPK_CWT-LST (SEQ ID NO: 34), HXaM23-LST_CWT-LST (SEQ ID NO: 46), HXaCHAPK_CHAPK_CWT-LST (SEQ ID NO: 58) and HXaM23-LST_M23-LST_CWT-LST (SEQ ID NO: 70).
Figure 20:
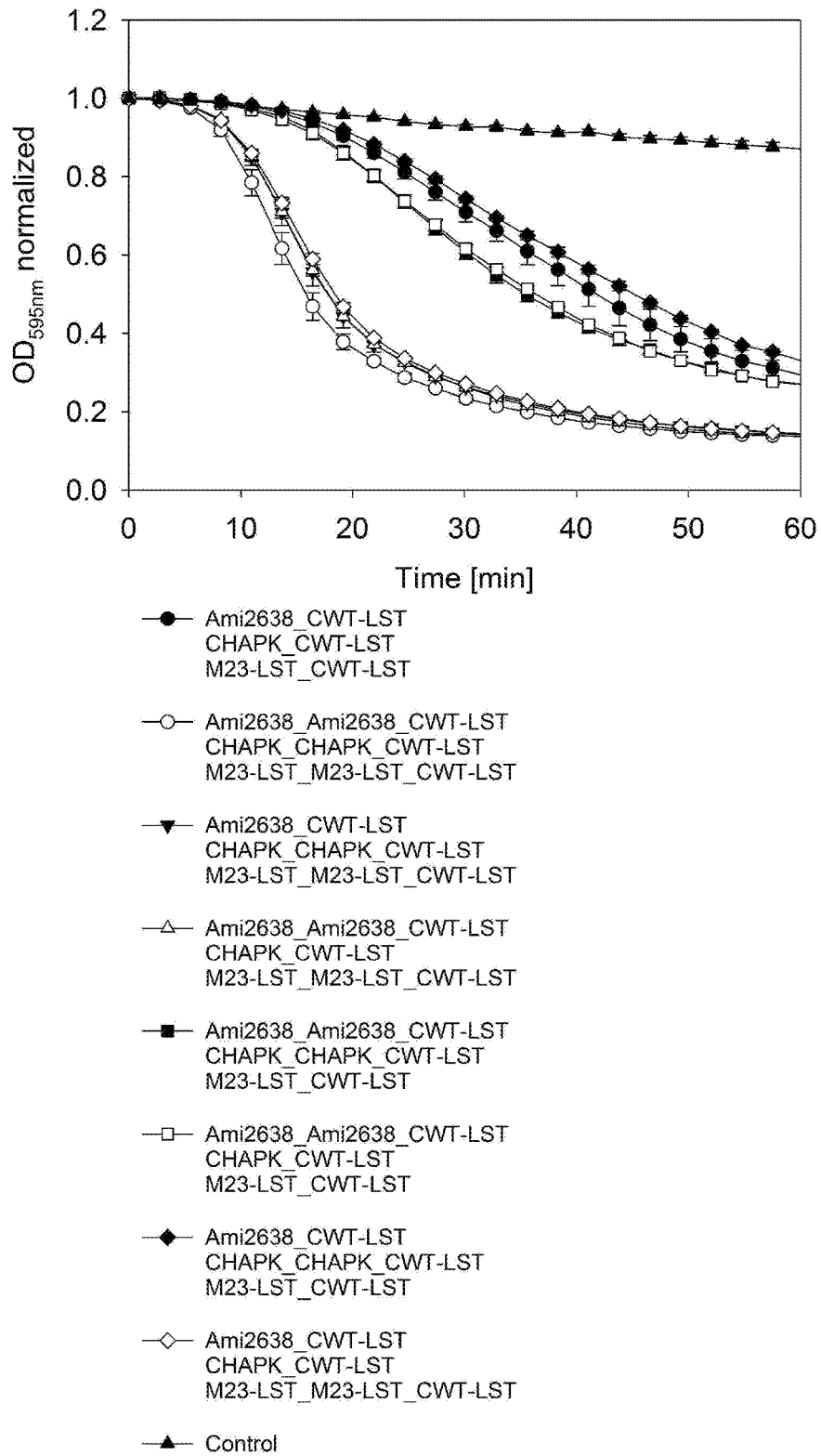
FIG. 20: Effect of 50 nM protein mixtures (16.67 nM each protein). Tested constructs: HXaAmi2638_CWT-LST (SEQ ID NO: 28), HXaCHAPK_CWT-LST (SEQ ID NO: 34), HXaM23-LST_CWT-LST (SEQ ID NO: 46), HXaAmi2638_Ami2638_CWT-LST (SEQ ID NO: 52), HXaCHAPK_CHAPK_CWT-LST (SEQ ID NO: 58) and HXaM23-LST_M23-LST_CWT-LST (SEQ ID NO: 70).

Finally, we compared the most effective mixture consisting of Ami2638_Ami2638_CWT-LST (SEQ ID NO: 52, encoded by SEQ ID NO: 51), CHAPK_CHAPK_CWT-LST (SEQ ID NO: 58, encoded by SEQ ID NO: 57), and M23-LST_M23-LST_CWT-LST (SEQ ID NO: 70, encoded by SEQ ID NO: 69) with the most effective reference protein M23-LST_M23-LST_CWT-LST (SEQ ID NO: 70, encoded by SEQ ID NO: 69). At both concentrations tested (50 nM and 200 nM total protein concentrations), the mixtures were found slightly superior to M23-LST_M23-LST_CWT-LST (SEQ ID NO: 70, encoded by SEQ ID NO: 69) (FIG. 10).

Example 2

Material and Methods

The lysis kinetics of single and combinations/mixtures of protein constructs produced according to Example 1 have been tested using the turbidity reduction assay as described in the Material and Method section of Example 1.

Results

Lysis curves of the proteins and mixtures are shown in FIGS. 11 to 20. From these cures, maximum measured activity of each protein or mixture was calculated using 5-parameter sigmoidal fit model with SigmaPlot software. The first derivative of the slope is the maximum drop in optical density (OD595 nm) and is defined as maximum measured activity. Table 3 is a summary table of the maximum measured activity of each protein or mixture.

TABLE 1

Bacterial strains, bacteriophages and plasmids

| Strain, phage, or plasmid | Genotype or relevant characteristics | Source or reference |
|---|---|---|
| Bacterial strains | | |
| *E. coli* XL-1BlueMRF' | Δ mcrA 183 Δ mcrCB-hsdSMR-mrr 173 endA1 supE44 thi-1 recA1 gyrA96 relA1 lac[F' proAB laclq ZΔM15 Tn10 Tet'] | Stratagene |
| *E. coli* Sure | e14- McrA- Δ mcrCB-hsdSMR-mrr 171 endA1 supE44 thi-1 gyrA96 relA1 lac recB recJ sbcC umuC::Tn5 Kan' uvrC [F' proAB laclqZΔM15 Tn10 Tet'] | Stratagene |
| Phages | | |
| *S. aureus* Φ187 | Siphoviridae | Loessner et al. J Bacteriol 1999, 181: 4452-4460. |

TABLE 1-continued

Bacterial strains, bacteriophages and plasmids

| Strain, phage, or plasmid | Genotype or relevant characteristics | Source or reference |
| --- | --- | --- |
| S. aureus Φ2638 | Siphoviridae | Kwan et al. Proc Natl Acad Sci U S A 2005, 102: 5174-5179. |
| S. aureus ΦK | Siphoviridae | O'Flaherty et al. J Bacteriol 2005, 187: 7161-7164. |
| S. aureus ΦTw | Siphoviridae | Loessner et al. FEMS Microbiol Lett 1998, 162: 265-274. |
| Plasmids | | |
| pQE-30Xa | 3.4 kb cloning and expression vector; T5 promoter; creates N-terminal fusion of gene product with 21-aminoacid leader containing a 6x His-tag and Factor Xa protease cleavage site; Amp$^r$ | Qiagen |
| pHXaAm2638_CBD2638 | ply2638 fragment encoding Ala143 - Lys486 cloned into SacI - SalI sites of pQE-30Xa | This study |
| pHXaAm2638_CWT-LST | In-frame fusions of ply2638 fragment encoding Ala143 - Asp392 and pre- pro- lysostaphin encoding Trp402 - Lys493 cloned into SacI - SalI sites of pQE-30Xa | This study |
| pHXaAm2638_CWT-NM3 | In-frame fusions of ply2638 fragment encoding Ala143 - Asp392 and ply187 encoding Gly158 - Phe251 cloned into SacI - SalI sites of pQE-30Xa | This study |
| pHXaCHAPK_CBD2638 | In-frame fusions of lysK fragment encoding Met1 - Ala165 and ply2638 encoding Gly360 - Lys486 cloned into SacI - SalI sites of pQE-30Xa | This study |
| pHXaCHAPK_CWT-LST | In-frame fusions of lysK fragment encoding Met1 - Ala165 and pre-pro-lysostaphin encoding Gly388 - Lys493 cloned into SacI - SalI sites of pQE-30Xa | This study |
| pHXaCHAPK_CWT-NM3 | In-frame fusions of lysK fragment encoding Met1 - Ala165 and ply187 encoding Gly158 - Phe251 cloned into SacI - SalI sites of pQE-30Xa | This study |
| pHXaCHAPTw_CBD2638 | In-frame fusions of PlyTw fragment encoding Met1 - Asn182 and ply2638 encoding Trp393 - Lys486 cloned into SacI - SalI sites of pQE-30Xa | This study |
| pHXaCHAPTw_CWT-LST | In-frame fusions of PlyTw fragment encoding Met1 - Asn182 and pre-pro-lysostaphin encoding Trp402 - Lys493 cloned into SacI - SalI sites of pQE-30Xa | This study |
| pHXaCHAPTw_CWT-NM3 | In-frame fusions of PlyTw fragment encoding Met1 - Ala165 and ply187 encoding Gly158 - Phe251 cloned into SacI - SalI sites of pQE-30Xa | This study |
| pHXaM23-LST_CBD2638 | In-frame fusions of pre- pro- lysostaphin fragment encoding Ala251 - Pro398 and ply2638 encoding Trp393 - Lys486 cloned into SacI - SalI sites of pQE-30Xa | This study |
| pHXaM23-LST_CWT-LST | pre- pro- lysostaphin fragment encoding Ala251 - Lys493 cloned into SacI - SalI sites of pQE-30Xa | This study |
| pHXaM23-LST_CWT-NM3 | In-frame fusions of pre- pro- lysostaphin fragment encoding Ala251 - Gly401 and ply187 encoding Gly158 - Phe251 cloned into SacI - SalI sites of pQE-30Xa | This study |
| pHXaAm2638_Am2638_CBD2638 | ply2638 fragment encoding Ala143 - Gly359 cloned into StuI - SacI sites of pHXaAm2638_CBD2638 | This study |
| pHXaAm2638_Am2638_CWT-LST | ply2638 fragment encoding Ala143 - Gly359 cloned into StuI - SacI sites of pHXaAm2638_CWT-LST | This study |
| pHXaAm2638_Am2638_CWT-NM3 | ply2638 fragment encoding Ala143 - Gly359 cloned into StuI - SacI sites of pHXaAm2638_CWT-NM3 | This study |
| pHXaCHAPK_CHAPK_CBD2638 | lysK fragment encoding Met1 - Asn195 cloned into StuI - SacI sites of pHXaCHAPK_CBD2638 | This study |
| pHXaCHAPK_CHAPK_CWT-LST | lysK fragment encoding Met1 - Asn195 cloned into StuI - SacI sites of pHXaCHAPK_CWT-LST | This study |

TABLE 1-continued

Bacterial strains, bacteriophages and plasmids

| Strain, phage, or plasmid | Genotype or relevant characteristics | Source or reference |
|---|---|---|
| pHXaCHAPK_CHAPK_CWT-NM3 | lysK fragment encoding Met1 - Asn195 cloned into StuI - SacI sites of pHXaCHAPK_CWT-NM3 | This study |
| pHXaCHAPTw_CHAPTw_CBD2638 | plyTw fragment encoding Met1 - Asn182 cloned into StuI - SacI sites of pHXaCHAPTw_CBD2638 | This study |
| pHXaCHAPTw_CHAPTw_CWT-LST | plyTw fragment encoding Met1 - Asn182 cloned into StuI - SacI sites of pHXaCHAPTw_CWT-LST | This study |
| pHXaCHAPTw_CHAPTw_CWT-NM3 | plyTw fragment encoding Met1 - Asn182 cloned into StuI - SacI sites of pHXaCHAPTw_CWT-NM3 | This study |
| pHXaM23-LST_M23-LST_CBD2638 pHXaM23-LST_CBD2638 | pre- pro- lysostaphin fragment encoding Ala251 - Gly401 cloned into StuI - SacI sites of | Donovan et al. FEMS Microbiol Lett 2006, 265: 133-139. |
| pHXaM23-LST_M23-LST_CWT-LST | pre- pro- lysostaphin fragment encoding Ala251 - Gly401 cloned into StuI - SacI sites of pHXaM23-LST_CWT-LST | This study |
| pHXaM23-LST_M23-LST_CWT-NM3 | pre- pro- lysostaphin fragment encoding Ala251 - Gly401 cloned into StuI - SacI sites of pHXaM23-LST_CWT-NM3 | This study |

TABLE 2

SEQ ID NO overview table

| SEQ ID NO | Name construct | organism |
|---|---|---|
| 1 | Ply2638 endolysin CDS | Bacteriophage 2638A |
| 2 | Ply2638 endolysin PRT | Bacteriophage 2638A |
| 3 | CWT-LST CDS | S. simulans |
| 4 | CWT-LST PRT | S. simulans |
| 5 | CBD2638 CDS | Bacteriophage 2638A |
| 6 | CBD2638 PRT | Bacteriophage 2638A |
| 7 | CWT-NM3 CDS | S. aureus phage phiNM3 |
| 8 | CWT-NM3 PRT | S. aureus phage phiNM3 |
| 9 | CHAPK CDS | S. phage K |
| 10 | CHAPK PRT | S. phage K |
| 11 | CHAP-φTwort CDS | S. phage Twort |
| 12 | CHAP-φTwort PRT | S. phage Twort |
| 13 | M23-2638 CDS | Bacteriophage 2638A |
| 14 | M23-2638 PRT | Bacteriophage 2638A |
| 15 | M23-LST CDS | S. simulans |
| 16 | M23-LST PRT | S. simulans |
| 17 | Ami2638 CDS | Bacteriophage 2638A |
| 18 | Ami2638 PRT | Bacteriophage 2638A |
| 19 | CHAPK_CHAPK_CWT-LST CDS | artificial construct |
| 20 | CHAPK_CHAPK_CWT-LST PRT | artificial construct |
| 21 | M23-LST_M23-LST_CWT-LST CDS | artificial construct |
| 22 | M23-LST_M23-LST_CWT-LST PRT | artificial construct |
| 23 | Ami2638_ami2638_CWT-LST CDS | artificial construct |
| 24 | Ami2638_ami2638_CWT-LST PRT | artificial construct |
| 25 | HXaAmi2638_CBD2638 CDS | artificial construct |
| 26 | HXaAmi2638_CBD2638 PRT | artificial construct |
| 27 | HXaAmi2638_CWT-LST CDS | artificial construct |
| 28 | HXaAmi2638_CWT-LST PRT | artificial construct |
| 29 | HXaAmi2638_CWT-NM3 CDS | artificial construct |
| 30 | HXaAmi2638_CWT-NM3 PRT | artificial construct |
| 31 | HXaCHAPK_CBD2638 CDS | artificial construct |
| 32 | HXaCHAPK_CBD2638 PRT | artificial construct |
| 33 | HXaCHAPK_CWT-LST CDS | artificial construct |
| 34 | HXaCHAPK_CWT-LST PRT | artificial construct |
| 35 | HXaCHAPK_CWT-NM3 CDS | artificial construct |
| 36 | HXaCHAPK_CWT-NM3 PRT | artificial construct |
| 37 | HXaCHAPTw_CBD2638 CDS | artificial construct |
| 38 | HXaCHAPTw_CBD2638 PRT | artificial construct |
| 39 | HXaCHAPTw_CWT-LST CDS | artificial construct |
| 40 | HXaCHAPTw_CWT-LST PRT | artificial construct |
| 41 | HXaCHAPTw_CWT-NM3 CDS | artificial construct |
| 42 | HXaCHAPTw_CWT-NM3 PRT | artificial construct |
| 43 | HXaM23-LST_CBD2638 CDS | artificial construct |
| 44 | HXaM23-LST_CBD2638 PRT | artificial construct |
| 45 | HXaM23-LST_CWT-LST CDS | artificial construct |
| 46 | HXaM23-LST_CWT-LST PRT | artificial construct |
| 47 | HXaM23-LST_CWT-NM3 CDS | artificial construct |
| 48 | HXaM23-LST_CWT-NM3 PRT | artificial construct |
| 49 | HXaAmi2638_Ami2638_CBD2638 CDS | artificial construct |
| 50 | HXaAmi2638_Ami2638_CBD2638 PRT | artificial construct |
| 51 | HXaAmi2638_Ami2638_CWT-LST CDS | artificial construct |
| 52 | HXaAmi2638_Ami2638_CWT-LST PRT | artificial construct |
| 53 | HXaAmi2638_Ami2638_CWT-NM3 CDS | artificial construct |
| 54 | HXaAmi2638_Ami2638_CWT-NM3 PRT | artificial construct |
| 55 | HXaCHAPK_CHAPK_CBD2638 CDS | artificial construct |
| 56 | HXaCHAPK_CHAPK_CBD2638 PRT | artificial construct |
| 57 | HXaCHAPK_CHAPK_CWT-LST CDS | artificial construct |
| 58 | HXaCHAPK_CHAPK_CWT-LST PRT | artificial construct |
| 59 | HXaCHAPK_CHAPK_CWT-NM3 CDS | artificial construct |
| 60 | HXaCHAPK_CHAPK_CWT-NM3 PRT | artificial construct |
| 61 | HXaCHAPTw_CHAPTw_CBD2638 CDS | artificial construct |
| 62 | HXaCHAPTw_CHAPTw_CBD2638 PRT | artificial construct |
| 63 | HXaCHAPTw_CHAPTw_CWT-LST CDS | artificial construct |
| 64 | HXaCHAPTw_CHAPTw_CWT-LST PRT | artificial construct |
| 65 | HXaCHAPTw_CHAPTw_CWT-NM3 CDS | artificial construct |
| 66 | HXaCHAPTw_CHAPTw_CWT-NM3 PRT | artificial construct |
| 67 | HXaM23-LST_M23-LST_CBD2638 CDS | artificial construct |
| 68 | HXaM23-LST_M23-LST_CBD2638 PRT | artificial construct |
| 69 | HXaM23-LST_M23-LST_CWT-LST CDS | artificial construct |
| 70 | HXaM23-LST_M23-LST_CWT-LST PRT | artificial construct |

TABLE 2-continued

SEQ ID NO overview table

| SEQ ID NO | Name construct | organism |
|---|---|---|
| 71 | HXaM23-LST_M23-LST_CWT-NM3 CDS | artificial construct |
| 72 | HXaM23-LST_M23-LST_CWT-NM3 PRT | artificial construct |
| 73 | His-tag with linker CDS | artificial construct |
| 74 | His-tag with linker PRT | artificial construct |

TABLE 3

Results of Example 2.

| protein construct | SEQ ID NO | mean ($\Delta_{max}$OD$_{595\,nm}$*min$^{-1}$) | std.dev. | std.err. |
|---|---|---|---|---|
| *Single protein constructs (30 nM protein concentration)* | | | | |
| HXaAmi2638_CWT-LST | 28 | −0.004345 | 0.000722 | 0.000511 |
| HXaCHAPK_CWT-LST | 34 | −0.005163 | 0.000552 | 0.000390 |
| HXaM23-LST_CWT-LST | 46 | −0.013310 | 0.000387 | 0.000224 |
| HXaAmi2638_Ami2638_CWT-LST | 52 | −0.006686 | 0.000462 | 0.000267 |
| HXaCHAPK_CHAPK_CWT-LST | 58 | −0.004086 | 0.000304 | 0.000176 |
| HXaM23-LST_M23-LST_CWT-LST | 70 | −0.040422 | 0.000624 | 0.000360 |
| *Mixtures of two protein constructs (30 nM total, 15 nM each protein)* | | | | |
| HXaAmi2638_CWT-LST HXaCHAPK_CWT-LST | 28 + 34 | −0.004492 | 0.000222 | 0.000157 |
| HXaAmi2638_Ami2638_CWT-LST HXaCHAPK_CHAPK_CWT-LST | 52 + 58 | −0.010524 | 0.002527 | 0.001459 |
| HXaAmi2638_Ami2638_CWT-LST HXaCHAPK_CWT-LST | 52 + 34 | −0.004471 | 0.000125 | 0.000072 |
| HXaAmi2638_CWT-LST HXaCHAPK_CHAPK_CWT-LST | 28 + 58 | −0.006872 | 0.000850 | 0.000491 |
| HXaAmi2638_CWT-LST HXaM23-LST_CWT-LST | 28 + 46 | −0.018363 | 0.000199 | 0.000115 |
| HXaAmi2638_Ami2638_CWT-LST HXaM23-LST_M23-LST_CWT-LST | 52 + 70 | −0.060616 | 0.004117 | 0.002377 |
| HXaAmi2638_Ami2638_CWT-LST HXaM23-LST_CWT-LST | 52 + 46 | −0.020094 | 0.001989 | 0.001148 |
| HXaAmi2638_CWT-LST HXaM23-LST_M23-LST_CWT-LST | 28 + 70 | −0.049715 | 0.005762 | 0.003327 |
| HXaCHAPK_CWT-LST HXaM23-LST_CWT-LST | 34 + 46 | −0.009839 | 0.000700 | 0.000404 |
| HXaCHAPK_CHAPK_CWT-LST HXaM23-LST_M23-LST_CWT-LST | 58 + 70 | −0.039957 | 0.001111 | 0.000641 |
| HXaCHAPK_CHAPK_CWT-LST HXaM23-LST_CWT-LST | 58 + 46 | −0.011577 | 0.003904 | 0.002254 |
| HXaCHAPK_CWT-LST HXaM23-LST_M23-LST_CWT-LST | 34 + 70 | −0.029355 | 0.000913 | 0.000527 |
| *Mixtures of three protein constructs (30 nM total, 10 nM each protein)* | | | | |
| HXaAmi2638_CWT-LST HXaCHAPK_CWT-LST HXaM23-LST_CWT-LST | 28 + 34 + 46 | −0.013973 | 0.001444 | 0.000834 |
| HXaAmi2638_Ami2638_CWT-LST HXaCHAPK_CHAPK_CWT-LST HXaM23-LST_M23-LST_CWT-LST | 52 + 58 + 70 | −0.052270 | 0.007606 | 0.004391 |
| HXaAmi2638_CWT-LST HXaCHAPK_CHAPK_CWT-LST HXaM23-LST_M23-LST_CWT-LST | 28 + 58 + 70 | −0.045011 | 0.003443 | 0.001988 |
| HXaAmi2638_Ami2638_CWT-LST HXaCHAPK_CWT-LST HXaM23-LST_M23-LST_CWT-LST | 52 + 34 + 70 | −0.042337 | 0.003308 | 0.001910 |
| HXaAmi2638_Ami2638_CWT-LST HXaCHAPK_CHAPK_CWT-LST HXaM23-LST_CWT-LST | 52 + 58 + 46 | −0.020569 | 0.003307 | 0.001910 |
| HXaAmi2638_Ami2638_CWT-LST HXaCHAPK_CWT-LST HXaM23-LST_CWT-LST | 52 + 34 + 46 | −0.016268 | 0.000576 | 0.000333 |
| HXaAmi2638_CWT-LST HXaCHAPK_CHAPK_CWT-LST HXaM23-LST_CWT-LST | 28 + 58 + 46 | −0.013975 | 0.000365 | 0.000211 |
| HXaAmi2638_CWT-LST HXaCHAPK_CWT-LST HXaM23-LST_M23-LST_CWT-LST | 28 + 34 + 70 | −0.036804 | 0.003481 | 0.002010 |

TABLE 3-continued

Results of Example 2.

| protein construct | SEQ ID NO | mean ($\Delta_{max}OD_{595\ nm}$*min$^{-1}$) | std.dev. | std.err. |
|---|---|---|---|---|
| Single protein constructs (50 nM proteinconcentration) | | | | |
| HXaAmi2638_CWT-LST | 28 | −0.005109 | 0.000061 | 0.000035 |
| HXaCHAPK_CWT-LST | 34 | −0.004037 | 0.000369 | 0.000261 |
| HXaM23-LST_CWT-LST | 46 | −0.022770 | 0.000304 | 0.000175 |
| HXaAmi2638_Ami2638_CWT-LST | 52 | −0.008042 | 0.000593 | 0.000342 |
| HXaCHAPK_CHAPK_CWT-LST | 58 | −0.003674 | 0.000121 | 0.000086 |
| HXaM23-LST_M23-LST_CWT-LST | 70 | −0.054314 | 0.000820 | 0.000474 |
| Mixtures of two protein constructs (50 nM total, 25 nM each protein) | | | | |
| HXaAmi2638_CWT-LST<br>HXaCHAPK_CWT-LST | 28 + 34 | −0.004611 | 0.000945 | 0.000668 |
| HXaAmi2638_Ami2638_CWT-LST<br>HXaCHAPK_CHAPK_CWT-LST | 52 + 58 | −0.007071 | 0.000287 | 0.000203 |
| HXaAmi2638_Ami2638_CWT-LST<br>HXaCHAPK_CWT-LST | 52 + 34 | −0.006845 | 0.000578 | 0.000334 |
| HXaAmi2638_CWT-LST<br>HXaCHAPK_CHAPK_CWT-LST | 28 + 58 | −0.005107 | 0.000756 | 0.000436 |
| HXaAmi2638_CWT-LST<br>HXaM23-LST_CWT-LST | 28 + 46 | −0.029038 | 0.000591 | 0.000341 |
| HXaAmi2638_Ami2638_CWT-LST<br>HXaM23-LST_M23-LST_CWT-LST | 52 + 70 | −0.077677 | 0.005683 | 0.003281 |
| HXaAmi2638_Ami2638_CWT-LST<br>HXaM23-LST_CWT-LST | 52 + 46 | −0.033351 | 0.001808 | 0.001044 |
| HXaAmi2638_CWT-LST<br>HXaM23-LST_M23-LST_CWT-LST | 28 + 70 | −0.076113 | 0.000463 | 0.000268 |
| HXaCHAPK_CWT-LST<br>HXaM23-LST_CWT-LST | 34 + 46 | −0.014407 | 0.000917 | 0.000529 |
| HXaCHAPK_CHAPK_CWT-LST<br>HXaM23-LST_M23-LST_CWT-LST | 58 + 70 | −0.048809 | 0.000527 | 0.000304 |
| HXaCHAPK_CHAPK_CWT-LST<br>HXaM23-LST_CWT-LST | 58 + 46 | −0.018130 | 0.001014 | 0.000586 |
| HXaCHAPK_CWT-LST<br>HXaM23-LST_M23-LST_CWT-LST | 34 + 70 | −0.046676 | 0.002135 | 0.001233 |
| Mixtures of three protein constructs (50 nM total, 16.67 nM each protein) | | | | |
| HXaAmi2638_CWT-LST<br>HXaCHAPK_CWT-LST<br>HXaM23-LST_CWT-LST | 28 + 34 + 46 | −0.020491 | 0.001630 | 0.000941 |
| HXaAmi2638_Ami2638_CWT-LST<br>HXaCHAPK_CHAPK_CWT-LST<br>HXaM23-LST_M23-LST_CWT-LST | 52 + 58 + 70 | −0.062127 | 0.002998 | 0.001731 |
| HXaAmi2638_CWT-LST<br>HXaCHAPK_CHAPK_CWT-LST<br>HXaM23-LST_M23-LST_CWT-LST | 28 + 58 + 70 | −0.054493 | 0.002078 | 0.001200 |
| HXaAmi2638_Ami2638_CWT-LST<br>HXaCHAPK_CWT-LST<br>HXaM23-LST_M23-LST_CWT-LST | 52 + 34 + 70 | −0.054908 | 0.000584 | 0.000337 |
| HXaAmi2638_Ami2638_CWT-LST<br>HXaCHAPK_CHAPK_CWT-LST<br>HXaM23-LST_CWT-LST | 52 + 58 + 46 | −0.025062 | 0.000831 | 0.000480 |
| HXaAmi2638_Ami2638_CWT-LST<br>HXaCHAPK_CWT-LST<br>HXaM23-LST_CWT-LST | 52 + 34 + 46 | −0.023737 | 0.000656 | 0.000379 |
| HXaAmi2638_CWT-LST<br>HXaCHAPK_CHAPK_CWT-LST<br>HXaM23-LST_CWT-LST | 28 + 58 + 46 | −0.018786 | 0.000215 | 0.000124 |
| HXaAmi2638_CWT-LST<br>HXaCHAPK_CWT-LST<br>HXaM23-LST_M23-LST_CWT-LST | 28 + 34 + 70 | −0.051336 | 0.000409 | 0.000236 |

What is claimed is:

1. A composition comprising a combination of a source of a first enzymatic active domain and a source of a second enzymatic active domain, wherein said source comprises a polypeptide, wherein said first and second enzymatic active domains each exhibit distinct target bond specificities and are comprised on a distinct first and second polypeptide, and wherein said first and second polypeptide comprise a different number of copies of said first and/or second enzymatic active domain, and wherein said first polypeptide comprises a sequence that has at least 80% sequence identity to SEQ ID NO: 58, said second polypeptide comprises a sequence that has at least 80% sequence identity to SEQ ID NO: 70.

2. A composition according to claim 1, wherein said different target bonds are essential bonds in a peptidoglycan layer of a bacterial cell, wherein said bacterial cell is a Staphylococcus.

3. The composition according to claim 1, wherein:
said combination further comprises a source of a third enzymatic active domain comprised on a distinct third polypeptide,
said third enzymatic active domain is an amidase domain,
said distinct third polypeptide further comprises a cell wall-binding domain, and
each of said distinct first, second and third polypeptide comprises a different number of copies of said first, second and third enzymatic active domain.

4. The composition according to claim 3, wherein said third polypeptide comprises a sequence that has at least 80% sequence identity SEQ ID NO: 52.

5. The composition according to claim 1, further comprising an pharmaceutical acceptable carrier and/or an additional active ingredient selected from the group consisting of a bacteriophage, a bacteriostatic agent, a bactericide agent, an antibiotic, a surfactant and/or an enzyme.

6. A composition comprising a combination of a source of a first enzymatic active domain, a source of a second enzymatic active domain, and a source of a third enzymatic domain,
   wherein said source comprises a polypeptide;
   wherein each of said first, second and third enzymatic active domains exhibits distinct target bond specificities and are comprised of distinct first, second and third polypeptides and each of said distinct first, second and third polypeptides comprises a different number of copies of said first, second and third enzymatic active domains, and further comprises a cell wall-binding domain;
   wherein said first enzymatic active domain is a cysteine, histidine-dependent amidohydrolases/peptidase domain, said second enzymatic active domain is an endopeptidase domain, said third enzymatic domain is an amidase domain; and
   wherein said first polypeptide comprises a sequence that has at least 80% sequence identity to SEQ ID NO: 58, said second polypeptide comprises a sequence that has at least 80% sequence identity SEQ ID NO: 70 and said third polypeptide comprises a sequence that has at least 80% sequence identity SEQ ID NO: 52.

7. A method of treatment, prevention or delay of a Staphylococcus related condition in an individual, comprising administering to said individual a composition according to claim 1.

* * * * *